(12) United States Patent
Bachmann et al.

(10) Patent No.: US 8,772,510 B2
(45) Date of Patent: Jul. 8, 2014

(54) PDE10 MODULATORS

(75) Inventors: Stephan Bachmann, Allschwil (CH); Alexander Flohr, Loerrach (DE); Katrin Groebke Zbinden, Liestal (CH); Matthias Koerner, Grenzach-Wyhlen (DE); Bernd Kuhn, Reinach BL (CH); Jens-Uwe Peters, Grenzach-Wyhlen (DE); Markus Rudolph, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/598,848

(22) Filed: Aug. 30, 2012

(65) Prior Publication Data

US 2013/0059833 A1 Mar. 7, 2013

(30) Foreign Application Priority Data

Sep. 6, 2011 (EP) .................... 11180135

(51) Int. Cl.
- *C07D 249/04* (2006.01)
- *C07D 233/54* (2006.01)
- *C07D 231/10* (2006.01)
- *C07D 207/30* (2006.01)

(52) U.S. Cl.
USPC ........... 548/560; 548/124; 548/125; 548/146; 548/206; 548/255; 548/335.1; 548/373.1

(58) Field of Classification Search
None
See application file for complete search history.

(56) References Cited

U.S. PATENT DOCUMENTS

| | | | |
|---|---|---|---|
| 2010/0136136 A1 | 6/2010 | Galan et al. | |
| 2011/0294779 A1 | 12/2011 | Alberati et al. | |

FOREIGN PATENT DOCUMENTS

| | | |
|---|---|---|
| WO | 2005/012485 | 2/2005 |
| WO | WO 2008042282 A2 * | 4/2008 |
| WO | 2011/036127 | 3/2011 |

OTHER PUBLICATIONS

Kehler et al. The potential therapeutic use of phosphodiesterases 10 inhibitors. Expert Opin. Ther. Patents (2007) vol. 17, pp. 147-158.*
Lippard The art of Chemistry. Nature 2002, vol. 416, pp. 587.*
Soderling et al., "Curr. Opin. Cell Biol." 12:174-179 ( 2000).
Siuciak et al., "Neuropharmacology" 51(2):386-396 ( 2006).
Conti et al., "Prog. Nucleic Acid Res. Mol. Biol." 63:1-38 ( 1999).
Soderling et al., "Proc. Natl. Acad. Sci. USA" 96(12):7071-7076 ( 1999).
Manallack et al., "J. Med. Chem." 48(10):3449-3462 ( 2005).
Sano, H., "J. Neurochem." 105:546-556 ( 2008).
Coskran et al., "J. Histochem. Cytochem." 54(11):1205-1213 ( 2006).
Nakazato et al., "Expert Opinion on Therapeutic Patents" 10(1):75-98 ( 2000).
Fujishige et al., "Eur. J. Biochem." 266(3):1118-1127 ( 1999).
Loughney et al., "Gene" 234(1):109-117 ( 1999).
Beavo et al., "Physiol. Rev." 75:725-748 ( 1995).
Sharma et al., "Br. J. Psychiatry" ((Suppl. 28)), 174:44-51 ( 1999).
Siuciak et al., "Neuropharmacology" 51(2):374-385 ( 2006).
Lewis DA, Lieberman JA, Neuron 28:325-333 ( 2000).
Vandenberg et al., "Exp. Opin. Ther. Targets" 5(4):507-518 ( 2001).
Seeger et al., "Brain Research" 985:113-126 ( 2003).
Javitt et al., "Biol. Psychiatry" 45:668-679 ( 1999).
Rodefer et al., "Eur. J. Neuroscience" 2:1070-1076 ( 2005).
(International Search Report in PCT/2012/067047 Oct. 25, 2012).
Fujishige et al., "J. Biol. Chem." 274:18438-18445 ( 1999).
Graybiel, A. M., "Curr. Biol." 10:R509-R511 ( 2000).
The English translation of the Taiwanese Search Report, issued on Oct. 9, 2013, in the corresponding Taiwanese application No. 101132392.

* cited by examiner

*Primary Examiner* — Leslie A. Royds Draper
*Assistant Examiner* — Taina D Matos Negron

(57) ABSTRACT

The present invention relates to compounds of formula (I)

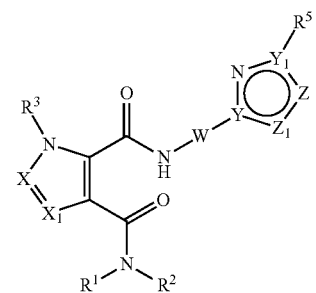

wherein $R^1$, $R^2$, $R^3$, $R^5$, W, X, $X_1$, Y, $Y_1$, Z and $Z_1$ are as defined in the description and in the claims, as well as physiologically acceptable salts thereof. These compounds inhibit PDE10A and can be used in the treatment of CNS disorders such as schizophrenia, Alzheimer's disease, and Parkinson's disease.

25 Claims, No Drawings

PDE10 MODULATORS

PRIORITY TO RELATED APPLICATION(S)

This application claims the benefit of European Patent Application No. 11180135.3, filed Sep. 6, 2011, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325-33, 2000). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 5(4): 507-518, 2001; Nakazato A and Okuyama S, et al., Exp. Opin. Ther. Patents, 10(1): 75-98, 2000). This pharmacological approach, besides ameliorating positive symptoms in schizophrenic patients, poorly addresses negative and cognitive symptoms which are the best predictors of functional outcome (Sharma T., Br. J. Psychiatry, 174 (suppl. 28): 44-51, 1999). In addition, current antipsychotic treatment is associated with adverse effects like weight gain, extrapyramidal symptoms or effects on glucose and lipid metabolism, related to their unspecific pharmacology.

In conclusion there is still a need for developing new antipsychotics with improved efficacy and safety profile. A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly, in healthy volunteers PCP-induced psychotomimetic action incorporates positive and negative symptoms as well as cognitive dysfunction, thus closely resembling schizophrenia in patients (Javitt D C et al., Biol. Psychiatry, 45: 668-679, 1999).

Cyclic nucleotides cyclic adenosine monophosphate (cAMP) and cyclic guanosine monophosphate (cGMP) are ubiquitous second messengers responsible for mediating the biological response of a variety of extracellular signals, including neurotransmitters, light and hormones. cAMP and cGMP regulate a variety of intracellular processes particularly in neurons of the central nervous system by activating cAMP- and cGMP-dependent kinases which then phosphorylate proteins involved in the regulation of synaptic transmission, neuronal differentiation and survival.

A crucial mechanism for controlling intracellular cyclic nucleotide levels and therefore cyclic nucleotide signaling is via hydrolysis of the 3',5'-phosphodiester bond by phosphodiesterases. Phosphodiesterases (PDEs) are a family of widely expressed enzymes encoded by 21 different genes in humans, with each gene encoding several splice variants (Beavo, J., Physiol. Rev. 1995, 75, 725-748; Conti, M., Jin, S. L., Prog. Nucleic Acid Res. Mol. Biol. 1999, 63, 1-38; Soderling, S. H., Beavo, J. A., Curr. Opin. Cell Biol. 2000, 12, 174-179, Manallack, D. T. et al. J. Med. Chem. 2005, 48 (10), 3449-3462).

The PDE families differ in their substrate specificity for the cyclic nucleotides, their mechanism of regulation and their sensitivity to inhibitors. Moreover, they are differentially localized in the organism, among the cells of an organ and even within the cells. These differences lead to a differentiated involvement of the PDE families in the various physiological functions.

PDE10A is a dual substrate PDE encoded by a single gene as reported in 1999 by three separate research groups (Fujishige K., et al., Eur J Biochem (1999) 266(3):1118-1127, Soderling S. H., et al., Proc Natl Acad Sci USA (1999) 96(12):7071-7076, Loughney K., et al., Gene (1999) 234(1): 109-117). PDE10A is unique from other members of the multigene family with respect to amino acid sequence (779 aa), tissue-specific pattern of expression, affinity for cAMP and cGMP and the effect on PDE activity by specific and general inhibitors.

PDE10A has one of the most restricted distribution of any PDE family being primarily expressed in the brain particularly in the nucleus accumbens and the caudate putamen. Additionally thalamus, olfactory bulb, hippocampus and frontal cortex show moderate levels of PDE10A expression. All these brain areas have been suggested to be involved in the pathophysiology of schizophrenia and psychosis, suggesting a central role of PDE10A in this devastating mental illness. Outside the central nervous system PDE10A transcript expression is also observed in peripheral tissues like thyroid gland, pituitary gland, insulin secreting pancreatic cells and testes (Fujishige, K. et al., J. Biol. Chem. 1999, 274, 18438-18445, Sweet, L. (2005) WO 2005/012485). On the other hand expression of PDE10A protein has been observed only in enteric ganglia, in testis and epididymal sperm (Coskran T. M, et al., J. Histochem. Cytochem. 2006, 54 (11), 1205-1213).

In the striatum both mRNA and protein are expressed only in the GABA (γ-aminobutyric acid)-containing medium spiny projection neurons making it an intriguing target for the treatment of diseases of the central nervous system (Fujishige, K. et al., Eur. J. Biochem. 1999, 266, 1118-1127; Seeger, T. F. et al., Brain Res. 2003, 985, 113-126). The striatal medium spiny neurons are the principal input site and first site for information integration in the basal ganglia circuit of the mammalian brain. The basal ganglia are a series of interconnected subcortical nuclei that integrate widespread cortical input with dopaminergic signaling to plan and execute relevant motor and cognitive patterns while suppressing unwanted or irrelevant patterns (Graybiel, A. M. Curr. Biol. 2000, 10, R509-R511 (2000).

Papaverine, a relatively specific PDE10A inhibitor, and PDE10A-knockout mice have been used to explore the physiology of this enzyme and the possible therapeutic utility of PDE10A inhibition. Inhibition of this enzyme pharmacologically or through gene disruption causes a reduction in activity and a reduced response to psychomotor stimulants Inhibition also reduces the conditioned avoidance response, a behavioural response that is predictive of clinical antipsychotic activity (Siuciak, J. A.; et al., Neuropharmacology 2006, 51 (2), 386-396; Siuciak, J. A.; et al., Neuropharmacology 2006, 51 (2), 374-385).

In addition PDE10A inhibition bears the potential to improve the negative and cognitive symptoms associated to schizophrenia. Indeed papaverine have been shown to attenuate the deficits in the extra-dimensional shift learning induced in rats by sub-chronic treatment with PCP, an animal paradigm of NMDA receptor hypofunction (Rodefer, J. S., et al., Eur. J. Neuroscience 2005, 2: 1070-1076). In addition increased social interaction in PDE10A2-deficient mice have been observed (Sano, H. J. Neurochem. 2008, 105, 546-556).

Diseases that can be treated with PDE10A inhibitors include, but are not limited to, diseases thought to be mediated in part by dysfunction of the basal ganglia, of other parts of the central nervous system and of other PDE10A expressing tissues. In particular, diseases can be treated, where inhibition of PDE10A can have therapeutic effects.

These diseases include, but are not limited to, certain psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders.

PDE10A inhibitors might also be useful in preventing neurons from undergoing apoptosis by raising cAMP and cGMP levels and, thus, might possess anti-inflammatory properties. Neurodegenerative disorders treatable with PDE10A inhibitors include, but are not limited to, as Alzheimer's disease, Huntington's disease, Parkinson's disease, multiple sclerosis, stroke or spinal cord injury.

The growth of cancer cells is inhibited by cAMP and cGMP. Thus by raising cAMP and cGMP, PDE10A inhibitors can also be used for the treatment of different solid tumors and hematological malignancies such as renal cell carcinoma or breast cancer.

SUMMARY OF THE INVENTION

The invention provides novel compounds of formula (I)

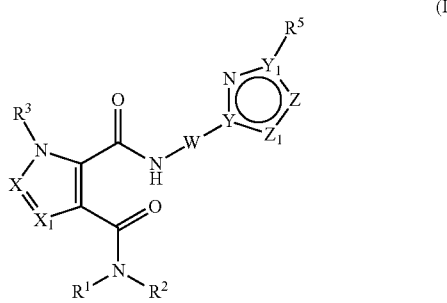

wherein:
X and $X_1$ are each independently $CR^4$ or N;
Y and $Y_1$ are each independently C or N;
Z and $Z_1$ are each independently $CR^6$, $NR^7$, N, O or S;
$R^1$ and $R^2$ are each independently selected from hydrogen, $C_1$-$C_7$-alkyl, $C_3$-$C_8$-cycloalkyl, $C_1$-$C_7$-haloalkyl, $C_1$-$C_7$-alkoxy-$C_1$-$C_7$-alkyl, heterocycloalkyl or $C_1$-$C_7$-alkyl optionally substituted by aryl or heteroaryl or
$R^1$ and $R^2$, together with the nitrogen atom to which they are attached, form a bicyclic ring system or a heterocycloalkyl optionally substituted by 1 to 3 substituents independently selected from the group consisting of hydroxyl, halogen, $C_1$-$C_7$-alkyl, $C_1$-$C_7$-alkoxy, $C_1$-$C_7$-haloalkyl and oxo;
$R^3$ is hydrogen or $C_1$-$C_7$ alkyl;
$R^4$ is hydrogen, $C_1$-$C_7$ alkyl, $C_3$-$C_8$-cycloalkyl, $C_1$-$C_7$-haloalkyl or halogen;
$R^5$ is aryl or heteroaryl each of which is optionally substituted by $C_1$-$C_7$-alkyl, $C_3$-$C_8$-cycloalkyl, halogen, $C_1$-$C_7$haloalkyl, $C_1$-$C_7$ alkoxy, hydroxyl, $C_1$-$C_7$ hydroxyalkyl, $C_1$-$C_7$ alkoxyalkyl, acetyl, cyano, or amino optionally substituted by one or two $C_1$-$C_7$ alkyl groups;
$R^6$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl or
$R^5$ and $R^6$, together with the $Y_1$ and Z atoms to which they are attached, form aryl or heteroaryl each of which is optionally substituted by $C_1$-$C_7$ alkyl, halogen, $C_1$-$C_7$-alkoxy, $C_1$-$C_7$-haloalkyl;
$R^7$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, cycloalkyl or
$R^5$ and $R^7$, together with the $Y_1$ and Z atoms to which they are attached, form aryl or heteroaryl each of which is optionally substituted by $C_1$-$C_7$ alkyl, halogen, $C_1$-$C_7$-alkoxy, $C_1$-$C_7$-haloalkyl; W is ethylene or ethenylene each of which is optionally substituted by $C_1$-$C_7$ alkyl or halogen or W is —N=CH—.

Further, the invention provides a process for the manufacture of the above compounds, pharmaceutical compositions containing them, as well as the use of these compounds for the production of pharmaceutical compositions.

The compounds of the present invention are useful for the treatment of psychotic disorders such as schizophrenia, positive, negative and/or cognitive symptoms associated with schizophrenia, delusional disorder or substance-induced psychotic disorder, anxiety disorders such as panic disorder, obsessive-compulsive disorder, acute stress disorder or generalized anxiety disorder, obsessive/compulsive disorders, drug addictions, movement disorders such as Parkinson's disease or restless leg syndrome, cognition deficiency disorders such as Alzheimer's disease or multi-infarct dementia, mood disorders such as depression or bipolar disorders, or neuropsychiatric conditions such as psychosis, attention-deficit/hyperactivity disorder (ADHD) or related attentional disorders. Compounds of the invention also are useful for the treatment of Huntington's disease, multiple sclerosis, stroke or spinal cord injury.

Compounds of the invention can be used for the treatment of different solid tumors and hematological malignancies such as renal cell carcinoma or breast cancer. Further, compounds of the invention are useful for the treatment of diabetes and related disorders such as obesity by regulating the cAMP signaling system.

DETAILED DESCRIPTION OF THE INVENTION

Unless otherwise indicated, the following definitions are set forth to illustrate and define the meaning and scope of the various terms used to describe the invention herein.

It must be noted that, as used in the specification and the claims, the singular forms "a", "an" and "the" include plural referents unless the context clearly dictates otherwise.

When indicating the number of substituents, the term "one or more" means from one substituent to the highest possible number of substitution, i.e. replacement of one hydrogen up to replacement of all hydrogens by substituents.

The term "alkyl" denotes a monovalent linear or branched saturated hydrocarbon group of 1 to 12 carbon atoms. In particular embodiments, alkyl has 1 to 7 carbon atoms and is referred to herein as "$C_1$-$C_7$alkyl," and in more particular embodiments 1 to 4 carbon atoms and is referred to herein as "$C_1$-$C_4$alkyl." Examples of alkyl include methyl, ethyl, propyl, isopropyl, n-butyl, iso-butyl, sec-butyl, and tert-butyl.

The term "alkylene" denotes a linear saturated divalent hydrocarbon group of 1 to 7 carbon atoms or a divalent branched saturated divalent hydrocarbon group of 3 to 7 carbon atoms. Examples of alkylene groups include methylene, ethylene, propylene, 2-methylpropylene, butylene, 2-ethylbutylene, pentylene, and hexylene.

The term "alkenylene" denotes a linear divalent hydrocarbon chain of 2 to 7 carbon atoms or a branched divalent hydrocarbon chain of 3 to 7 carbon atoms having at least one double bond. Exemplary alkenylene groups include ethenylene, 2,2-dimethylethenylene, propenylene, 2-methylpropenylene, butenylene, and pentenylene.

The term "alkoxy" denotes a group of the formula —O—R', wherein R' is an alkyl group as defined above. "$C_1$-$C_7$alkoxy" refers to an alkoxy group in which the alkyl group has from 1 to 7 carbon atoms. Examples of alkoxy moieties include methoxy, ethoxy, isopropoxy, and tert-butoxy.

The term "alkoxyalkyl" denotes an alkyl group wherein at least one of the hydrogen atoms of the alkyl group has been replaced by an alkoxy group. "$C_1$-$C_7$-alkoxy-$C_1$-$C_7$-alkyl" refers to an alkyl group having from 1 to 7 carbon atoms in which at least one of the hydrogen atoms of the alkyl group has been replaced by an alkoxy group in which the alkyl portion is from 1 to 7 carbon atoms. Exemplary alkoxyalkyl groups include 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

The term "amino" denotes a group of the formula —NR'R" wherein R' and R" are independently hydrogen, alkyl, alkoxy, cycloalkyl, heterocycloalkyl, aryl or heteroaryl. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is not. The term "tertiary amino" denotes a group wherein both R' and R" are not hydrogen. Particular secondary and tertiary amines are methylamine, ethylamine, propylamine, isopropylamine, phenylamine, benzylamine dimethylamine, diethylamine, dipropylamine and diisopropylamine.

The term "cycloalkyl" denotes a monovalent saturated monocyclic or bicyclic hydrocarbon group of 3 to 10 ring carbon atoms. In particular, cycloalkyl denotes a monovalent saturated monocyclic hydrocarbon group of 3 to 8 ring carbon atoms and is referred to as "$C_3$-$C_8$-cycloalkyl." Bicyclic means consisting of two saturated carbocycles having one or more carbon atoms in common. Particular cycloalkyl groups are monocyclic. Examples for monocyclic cycloalkyl are cyclopropyl, cyclobutenyl, cyclopentyl, cyclohexyl or cycloheptyl. Examples for bicyclic cycloalkyl are bicyclo[2.2.1]heptanyl, and bicyclo[2.2.2]octaenyl.

The term "halogen" refers to fluorine, chlorine, bromine and iodine, more specifically fluorine, chlorine and bromine.

The term "haloalkyl" denotes an alkyl group wherein at least one of the hydrogen atoms of the alkyl group has been replaced by same or different halogen atoms, particularly fluoro atoms. "$C_1$-$C_7$-haloalkyl" denotes a $C_1$-$C_7$ alkyl group in which at least one of the hydrogen atoms has been replaced by same or different halogen atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, and trifluoromethyl. The term "perhaloalkyl" denotes an alkyl group where all hydrogen atoms of the alkyl group have been replaced by the same or different halogen atoms.

The term "haloalkoxy" denotes an alkoxy group wherein at least one of the hydrogen atoms of the alkoxy group has been replaced by same or different halogen atoms, particularly fluoro atoms. "$C_1$-$C_7$-haloalkyl" denotes a $C_1$-$C_7$ alkoxy group in which at least one of the hydrogen atoms has been replaced by same or different halogen atoms. Examples of haloalkoxy include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, and trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. "$C_1$-$C_7$-hydroxyalkyl" denotes a $C_1$-$C_7$ alkyl group in which at least one of the hydrogen atoms has been replaced by same or different hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl.

The term "heterocycloalkyl" denotes a monovalent saturated or partly unsaturated mono- or bicyclic ring system of 3 to 9 ring atoms, containing 1, 2, or 3 ring heteroatoms selected from N, O and S, the remaining ring atoms being carbon. In particular embodiments, heterocycloalkyl is a monovalent saturated monocyclic ring system of 4 to 7 ring atoms, containing 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, and oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, and 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, and dihydropyranyl.

The term "oxo" when referring to substituents on heterocycloalkyl means that an oxygen atom is attached to the heterocycloalkyl ring. Thereby, the "oxo" can can either replace two hydrogen atoms on a carbon atom, or it can simply be attached to sulfur, so that the sulfur exists in oxidized form, i.e. bearing one or two oxygens.

The term "aryl" denotes a monovalent aromatic carbocyclic mono- or bicyclic ring system containing 6 to 10 carbon ring atoms. Examples of aryl moieties include phenyl and naphthyl.

The term "heteroaryl" denotes a monovalent aromatic heterocyclic mono- or bicyclic ring system of 5 to 12 ring atoms, containing 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "optional" or "optionally" denotes that a subsequently described event or circumstance may but need not occur, and that the description includes instances where the event or circumstance occurs and instances in which it does not.

Compounds of formula (I) can form pharmaceutically acceptable salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid.

The term "pharmaceutically acceptable salts" refers to such salts. Compounds of formula (I) which comprise an acidic group, such as e.g. a COOH group, can further form salts with bases. Examples of such salts are alkaline, earth-alkaline and ammonium salts such as e.g. Na—, K—, Ca— and trimethylammonium salt. The term "pharmaceutically acceptable salts" also refers to such salts. Particular salts are those obtained by the addition of an acid.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The invention provides novel compounds of formula (I)

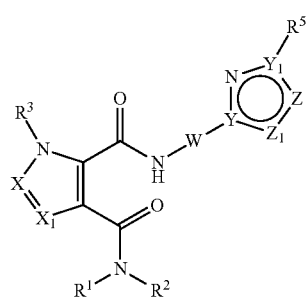

(I)

wherein:
X and $X_1$ are each independently $CR^4$ or N;
Y and $Y_1$ are each independently C or N;
Z and $Z_1$ are each independently $CR^6$, $NR^7$, N, O or S;
$R^1$ and $R^2$ are each independently selected from hydrogen, $C_1$-$C_7$-alkyl, $C_3$-$C_8$-cycloalkyl, $C_1$-$C_7$-haloalkyl, $C_1$-$C_7$-alkoxy-$C_1$-$C_7$-alkyl, heterocycloalkyl and $C_1$-$C_7$-alkyl optionally substituted by aryl or heteroaryl; or
$R^1$ and $R^2$, together with the nitrogen atom to which they are attached, form a bicyclic ring system or a heterocycloalkyl optionally substituted by 1 to 3 substituents independently selected from the group consisting of hydroxyl, halogen, $C_1$-$C_7$-alkyl, $C_1$-$C_7$-alkoxy, $C_1$-$C_7$-haloalkyl and oxo;
$R^3$ is hydrogen or $C_1$-$C_7$ alkyl;
$R^4$ is hydrogen, $C_1$-$C_7$ alkyl, $C_3$-$C_8$-cycloalkyl, $C_1$-$C_7$-haloalkyl or halogen;
$R^5$ is aryl or heteroaryl each of which is optionally substituted by $C_1$-$C_7$-alkyl, $C_3$-$C_8$-cycloalkyl, halogen, $C_1$-$C_7$ haloalkyl, $C_1$-$C_7$ alkoxy, hydroxyl, $C_1$-$C_7$ hydroxyalkyl, $C_1$-$C_7$ alkoxyalkyl, acetyl, cyano, or amino optionally substituted by one or two $C_1$-$C_7$ alkyl groups;
$R^6$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl or
$R^5$ and $R^6$, together with the $Y_1$ and Z atoms to which they are attached, form aryl or heteroaryl each of which isoptionally substituted by $C_1$-$C_7$ alkyl, halogen, $C_1$-$C_7$-alkoxy, $C_1$-$C_7$-haloalkyl;
$R^7$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, cycloalkyl or
$R^5$ and $R^7$, together with the $Y_1$ and Z atoms to which they are attached, form aryl or heteroaryl each of which is optionally substituted by $C_1$-$C_7$ alkyl, halogen, $C_1$-$C_7$-alkoxy, $C_1$-$C_7$-haloalkyl;
W is selected from ethylene or ethenylene each of which is optionally substituted by $C_1$-$C_7$ alkyl or halogen or W is N=CH—.

A particular embodiment of the present invention provides compounds of formula (I) as described above, wherein W is ethylene, optionally substituted by $C_1$-$C_7$ alkyl.

Another particular embodiment of the present invention provides compounds of formula (I) as described above, wherein $R^1$ and $R^2$, together with the nitrogen atom to which they are attached, form a 4, 5 or 6 membered heterocycloalkyl containing two heteroatoms selected from N and O, preferably azetidinyl or morpholinyl,
$R^3$ is hydrogen or methyl and
X is nitrogen and $X_1$ is $CR^4$, wherein $R^4$ is hydrogen.

Another particular embodiment of the present invention provides compounds of formula (I) as described above, wherein $R^1$ and $R^2$, together with the nitrogen atom to which they are attached, form a 4, 5 or 6 membered heterocycloalkyl containing two heteroatoms selected from N and O, preferably azetidinyl or morpholinyl,
$R^3$ is hydrogen or methyl and
X is $CR^4$, wherein $R^4$ is methyl or halogen and $X_1$ is nitrogen.

A particular embodiment of the present invention provides compounds of formula (I) as described above, wherein Y is C and $Y_1$ is C or N.

A particular embodiment of the present invention provides compounds of formula (I) as described above, wherein Y is N and $Y_1$ is C.

Yet another particular embodiment of the present invention provides compounds of formula (I) as described above, wherein Z is C and $Z_1$ is N or Z is N and $Z_1$ is C or O.

Another particular embodiment of the present invention provides compounds of formula (I) as described above, wherein $Y_1$ is C, Z is $CR^6$ or $NR^7$, wherein $R^5$ and $R^6$ or $R^5$ and $R^7$, together with $Y_1$ and Z to which they are attached, form heteroaryl selected from optionally substituted imidazopyridinyl and optionally substituted benzoimidazolyl.

Another particular embodiment of the present invention provides compounds of formula (I) as described above, wherein $R^5$ is selected from phenyl and pyridinyl, each of which is optionally substituted with halogen or $C_1$-$C_7$ alkoxy.

Yet another particular embodiment of the present invention provides compounds of formula (Ib)

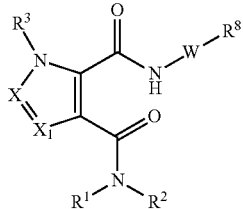

(Ib)

wherein $R^8$ is selected from the group consisting of:

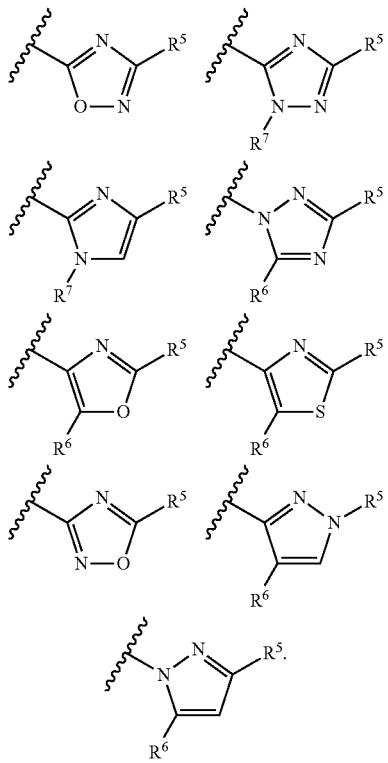

In another particular embodiment of the present invention provides compounds of formula (Ib) wherein $R^8$ is selected from the group consisting of:

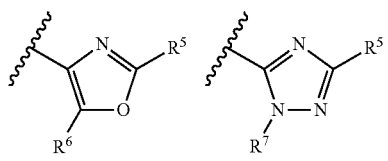

-continued

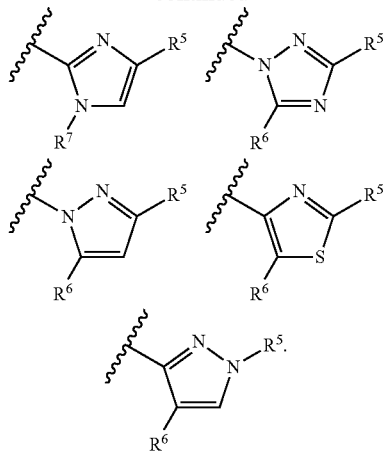

Another particular embodiment of the present invention provides compounds of formula (I) and (Ib) wherein $R^6$ is selected from hydrogen, $C_1$-$C_7$ alkyl and heteroaryl.

In a further particular embodiment the present invention provides compounds of formula (I) and (Ib) wherein $R^7$ is selected from hydrogen, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, and $C_1$-$C_7$-alkyl optionally substituted by aryl, heteroaryl, heterocycloalkyl, or $C_3$-$C_8$-cycloalkyl.

In another embodiment, the present invention provides compounds wherein $R^5$ is selected from phenyl and pyridinyl, each of which is optionally substituted with halogen or $C_1$-$C_7$ alkoxy.

Particular compounds of formula (I) are those selected from the group consisting of:
4-(Azetidine-1-carbonyl)-2-methyl-2H-pyrazole-3-carboxylic acid (2-imidazo[1,2-a]pyridin-2-yl-ethyl)-amide;
4-(Azetidine-1-carbonyl)-2-methyl-2H-pyrazole-3-carboxylic acid [2-(1-methyl-1H-benzoimidazol-2-yl)-ethyl]-amide;
4-(Azetidine-1-carbonyl)-2-methyl-2H-pyrazole-3-carboxylic acid [2-(3-phenyl-[1,2,4]oxadiazol-5-yl)-ethyl]-amide;
4-(Azetidine-1-carbonyl)-2-methyl-2H-pyrazole-3-carboxylic acid [2-(5-pyridin-3-yl-2H-[1,2,4]triazol-3-yl)-ethyl]-amide;
4-(Azetidine-1-carbonyl)-2-methyl-2H-pyrazole-3-carboxylic acid [2-(8-methyl-imidazo[1,2-a]pyridin-2-yl)-ethyl]-amide;
4-(Azetidine-1-carbonyl)-2-methyl-2H-pyrazole-3-carboxylic acid {2-[3-(4-chloro-phenyl)-[1,2,4]oxadiazol-5-yl]-ethyl}-amide;
4-(Azetidine-1-carbonyl)-2-methyl-2H-pyrazole-3-carboxylic acid [2-(1-methyl-4-phenyl-1H-imidazol-2-yl)-ethyl]-amide;
2,3-Dimethyl-5-(morpholine-4-carbonyl)-3H-imidazole-4-carboxylic acid [2-(1-methyl-1H-benzoimidazol-2-yl)-ethyl]-amide;
4-(Azetidine-1-carbonyl)-2-methyl-2H-pyrazole-3-carboxylic acid (2-benzothiazol-2-yl-ethyl)-amide;
5-(Azetidine-1-carbonyl)-3-methyl-3H-imidazole-4-carboxylic acid [2-(1-methyl-1H-benzoimidazol-2-yl)-ethyl]-amide;
4-(Azetidine-1-carbonyl)-2-methyl-2H-pyrazole-3-carboxylic acid [2-(1,5-dimethyl-1H-benzoimidazol-2-yl)-ethyl]-amide;

4-(Azetidine-1-carbonyl)-2-methyl-2H-pyrazole-3-carboxylic acid [2-(3-phenyl-pyrazol-1-yl)-ethyl]-amide;

5-(Azetidine-1-carbonyl)-2-chloro-3-methyl-3H-imidazole-4-carboxylic acid [2-(1-methyl-1H-benzoimidazol-2-yl)-ethyl]-amide;

4-(Azetidine-1-carbonyl)-2-methyl-2H-pyrazole-3-carboxylic acid [2-(5-pyridin-4-yl-2H-[1,2,4]triazol-3-yl)-ethyl]-amide;

4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide;

4-(Azetidine-1-carbonyl)-2-methyl-2H-pyrazole-3-carboxylic acid [2-(5-chloro-1-methyl-1H-benzoimidazol-2-yl)-ethyl]-amide;

4-(Azetidine-1-carbonyl)-2-methyl-2H-pyrazole-3-carboxylic acid [2-(2-methyl-5-pyridin-4-yl-2H-[1,2,4]triazol-3-yl)-ethyl]-amide;

4-(Azetidine-1-carbonyl)-2-methyl-2H-pyrazole-3-carboxylic acid [2-(3-phenyl-[1,2,4]triazol-1-yl)-ethyl]-amide;

4-(Azetidine-1-carbonyl)-2-methyl-2H-pyrazole-3-carboxylic acid [2-(2-phenyl-2H-[1,2,3]triazol-4-yl)-ethyl]-amide;

4-(Azetidine-1-carbonyl)-2-methyl-2H-pyrazole-3-carboxylic acid [2-(5-methyl-2-phenyl-oxazol-4-yl)-ethyl]-amide;

4-(Azetidine-1-carbonyl)-2-methyl-2H-pyrazole-3-carboxylic acid [2-(5-phenyl-[1,2,4]oxadiazol-3-yl)-ethyl]-amide;

4-(Azetidine-1-carbonyl)-2-methyl-2H-pyrazole-3-carboxylic acid [2-(2-methyl-5-phenyl-2H-[1,2,4]triazol-3-yl)-ethyl]-amide;

4-(Azetidine-1-carbonyl)-2-methyl-2H-pyrazole-3-carboxylic acid [1,1-dimethyl-2-(5-methyl-2-phenyl-oxazol-4-yl)-ethyl]-amide;

2-Methyl-4-(morpholine-4-carbonyl)-2H-pyrazole-3-carboxylic acid [2-(1-methyl-4-phenyl-1H-imidazol-2-yl)-ethyl]-amide;

4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide;

4-(Azetidine-1-carbonyl)-2-methyl-2H-pyrazole-3-carboxylic acid [2-(2-pyrimidin-2-yl-thiazol-4-yl)-ethyl]-amide;

4-(Azetidine-1-carbonyl)-2-methyl-2H-pyrazole-3-carboxylic acid [2-(1-methyl-4-pyridin-3-yl-1H-imidazol-2-yl)-ethyl]-amide;

4-(Azetidine-1-carbonyl)-2-methyl-2H-pyrazole-3-carboxylic acid [2-(1-phenyl-1H-pyrazol-3-yl)-ethyl]-amide;

4-(Azetidine-1-carbonyl)-2-methyl-2H-pyrazole-3-carboxylic acid [2-(2-phenyl-thiazol-4-yl)-ethyl]-amide;

4-(Azetidine-1-carbonyl)-2-methyl-2H-pyrazole-3-carboxylic acid {2-[4-(3-methoxy-phenyl)-1-methyl-1-imidazol-2-yl]-ethyl}-amide;

4-(Azetidine-1-carbonyl)-2-methyl-2H-pyrazole-3-carboxylic acid {2-[4-(2-methoxy-phenyl)-1-methyl-1-imidazol-2-yl]-ethyl}-amide;

4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide;

5-(Azetidine-1-carbonyl)-2,3-dimethyl-3H-imidazole-4-carboxylic acid [2-(1-methyl-4-phenyl-1H-imidazol-2-yl)-ethyl]-amide;

4-(Azetidine-1-carbonyl)-2-methyl-2H-pyrazole-3-carboxylic acid {2-[2-(2-methoxy-ethyl)-5-phenyl-2H-[1,2,4]triazol-3-yl]-ethyl}-amide;

4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide;

4-(Azetidine-1-carbonyl)-2-methyl-2H-pyrazole-3-carboxylic acid [2-(5-phenyl-2H-[1,2,4]triazol-3-yl)-ethyl]-amide;

2-Methyl-4-(morpholine-4-carbonyl)-2H-pyrazole-3-carboxylic acid [2-(5-methyl-2-phenyl-oxazol-4-yl)-ethyl]-amide;

2-Methyl-4-(pyrrolidine-1-carbonyl)-2H-pyrazole-3-carboxylic acid [2-(5-methyl-2-phenyl-oxazol-4-yl)-ethyl]-amide;

4-(3-Fluoro-azetidine-1-carbonyl)-2-methyl-2H-pyrazole-3-carboxylic acid [2-(5-methyl-2-phenyl-oxazol-4-yl)-ethyl]-amide;

2-Methyl-2H-pyrazole-3,4-dicarboxylic acid 4-(cyclopropyl-methyl-amide) 3-{[2-(5-methyl-2-phenyl-oxazol-4-yl)-ethyl]-amide};

2-Methyl-4-(2-oxa-6-aza-spiro[3.3]heptane-6-carbonyl)-2H-pyrazole-3-carboxylic acid [2-(5-methyl-2-phenyl-oxazol-4-yl)-ethyl]-amide;

2-Methyl-4-(thiomorpholine-4-carbonyl)-2H-pyrazole-3-carboxylic acid [2-(5-methyl-2-phenyl-oxazol-4-yl)-ethyl]-amide;

4-(Azetidine-1-carbonyl)-2-methyl-2H-pyrazole-3-carboxylic acid [2-(5-methyl-2-phenyl-thiazol-4-yl)-ethyl]-amide;

4-(Azetidine-1-carbonyl)-2-methyl-2H-pyrazole-3-carboxylic acid [2-(5-methyl-3-phenyl-[1,2,4]triazol-1-yl)-ethyl]-amide;

4-(Azetidine-1-carbonyl)-2-methyl-2H-pyrazole-3-carboxylic acid [2-(2-benzyl-5-phenyl-2H-[1,2,4]triazol-3-yl)-ethyl]-amide;

4-(Azetidine-1-carbonyl)-2-methyl-2H-pyrazole-3-carboxylic acid [2-(5-methyl-2-p-tolyl-thiazol-4-yl)-ethyl]-amide;

4-(Azetidine-1-carbonyl)-2-methyl-2H-pyrazole-3-carboxylic acid [2-(4-methyl-1-phenyl-1H-pyrazol-3-yl)-ethyl]-amide;

4-(Azetidine-1-carbonyl)-2-methyl-2H-pyrazole-3-carboxylic acid {2-[2-(2-ethyl-pyridin-4-yl)-5-methyl-thiazol-4-yl]-ethyl}-amide;

4-(Azetidine-1-carbonyl)-2-methyl-2H-pyrazole-3-carboxylic acid {2-[5-phenyl-2-(2,2,2-trifluoro-ethyl)-2H-[1,2,4]triazol-3-yl]-ethyl}-amide;

2-Methyl-4-(morpholine-4-carbonyl)-2H-pyrazole-3-carboxylic acid [2-(1-methyl-1H-benzoimidazol-2-yl)-ethyl]-amide;

2-Methyl-4-(pyrrolidine-1-carbonyl)-2H-pyrazole-3-carboxylic acid [2-(1-methyl-1H-benzoimidazol-2-yl)-ethyl]-amide;

5-(Azetidine-1-carbonyl)-3-methyl-3H-[1,2,3]triazole-4-carboxylic acid [2-(1-methyl-4-phenyl-1-imidazol-2-yl)-ethyl]-amide;

2-Methyl-2H-pyrazole-3,4-dicarboxylic acid 4-(cyclopropyl-methyl-amide) 3-{[2-(1-methyl-1H-benzoimidazol-2-yl)-ethyl]-amide};

4-(Azetidine-1-carbonyl)-2-methyl-2H-pyrazole-3-carboxylic acid [2-(5-methyl-4-phenyl-thiazol-2-yl)-ethyl]-amide;

4-(Azetidine-1-carbonyl)-2-methyl-2H-pyrazole-3-carboxylic acid [2-(2,5-diphenyl-2H-[1,2,4]triazol-3-yl)-ethyl]-amide;
4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide;
4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide;
4-(Azetidine-1-carbonyl)-2-methyl-2H-pyrazole-3-carboxylic acid [2-(2,5-diphenyl-oxazol-4-yl)-ethyl]-amide;
4-(Azetidine-1-carbonyl)-2-methyl-2H-pyrazole-3-carboxylic acid [2-(5-phenyl-2-pyridin-3-yl-2H-[1,2,4]triazol-3-yl)-ethyl]-amide;
4-(Azetidine-1-carbonyl)-2-methyl-2H-pyrazole-3-carboxylic acid {2-[5-(3-fluoro-phenyl)-2-phenyl-2H-[1,2,4]triazol-3-yl]-ethyl}-amide;
2-Methyl-2H-pyrazole-3,4-dicarboxylic acid 4-(cyclopentyl-methyl-amide) 3-{[2-(1-methyl-4-phenyl-1H-imidazol-2-yl)-ethyl]-amide};
2-Methyl-2H-pyrazole-3,4-dicarboxylic acid 4-(cyclobutyl-methyl-amide) 3-{[2-(1-methyl-4-phenyl-1H-imidazol-2-yl)-ethyl]-amide};
5-(Azetidine-1-carbonyl)-3-methyl-2-trifluoromethyl-3H-imidazole-4-carboxylic acid [2-(1-methyl-4-phenyl-1H-imidazol-2-yl)-ethyl]-amide;
4-(Azetidine-1-carbonyl)-2-methyl-2H-pyrazole-3-carboxylic acid (2-[1,2,4]triazolo[1,5-a]pyridin-2-yl-ethyl)-amide;
4-(Azetidine-1-carbonyl)-2-methyl-2H-pyrazole-3-carboxylic acid [2-(2-phenyl-5-pyridin-3-yl-oxazol-4-yl)-ethyl]-amide.

Yet particular compounds of formula (I) are those selected from the group consisting of:
4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide;
4-(Azetidine-1-carbonyl)-2-methyl-2H-pyrazole-3-carboxylic acid [2-(1-methyl-4-pyridin-3-yl-1H-imidazol-2-yl)-ethyl]-amide;
4-(Azetidine-1-carbonyl)-2-methyl-2H-pyrazole-3-carboxylic acid [2-(2-methyl-5-phenyl-2H-[1,2,4]triazol-3-yl)-ethyl]-amide;
4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide;
4-(Azetidine-1-carbonyl)-2-methyl-2H-pyrazole-3-carboxylic acid [2-(5-chloro-1-methyl-1H-benzoimidazol-2-yl)-ethyl]-amide;
4-(Azetidine-1-carbonyl)-2-methyl-2H-pyrazole-3-carboxylic acid [2-(2-methyl-5-pyridin-4-yl-2H-[1,2,4]triazol-3-yl)-ethyl]-amide;
4-(Azetidine-1-carbonyl)-2-methyl-2H-pyrazole-3-carboxylic acid [2-(2-phenyl-2H-[1,2,3]triazol-4-yl)-ethyl]-amide;
4-(Azetidine-1-carbonyl)-2-methyl-2H-pyrazole-3-carboxylic acid [2-(5-phenyl-[1,2,4]oxadiazol-3-yl)-ethyl]-amide;
4-(Azetidine-1-carbonyl)-2-methyl-2H-pyrazole-3-carboxylic acid [1,1-dimethyl-2-(5-methyl-2-phenyl-oxazol-4-yl)-ethyl]-amide;
4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide;
4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide;
4-(Azetidine-1-carbonyl)-2-methyl-2H-pyrazole-3-carboxylic acid [2-(2,5-diphenyl-2H-[1,2,4]triazol-3-yl)-ethyl]-amide;
4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide;
4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide;
4-(Azetidine-1-carbonyl)-2-methyl-2H-pyrazole-3-carboxylic acid [2-(5-phenyl-2-pyridin-3-yl-2H-[1,2,4]triazol-3-yl)-ethyl]-amide;
2-Methyl-2H-pyrazole-3,4-dicarboxylic acid 4-(cyclobutyl-methyl-amide) 3-{[2-(1-methyl-4-phenyl-1H-imidazol-2-yl)-ethyl]-amide}.

The present invention further provides a process for the manufacture of a compound of formula (I) as defined above which process comprises reacting a compound of formula (II)

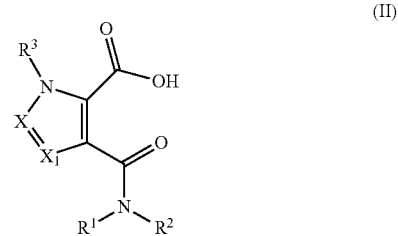

with a compound of formula (III)

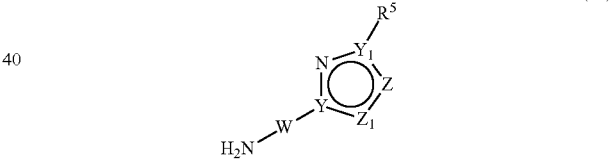

wherein $R^1$, $R^2$, $R^3$, $R^5$, W, X, $X_1$, Y, $Y_1$, Z and $Z_1$ are as defined above.

The reaction of a compound of formula (II) with a compound of formula (III) can be carried out under conditions as described in the examples or under conditions well known to the person skilled in the art. For example, the reaction can be performed in solvents like dimethylformamide (DMF), tetrahydrofurane (THF), dioxane, dichloromethane, ethyl acetate, 1-methyl-2-pyrrolidone (NMP) and the like at temperatures in the range of e.g. at −10-120° C., but typically at 0° C.—room temperature, at atmospheric pressure or elevated pressure. The reaction can be carried out in one step or in several steps. If the reaction is carried out in one step, the conversion is usually accomplished with a coupling reagent, such as N,N'-dicyclohexylcarbodiimide (DCC), N-(3-dimethylaminopropyl)-N'-ethylcarbodiimide hydrochloride (EDC), O-(benzotriazol-1-yl)-N,N,N',N'-tetramethyluronium tetrafluoroborate (TBTU), O-(7-azabenzotriazol-1-yl)-

N,N,N',N'-tetramethyluronium hexafluorophosphate (HATU), (1-cyano-2-ethoxy-2-oxoethylidenaminooxy)dimethylamino-morpholino-carbenium hexafluorophosphate (COMU), propylphosphonic anhydride, and the like (a large number of chemically diverse coupling reagents are described in the literature). If the reaction is carried out in several steps, the acid (II) is usually transformed into a reactive species such as an acid chloride or an acid anhydride, for instance by reaction with thionyl chloride, sulphuryl chloride, phosphoroxychloride, oxalylchloride, or the like, with or without a solvent such as dichloromethane, with or without an additive such as DMF. This reactive species is then converted in another step by addition of the amine (III) into the product (I). The second step is typically carried out in a solvent such as dimethylformamide (DMF), tetrahydrofurane (THF), dioxane, dichloromethane, ethyl acetate, 1-methyl-2-pyrolidone (NMP) and the like at temperatures in the range of e.g. at −10-120° C., but typically at 0°—room temperature, at atmospheric pressure or elevated pressure. It is often advantageous to add a base, such as triethylamine or diisopropylethylamine, to the reaction mixture.

The compounds of formula (II) and (III) can be prepared by methods known in the art or as described below or in analogy thereto. Unless otherwise indicated, $R^1$, $R^2$, $R^3$, $R^5$, W, X, $X_1$, Y, $Y_1$, Z and $Z_1$ are as defined above.

General Synthesis Procedures

Compounds of formula (I) can be prepared from building blocks (II) and (III) according to Scheme 1. The conversion, commonly known as amide coupling, can be achieved in several ways. In one method, the acid (II) is activated with a coupling reagent, such as 2-(1H-benzotriazole-1-yl)-1,1,3,3-tetramethyluronium tetrafluoroborate (TBTU), and converted by addition of amine (III) to the desired product (I). In another method, the acid (II) is activated by transformation into an acid chloride, e.g. by reaction with thionyl chloride. The acid chloride is then converted by addition of the amine (III) to the desired product (I). A base, e.g. diisopropylethylamine (DIPEA), is usually added to bind liberated HCl.

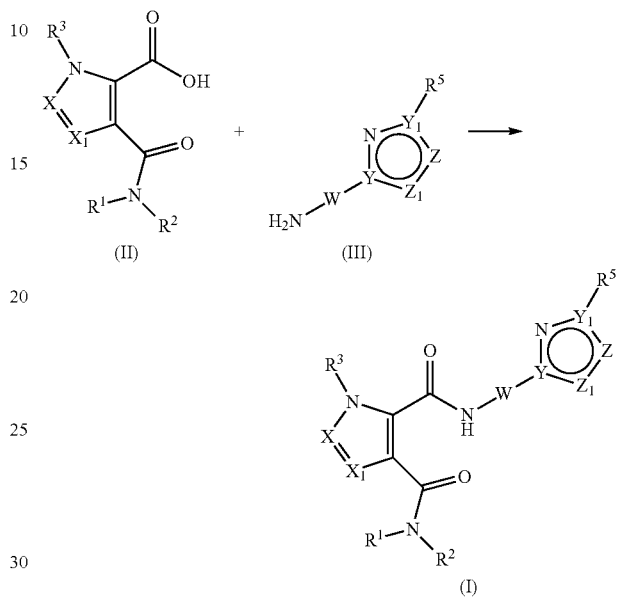

Scheme 1

Compounds of formula (I) having a pyrazole dicarboxylate core (X=N, $X_1$=CR$^4$) can be prepared according to Scheme 2 by the following transformations in close analogy to known procedures.

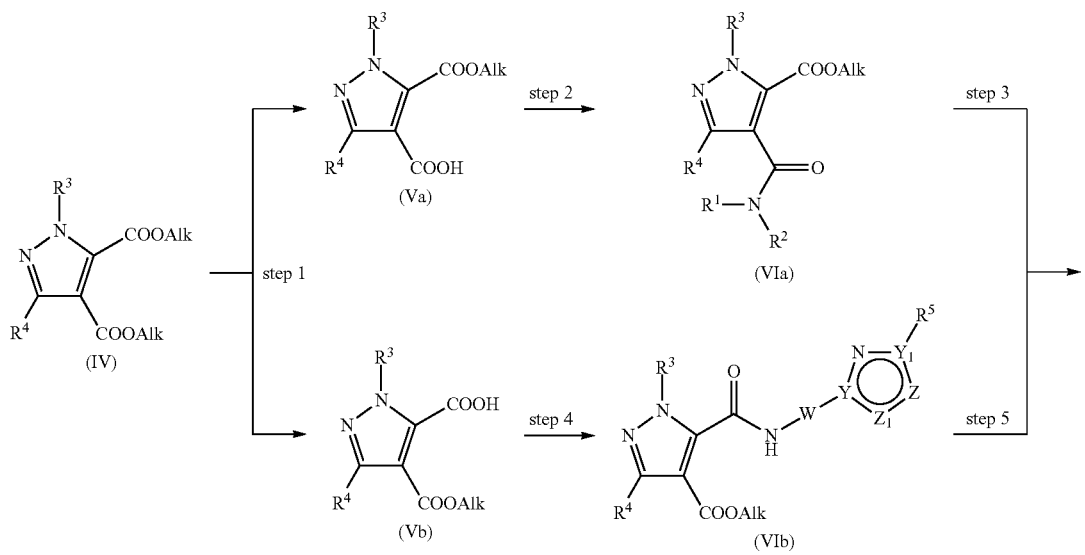

Scheme 2

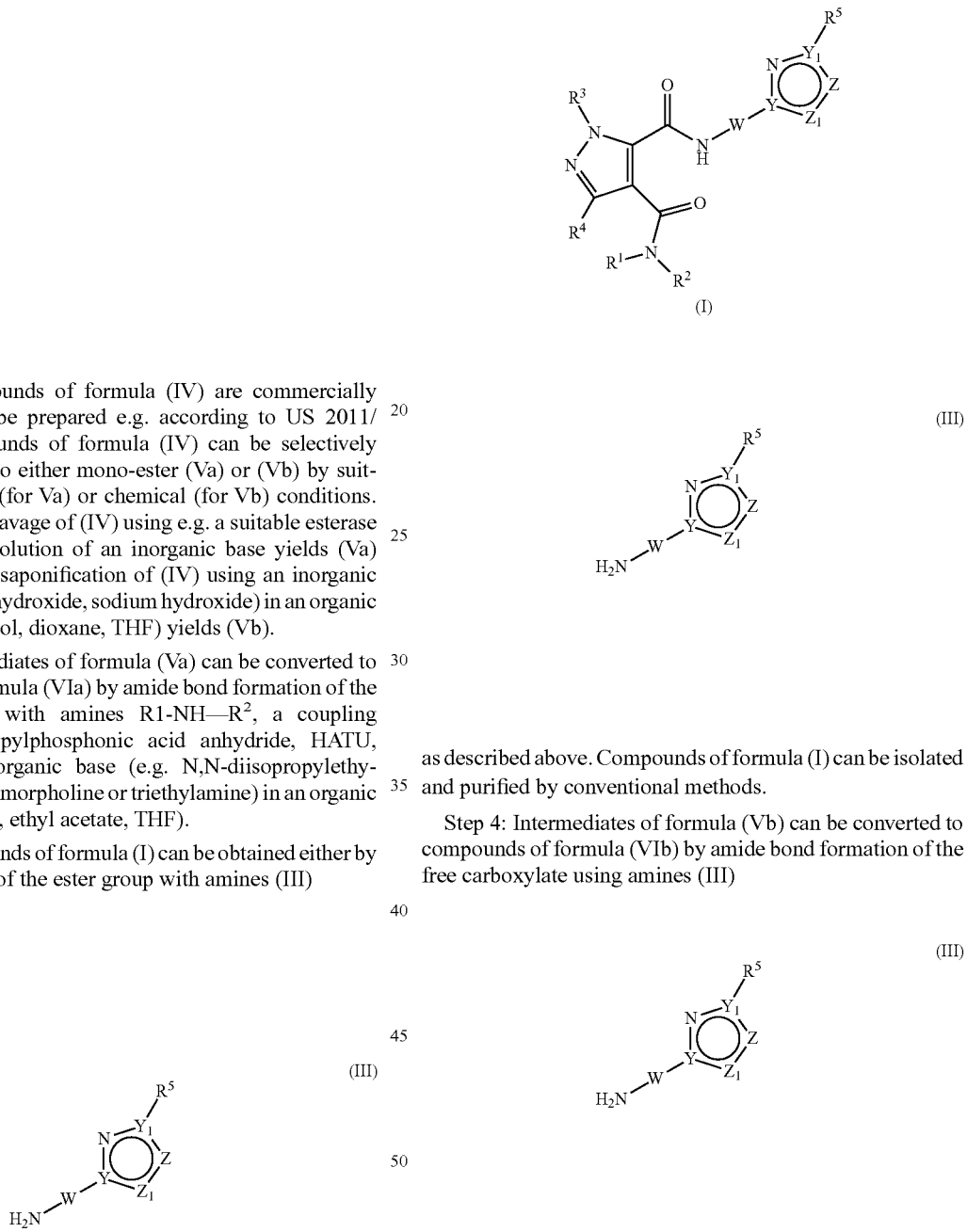

Step 1: Compounds of formula (IV) are commercially available or can be prepared e.g. according to US 2011/0071128. Compounds of formula (IV) can be selectively mono-saponified to either mono-ester (Va) or (Vb) by suitable biochemical (for Va) or chemical (for Vb) conditions. The enzymatic cleavage of (IV) using e.g. a suitable esterase and an aqueous solution of an inorganic base yields (Va) whereas classical saponification of (IV) using an inorganic base (e.g. lithium hydroxide, sodium hydroxide) in an organic solvent (e.g. ethanol, dioxane, THF) yields (Vb).

Step 2: Intermediates of formula (Va) can be converted to compounds of formula (VIa) by amide bond formation of the free carboxylate with amines R1-NH—$R^2$, a coupling reagent (e.g. propylphosphonic acid anhydride, HATU, TBTU) and an organic base (e.g. N,N-diisopropylethylamine, N-methyl-morpholine or triethylamine) in an organic solvent (e.g. DMF, ethyl acetate, THF).

Step 3: Compounds of formula (I) can be obtained either by direct aminolysis of the ester group with amines (III) and a Lewis acid (e.g. trimethylaluminium or dimethylaluminium chloride) in an organic solvent (e.g. toluene or dioxane) or by saponification of (VIa) as described above for (Vb) and subsequent amide bond formation of the free carboxylate with amines (III) as described above. Compounds of formula (I) can be isolated and purified by conventional methods.

Step 4: Intermediates of formula (Vb) can be converted to compounds of formula (VIb) by amide bond formation of the free carboxylate using amines (III) as described above.

Step 5: Compounds of formula (I) can be obtained either by direct aminolysis of the ester group of (VIb) with amines R1-NH—$R^2$ as described above or by saponification of (VIb) as described above for (Vb) and subsequent amide bond formation of the free carboxylate with amines R1-NH—$R^2$ as described above. The compound of formula (I) can be isolated and purified by conventional methods.

Compounds of formula (I) having a triazole dicarboxylate core (X and X1=N) can be prepared according to Scheme 3 by the following transformations in close analogy to known procedures.

Scheme 3

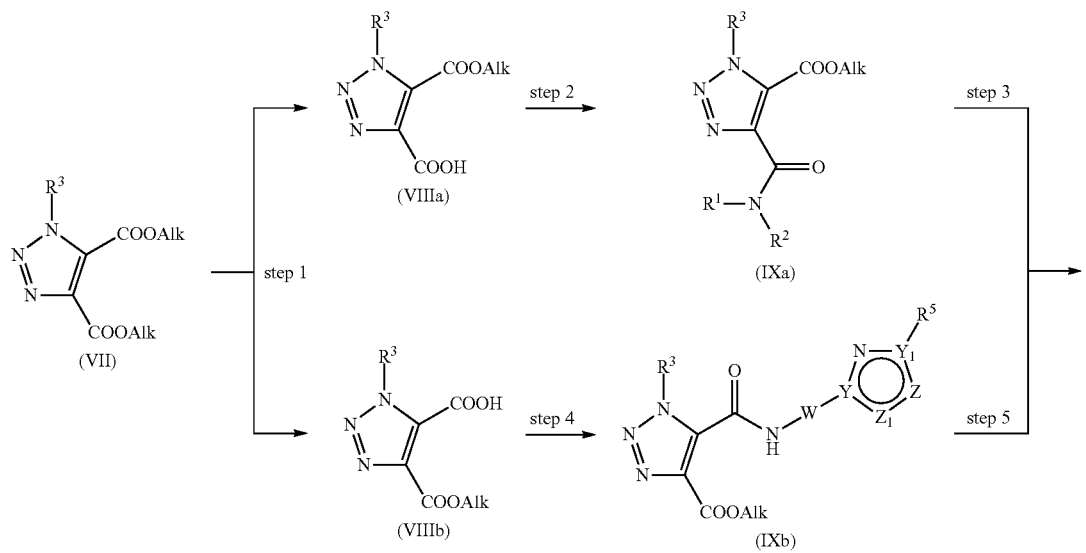

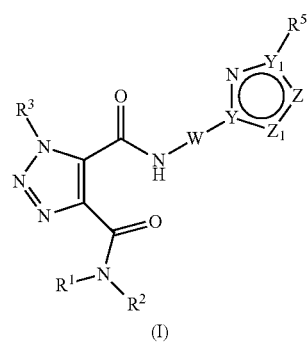

Compounds of formula (VII) are commercially available or can be prepared e.g. according to Chem. Lett. 1983, 1131 or J. Heterocycl. Chem. 2002, 39, 889. Compounds of formula (VII) can be transformed into compounds of formula (I) by the same procedures (step 1 step 5) as described above for transformations starting from compounds of formula (IV).

Compounds of formula (I) having a imidazole dicarboxylate core ($X=CR^4$, $X_1=N$) can be prepared according to Scheme 4 by the following transformations in close analogy to known procedures.

Scheme 4

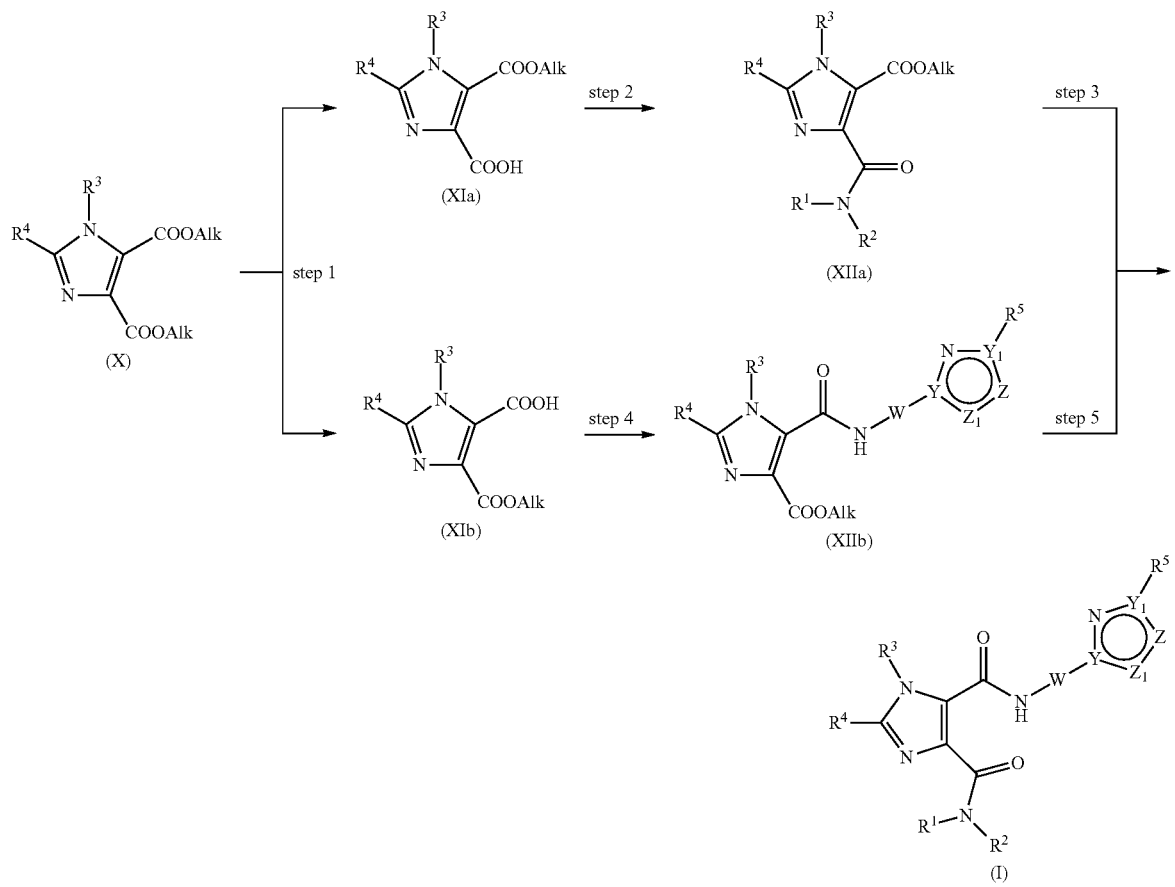

Compounds of formula (X) are commercially available or can be prepared from commercially available precursors (imidazole-4,5-dicarboxylate) or according to e.g. J. Med. Chem. 1989, 32, 119 (2-methyl-imidazole-4,5-dicarboxylate). Compounds of formula (X) can be transformed into compounds of formula (I) by the same procedures (step 1-step 5) as described above for transformations starting from compounds of formula (IV).

All reactions are typically performed in a suitable solvent and under an atmosphere of argon or nitrogen.

The invention further provides methods for the use of compounds of formula (I) as defined above as therapeutically active substance.

The invention further provides a pharmaceutical composition having compounds of formula (I) as defined above and a therapeutically inert carrier.

As described above, the novel compounds of the present invention inhibit PDE10A activity. The compounds of the present invention can therefore be used, either alone or in combination with other drugs, for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

Yet in another embodiment, the invention provides methods for the use of a compound of the present invention for the preparation of a medicament for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The invention also provides a compound as described above for the treatment or prophylaxis of psychotic disorders, schizophrenia, positive, negative and/or cognitive symptoms associated with schizophrenia, delusional disorder, substance-induced psychotic disorder, anxiety disorders, panic disorder, obsessive/compulsive disorders, acute stress disorder, generalized anxiety disorder, drug addictions, movement disorders, Parkinson's disease, restless leg syndrome, cognition deficiency disorders, Alzheimer's disease, multi-infarct dementia, mood disorders, depression, bipolar disorders, neuropsychiatric conditions, psychosis, attention-deficit/hyperactivity disorder, attentional disorders, diabetes and related disorders, type 2 diabetes mellitus, neurodegenerative disorders, Huntington's disease, multiple sclerosis, stroke, spinal cord injury, solid tumors, hematological malignancies, renal cell carcinoma or breast cancer.

The compounds of formula (I) can have one or more asymmetric C atoms and can therefore exist as an enantiomeric mixture, mixture of stereoisomers or as optically pure compounds. The compounds of formula (I) include all diastereomers, tautomers, racemates and mixtures thereof.

Particular compounds of formula (I) are described in the examples as individual compounds as well as pharmaceutically acceptable salts as well as pharmaceutically acceptable esters thereof. Furthermore, the substituents as found in the specific examples described below, individually constitute particular embodiments of the present invention.

Pharmaceutical Compositions and Administration

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) can be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound can be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit PDE10 and to control the cAMP signaling pathway. For example, such amount can be below the amount that is toxic to normal cells, or the mammal as a whole.

In one example, the pharmaceutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, preferably contain from about 25-100 mg of the compound of the invention.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 mg, 50 mg, 100 mg, 250 mg, or 500 mg of the compound of the invention compounded with about 90-30 mg anhydrous lactose, about 5-40 mg sodium croscarmellose, about 5-30 mg polyvinylpyrrolidone (PVP) K30, and about 1-10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5-400 mg, of the invention in a suitable buffer solution, e.g. a phosphate buffer, adding a tonicifier, e.g. a salt such sodium chloride, if desired. The solution can be filtered, e.g., using a 0.2 micron filter, to remove impurities and contaminants.

An embodiment, therefore, includes a pharmaceutical composition containing a compound of formula (I), or a stereoisomer or pharmaceutically acceptable salt thereof. In a further embodiment includes a pharmaceutical composition containing a compound of formula (I), or a stereoisomer or pharmaceutically acceptable salt thereof, together with a pharmaceutically acceptable carrier or excipient.

The following test was carried out in order to determine the activity of the compounds of the present invention. PDE10 activity of the compounds of the present invention was determined using a Scintillation Proximity Assay (SPA)-based method similar to the one previously described (Fawcett, L. et al., Proc Natl Acad Sci USA (2000) 97(7):3702-3707).

The human PDE10A full length assay was performed in 96-well micro titer plates. The reaction mixture of 50 µl contained 20 mM HEPES pH=7.5/10 mM $MgCl_2$/0.05 mg/ml BSA (Sigma cat. #A-7906), 50 nM cGMP (Sigma, cat. # G6129) and 50 nM [3H]-cGMP (GE Healthcare, cat. # TRK392 S.A. 13.2 Ci/mmol), 3.75 ng/well PDE10A enzyme (Enzo Life Science, Lausen, Switzerland cat #SE-534) with or without a specific test compound. A range of concentrations of the potential inhibitor was used to generate data for calculating the concentration of inhibitor resulting in 50% of the effect (e.g. IC50, the concentration of the competitor inhibiting PDE10A activity by 50%). Non-specific activity was tested without the enzyme. The reaction was initiated by the addition of the substrate solution (cGMP and [3H]-cGMP) and allowed to progress for 20 minutes at room temperature. The reaction was terminated by adding 25 μl of YSi—SPA scintillation beads (GE Healthcare, cat. # RPNQ0150) in 18 mM zinc sulphate solution (stop reagent). After 1 h under shaking, the plate was centrifuged one minute at 170 g to allow beads to settle. Afterwards, radioactive counts were measured on a Perkin Elmer TopCount Scintillation plate reader.

The compounds according to formula (I) have an IC50 value below 10 μM, more specifically below 5 μM, yet more specifically below 1 μM. The following table 1 shows data for some examples.

TABLE 1

| Example | PDE10A inhibition IC50 [nM] |
|---|---|
| 1 | 86.6 |
| 2 | 16.0 |
| 3 | 64.0 |
| 4 | 13.4 |
| 5 | 417.7 |
| 6 | 399.9 |
| 7 | 4.0 |
| 8 | 1085.4 |
| 9 | 189.4 |
| 10 | 2251.3 |
| 11 | 34.5 |
| 12 | 73.0 |
| 13 | 658.7 |
| 14 | 714.3 |
| 15 | 207.2 |
| 16 | 20.5 |
| 17 | 1437.7 |
| 18 | 110.0 |
| 19 | 225.3 |
| 20 | 14.5 |
| 21 | 202.3 |
| 22 | 21.3 |
| 23 | 77.9 |
| 24 | 12.4 |
| 25 | 763.4 |
| 26 | 23.8 |
| 27 | 11.0 |
| 28 | 19.3 |
| 29 | 32.8 |
| 30 | 38.5 |
| 31 | 1.7 |
| 32 | 3.1 |
| 33 | 86.0 |
| 34 | 303.9 |
| 35 | 5.66 |
| 36 | 3.77 |
| 37 | 45.89 |
| 38 | 27.28 |
| 39 | 18.46 |
| 40 | 13.81 |
| 41 | 236.51 |
| 42 | 259.58 |
| 43 | 16.8 |
| 44 | 135.6 |
| 45 | 3.7 |
| 46 | 660.76 |
| 47 | 14.51 |
| 48 | 372.76 |
| 49 | 44.88 |
| 50 | 402.23 |

TABLE 1-continued

| Example | PDE10A inhibition IC50 [nM] |
|---|---|
| 51 | 145.14 |
| 52 | 73.66 |
| 53 | 31 |
| 54 | 179.89 |
| 55 | 0.39 |
| 56 | 3.41 |
| 57 | 0.47 |
| 58 | 0.7 |
| 59 | 0.53 |
| 60 | 0.67 |
| 61 | 54.22 |
| 62 | 7.41 |
| 63 | 56.92 |
| 64 | 258.02 |
| 65 | 1.83 |

The following examples serve to illustrate the present invention in more detail. They are, however, not intended to limit its scope in any manner Experimental Procedures In the schemes above and in the following preparative examples, the following abbreviations have been used: h—hour(s), min minute(s), RT—room temperature.

Intermediates

Intermediate A-1: 4-(Azetidine-1-carbonyl)-2-methyl-2H-pyrazole-3-carboxylic acid

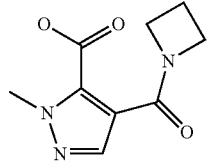

Intermediate A-1 was prepared as described in US 2011/0071128, example 74, steps 1-3

Intermediate A-2: 2-Methyl-4-(morpholine-4-carbonyl)-2H-pyrazole-3-carboxylic acid

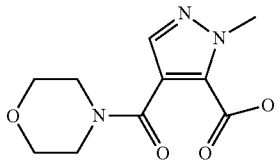 [SMILES: Cn1ncc(C(=O)N2CCOCC2)c1C(=O)O]

Intermediate A-2 was prepared according to US 2011/0071128, example 74, steps 1-3 using morpholine instead of azetidine in step 2.

EXAMPLES

Example 1

4-(Azetidine-1-carbonyl)-2-methyl-2H-pyrazole-3-carboxylic acid (2-imidazo[1,2-a]pyridin-2-yl-ethyl)-amide

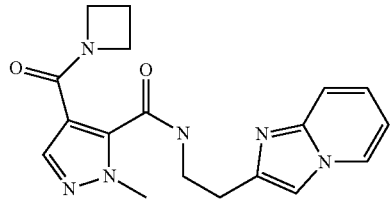 [SMILES: Cn1ncc(C(=O)N2CCC2)c1C(=O)NCCc1cn2ccccc2n1]

A mixture of intermediate A-1 (32 mg, 153 μmol), 2-(imidazo[1,2-a]pyridin-2-yl)ethanamine dihydrochloride (46.7 mg, 199 μmol), O-(7-azabenzotriazol-1-yl)-N,N,N',N'-tetramethyluronium hexafluorophosphate (HATU; 64.1 mg, 169 μmol) and N-methylmorpholine (84.3 μL, 767 μmol) in THF (1.5 mL) was heated under nitrogen atmosphere at 70° C. for 16 hr. The reaction mixture was cooled to RT, poured into ethyl acetate (50 mL) and extracted with water (2×15 mL). The organic phase was washed with brine (15 mL) and the aqueous layers were back-extracted with ethyl acetate (1×50 mL). The organic layers were dried over MgSO4 and concentrated in vacuo. The crude material was purified by flash chromatography (using silica gel and a MeOH/ethyl acetate gradient) to give the title compound (18 mg, 51.1 μmol, 33.3%) as colorless solid. MS: M=353.2 (M+H)+

Example 2

4-(Azetidine-1-carbonyl)-2-methyl-2H-pyrazole-3-carboxylic acid [2-(1-methyl-1H-benzoimidazol-2-yl)-ethyl]-amide

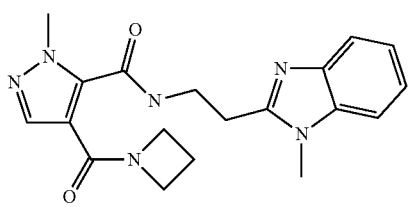 [SMILES: Cn1ncc(C(=O)N2CCC2)c1C(=O)NCCc1nc2ccccc2n1C]

The product was obtained starting from intermediate A-1 (32 mg, 153 μmol) and 2-(1-methyl-1H-benzo[d]imidazol-2-yl)ethanamine (34.9 mg, 199 μmol) according to the method described in example 1 as colorless solid (19.4 mg, 52.9 μmol, 34.5%). MS: M=367.2 (M+H)+

Example 3

4-(Azetidine-1-carbonyl)-2-methyl-2H-pyrazole-3-carboxylic acid [2-(3-phenyl-[1,2,4]oxadiazol-5-yl)-ethyl]-amide

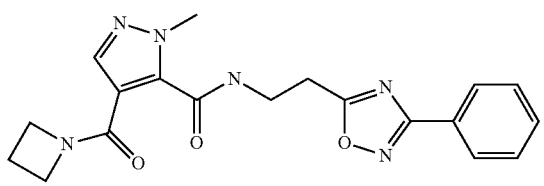 [SMILES: Cn1ncc(C(=O)N2CCC2)c1C(=O)NCCc1nc(-c2ccccc2)no1]

The product was obtained starting from intermediate A-1 (32 mg, 153 μmol) and 2-(3-phenyl-1,2,4-oxadiazol-5-yl)ethanamine (37.7 mg, 199 μmol) according to the method described in example 1 after purification by preparative HPLC using an acetonitrile/water (containing 0.1% formic acid) gradient as colorless solid (26 mg, 68.3 μmol, 44.6%). MS: M=381.3 (M+H)+

Example 4

4-(Azetidine-1-carbonyl)-2-methyl-2H-pyrazole-3-carboxylic acid [2-(5-pyridin-3-yl-2H-[1,2,4]triazol-3-yl)-ethyl]-amide

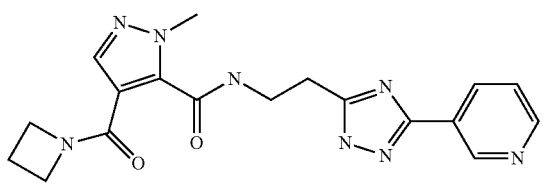 [SMILES: Cn1ncc(C(=O)N2CCC2)c1C(=O)NCCc1nc(-c2cccnc2)n[nH]1]

The product was obtained starting from intermediate A-1 (32 mg, 153 μmol) and 2-(3-(pyridin-3-yl)-1H-1,2,4-triazol-5-yl)ethanamine dihydrochloride (55.0 mg, 199 μmol) according to the method described in example 1 after trituration of the crude product with ethyl acetate as light brown solid (17 mg, 44.7 μmol, 29.1%). MS: M=381.3 (M+H)+

Example 5

4-(Azetidine-1-carbonyl)-2-methyl-2H-pyrazole-3-carboxylic acid [2-(8-methyl-imidazo[1,2-a]pyridin-2-yl)-ethyl]-amide

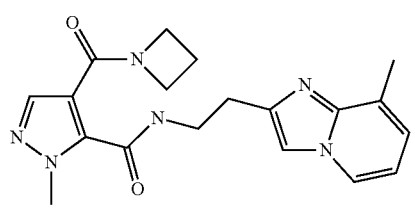 [SMILES: Cc1cccn2cc(CCNC(=O)c3c(C(=O)N4CCC4)cnn3C)nc12]

The product was obtained starting from intermediate A-1 (32 mg, 153 µmol) and 2-(8-methylimidazo[1,2-a]pyridin-2-yl)ethanamine (34.9 mg, 199 µmol) according to the method described in example 1 as light yellow solid (15 mg, 26.7%). MS: M=367.4 (M+H)+

Example 6

4-(Azetidine-1-carbonyl)-2-methyl-2H-pyrazole-3-carboxylic acid {2-[3-(4-chloro-phenyl)-[1,2,4]oxadiazol-5-yl]-ethyl}-amide

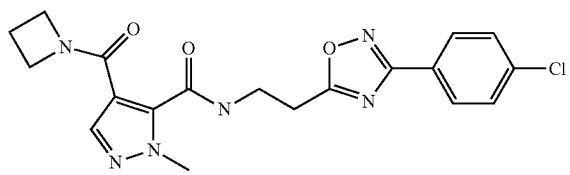 [SMILES: Cn1ncc(C(=O)N2CCC2)c1C(=O)NCCc1nc(-c2ccc(Cl)cc2)no1]

The product was obtained starting from intermediate A-1 (32 mg, 153 µmol), 2-(3-(4-chlorophenyl)-1,2,4-oxadiazol-5-yl)ethanamine (44.6 mg, 199 µmol) according to the method described in example 3 as colorless solid (9 mg, 21.7 µmol, 14.1%). MS: M=415.3 (M+H)+

Example 7

4-(Azetidine-1-carbonyl)-2-methyl-2H-pyrazole-3-carboxylic acid [2-(1-methyl-4-phenyl-1-imidazol-2-yl)-ethyl]-amide

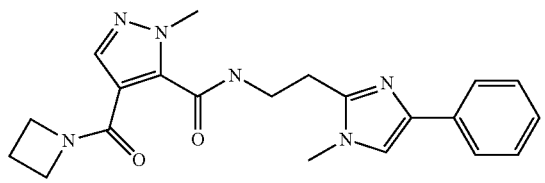 [SMILES: Cn1cc(-c2ccccc2)nc1CCNC(=O)c1c(C(=O)N2CCC2)cnn1C]

Step 1: 2-Oxo-2-phenylethyl 3-(tert-butoxycarbonylamino)propanoate

To a solution of 3-(tert-butoxycarbonylamino)propanoic acid (1 g, 5.29 mmol) in EtOH (20 mL) was added cesium carbonate (861 mg, 2.64 mmol) and the reaction mixture was stirred at 20° C. for 1 h. The solvent was removed in vacuo and the residue was dissolved in DMF (20.0 mL). 2-Bromo-1-phenylethanone (1.05 g, 5.29 mmol) was added and the reaction mixture was stirred at 20° C. for 4 h. The solvent was removed in vacuo and the crude product was dissolved in ethyl acetate (20 mL). Cesium bromide was filtered off and washed twice with ethyl acetate (10 mL). The filtrate was evaporated and dried in vacuo to give the product as colorless semisolid material (2.02 g, 5.26 mmol, 99.4%). MS: M=208.1 (M-Boc+H)+

Step 2: tert-Butyl 2-(4-phenyl-1H-imidazol-2-yl)ethylcarbamate

To a solution of 2-oxo-2-phenylethyl 3-(tert-butoxycarbonylamino)-propanoate (1.954 g, 5.09 mmol) in xylene (15 mL) was added ammonium acetate (7.84 g, 102 mmol). The reaction mixture was heated to 140° C. (strong bubbling) and stirred for 1.5 h. The reaction mixture was poured into saturated sodium bicarbonate solution (20 mL, gas evolution, pH=7) and extracted with ethyl acetate (2×40 mL). The organic layers were washed with saturated sodium bicarbonate solution (20 mL, gas evolution, pH=8-9) and brine (10 mL), combined, dried over MgSO4 and concentrated in vacuo. The crude material was purified by flash chromatography (using silica gel amine phase and an ethyl acetate/heptane gradient) to give the product as yellow foam (1.233 g, 4.29 mmol, 84.4%). MS: M=288.1 (M+H)+

Step 3: tert-Butyl 2-(1-methyl-4-phenyl-1H-imidazol-2-yl)ethylcarbamate

A suspension of tert-butyl 2-(4-phenyl-1H-imidazol-2-yl) ethylcarbamate (1.071 g, 3.73 mmol) and potassium carbonate (1.13 g, 8.2 mmol) in DMF (10 mL) was stirred at 20° C. for 30 min. Then the reaction mixture was cooled to 0-5° C. and iodomethane (280 µl, 4.47 mmol) was added and the resulting mixture was stirred for 30 min. After removal of the ice bath the reaction mixture was stirred at 20° C. for 6 h, poured into water (10 mL) and extracted with dichloromethane (2×20 mL). The organic layers were combined, dried over MgSO4 and concentrated in vacuo. The crude material was purified by flash chromatography (using silica gel amine phase and an ethyl acetate/heptane gradient) to give the product as light yellow solid (835 mg, 2.77 mmol, 74.3%). MS: M=302.2 (M+H)+

Step 4: 2-(1-Methyl-4-phenyl-1H-imidazol-2-yl)ethanamine dihydrochloride

To a suspension of tert-butyl 2-(1-methyl-4-phenyl-1H-imidazol-2-yl)ethylcarbamate (831 mg, 2.76 mmol) in dioxane (5 mL) was added HCl in dioxane (4M, 6.89 mL, 27.6 mmol) dropwise. The reaction mixture was stirred at 20° C. for 1.5 h. The crude reaction mixture was concentrated in vacuo. Heptane was added and the suspension was stirred for 30 min and evaporated in vacuo to give the product as white solid (760 mg, 2.72 mmol, 98.5%). MS: M=202.3 (M−2HCl+H)+

Step 5: 4-(Azetidine-1-carbonyl)-2-methyl-2H-pyrazole-3-carboxylic acid [2-(1-methyl-4-phenyl-1H-imidazol-2-yl)-ethyl]-amide To a suspension of intermediate A-1 (40 mg, 191 µmol) and 2-(1-methyl-4-phenyl-1H-imidazol-2-yl)ethanamine dihydrochloride (57.7 mg, 210 µmol) in THF (1 mL) were added under nitrogen atmosphere 1-propanephosphonic acid cyclic anhydride (50% in ethyl acetate, 287 µl, 478 µmol) and N,N-diisopropylethylamine (267 µl, 1.53 mmol). The reaction mixture was heated to 70° C. and stirred for 2 h. The crude product was purified after removal of all volatiles by preparative HPLC using an acetonitrile/water gradient as white solid (31 mg, 79.0 µmol, 41.3%). MS: M=393.2 (M+H)+

Example 8

2,3-Dimethyl-5-(morpholine-4-carbonyl)-3H-imidazole-4-carboxylic acid [2-(1-methyl-1H-benzoimidazol-2-yl)-ethyl]-amide

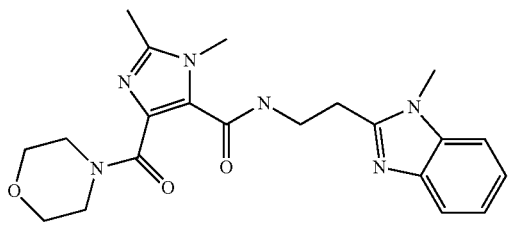 [SMILES: Cc1nc(C(=O)N2CCOCC2)c(C(=O)NCCc2nc3ccccc3n2C)n1C]

Step 1: 1,2-Dimethyl-1H-imidazole-4,5-dicarboxylic acid dimethyl ester

To a suspension of dimethyl 2-methyl-1H-imidazole-4,5-dicarboxylate (2 g, 10.1 mmol, prepared according to J. Med. Chem. 1989, 32, 119) in DMF (20 mL) was added under a nitrogen atmosphere potassium tert-butoxide (1.25 g, 11.1 mmol) at room temperature. The mixture was stirred for 15 min and iodomethane (694 µL, 11.1 mmol) was added. The reaction mixture was stirred for 2 h at the same temperature. The reaction mixture was poured into water (75 mL) and extracted with ethyl acetate (2×100 mL). The organic phase was washed water (3×50 mL) and brine (20 mL), dried and concentrated in vacuo to give 720 mg of crude product. The combined aqueous phases were back-extracted dichloromethane (4×50 mL), dried over MgSO$_4$ and concentrated in vacuo to give another 1.4 g of crude product. The combined crude material was purified by flash chromatography (using silica gel and a MeOH/dichloromethane gradient) to give the product as colorless oil (1.89 g, 8.91 mmol, 88.3%). MS: M=213.1 (M+H)+

Step 2: 1,2-Dimethyl-1H-imidazole-4,5-dicarboxylic acid 4-methyl ester

To a solution of dimethyl 1,2-dimethyl-1H-imidazole-4,5-dicarboxylate (1.89 g, 8.91 mmol) in THF (35 mL) and MeOH (15 mL) was added at 0-5° C. LiOH (1M; 9.35 mL, 9.35 mmol). The reaction mixture was stirred at RT for 7 h and the solvents were evaporated in vacuo. The residue was poured into water (20 mL) and ethyl acetate (30 mL). The ethyl acetate phase was washed with water (10 mL). The combined aqueous phases were acidified with hydrochloric acid (1M, 10 mL) and extracted with dichloromethane/MeOH (95:5, 8×60 mL). The dichloromethane/MeOH phases were dried over MgSO4, filtered and evaporated to give the product as colorless solid (1.29 g, 6.51 mmol, 73.1%). MS: M=199.1 (M+H)+

Step 3: 1,2-Dimethyl-5-(2-(1-methyl-1H-benzo[d]imidazol-2-yl)ethylcarbamoyl)-1H-imidazole-4-carboxylic acid methyl ester The product was obtained starting from 1,2-dimethyl-1H-imidazole-4,5-dicarboxylic acid 4-methyl ester (200 mg, 1.01 mmol) and 2-(1-methyl-1H-benzo[d]imidazol-2-yl)ethanamine (195 mg, 1.11 mmol) according to the method described in example 7, step 5 after aqueous work-up and purification by flash chromatography (using silica gel amine phase and a MeOH/ethyl acetate gradient) as light red gum (98 mg, 276 µmol, 27.3%). MS: M=356.1 (M+H)+

Step 4: 1,2-Dimethyl-5-(2-(1-methyl-1H-benzo[d]imidazol-2-yl)ethylcarbamoyl)-1H-imidazole-4-carboxylic acid To a solution of methyl 1,2-dimethyl-5-(2-(1-methyl-1H-benzo[d]imidazol-2-yl)ethylcarbamoyl)-1H-imidazole-4-carboxylate (98 mg, 276 µmol) in THF (2 mL) and MeOH (1 mL) at room temperature was added LiOH (1M, 1.1 mL, 1.1 mmol). The reaction mixture was stirred at r. t. for 6 h. The reaction mixture was acidified with hydrochloric acid (1M, 1.5 mL), all volatiles were removed in vacuo and the residue was suspended in dichloromethane/MeOH (95:5) and filtered. The liquid was evaporated and dried in vacuo to give the product as colorless amorphous material (95 mg, 264 µmol, 95.9%) which was used without any further purification for the next step. MS: M=340.2 (M−H)−

Step 5: 2,3-Dimethyl-5-(morpholine-4-carbonyl)-3H-imidazole-4-carboxylic acid [2-(1-methyl-1H-benzoimidazol-2-yl)-ethyl]-amide The product was obtained starting from 1,2-dimethyl-5-(2-(1-methyl-1H-benzo[d]imidazol-2-yl)ethylcarbamoyl)-1H-imidazole-4-carboxylic acid (51 mg, 149 µmol) and morpholine (39.0 µL, 448 µmol) according to the method described in example 8, step 3 as light brown waxy solid (17.3 mg, 42.1 µmol, 28.2%). MS: M=411.3 (M+H)+

Example 9

4-(Azetidine-1-carbonyl)-2-methyl-2H-pyrazole-3-carboxylic acid (2-benzothiazol-2-yl-ethyl)-amide

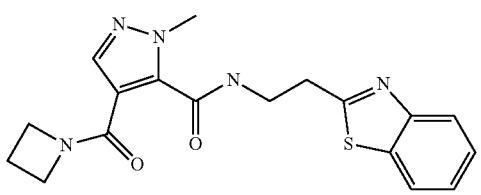 [SMILES: Cn1ncc(C(=O)N2CCC2)c1C(=O)NCCc1nc2ccccc2s1]

The product was obtained starting from intermediate A-1 (38 mg, 182 µmol, Eq: 1.00) and 2-(benzo[d]thiazol-2-yl)ethanamine (35 mg, 196 µmol, Eq: 1.08) according to the

Example 10

5-(Azetidine-1-carbonyl)-3-methyl-3H-imidazole-4-carboxylic acid [2-(1-methyl-1-benzoimidazol-2-yl)-ethyl]-amide

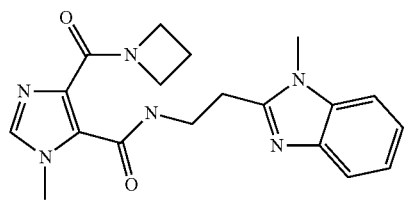 [SMILES: Cn1cnc(C(=O)N2CCC2)c1C(=O)NCCc1nc2ccccc2n1C]

Step 1: Dimethyl 1-methyl-1H-imidazole-4,5-dicarboxylate

The product was obtained starting from dimethyl 1H-imidazole-4,5-dicarboxylate (2 g, 10.9 mmol) according to the method described in example 8, step 1 as colorless oil (1.76 g, 8.88 mmol, 81.8%). MS: M=167.2 (M+H−CH3OH)+

Step 2: 1-Methyl-1H-imidazole-4,5-dicarboxylic acid 4-methyl ester

The product was obtained starting from dimethyl 1-methyl-1H-imidazole-4,5-dicarboxylate (1.76 g, 8.88 mmol) according to the method described in example 8, step 2 as white solid (850 mg, 4.62 mmol, 52.0%). MS: M=185.1 (M+H)+

Step 3: 1-Methyl-5-(2-(1-methyl-1H-benzo[d]imidazol-2-yl)ethylcarbamoyl)-1H-imidazole-4-carboxylic acid methyl ester The product was obtained starting from 1-methyl-1H-imidazole-4,5-dicarboxylic acid 4-methyl ester (200 mg, 1.09 mmol) and 2-(1-methyl-1H-benzo[d]imidazol-2-yl)ethanamine dihydrochloride (296 mg, 1.19 mmol) according to the method described in example 8, step 3 as pink foam (156 mg, 457 µmol, 42.1%). MS: M=342.1 (M+H)+

Step 4: 1-Methyl-5-(2-(1-methyl-1H-benzo[d]imidazol-2-yl)ethylcarbamoyl)-1H-imidazole-4-carboxylic acid The product was obtained starting from methyl 1-methyl-5-(2-(1-methyl-1H-benzo[d]imidazol-2-yl)ethylcarbamoyl)-1H-imidazole-4-carboxylate (151 mg, 442 µmol) according to the method described in example 8, step 3 as purple solid (231 mg, 423 µmol, 95.7%). MS: M=326.2 (M−H)−

Step 5: 5-(Azetidine-1-carbonyl)-3-methyl-3H-imidazole-4-carboxylic acid [2-(1-methyl-1-benzoimidazol-2-yl)-ethyl]-amide The product was obtained starting from 1-methyl-5-(2-(1-methyl-1H-benzo[d]imidazol-2-yl)ethylcarbamoyl)-1H-imidazole-4-carboxylic acid (80 mg, 147 µmol) and azetidine (29.7 µl, 440 µmol) according to the method described in example 7, step 5 after purification by flash chromatography (using silica gel amine phase and a MeOH/ethyl acetate gradient) as white solid (22 mg, 60.0 µmol, 40.9%). MS: M=367.2 (M+H)+

Example 11

4-(Azetidine-1-carbonyl)-2-methyl-2H-pyrazole-3-carboxylic acid [2-(1,5-dimethyl-1H-benzoimidazol-2-yl)-ethyl]-amide

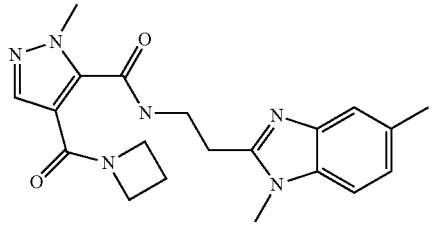 [SMILES: Cc1ccc2c(c1)nc(CCNC(=O)c1c(C(=O)N3CCC3)cnn1C)n2C]

The product was obtained starting from intermediate A-1 (38 mg, 184 µmol, Eq: 1.00) and 2-(1,5-dimethyl-1H-benzo[d]imidazol-2-yl)ethanamine dihydrochloride (62.7 mg, 239 µmol, Eq: 1.3) according to the method described in example 3 after 22 h stirring using 8 equivalents of N-methylmorpholine and after purification by preparative HPLC using an acetonitrile/water (containing 0.1% triethylamine) gradient as colorless solid (30.8 mg, 81.0 µmol, 44.0%). MS: M=381.2 (M+H)+

Example 12

4-(Azetidine-1-carbonyl)-2-methyl-2H-pyrazole-3-carboxylic acid [2-(3-phenyl-pyrazol-1-yl)-ethyl]-amide

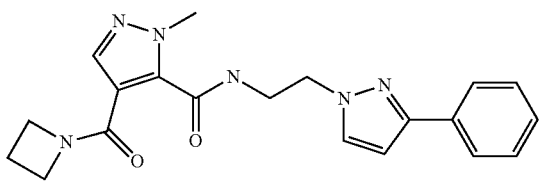 [SMILES: Cn1ncc(C(=O)N2CCC2)c1C(=O)NCCn1ccc(-c2ccccc2)n1]

The product was obtained starting from intermediate A-1 (38 mg, 184 µmol) and 2-(3-phenyl-1H-pyrazol-1-yl)ethanamine hydrochloride (53.5 mg, 239 µmol) according to the method described in example 3 as colorless solid (31 mg, 81.9 µmol, 44.5%). MS: M=379.3 (M+H)+

Example 13

5-(Azetidine-1-carbonyl)-2-chloro-3-methyl-3H-imidazole-4-carboxylic acid [2-(1-methyl-1H-benzoimidazol-2-yl)-ethyl]-amide

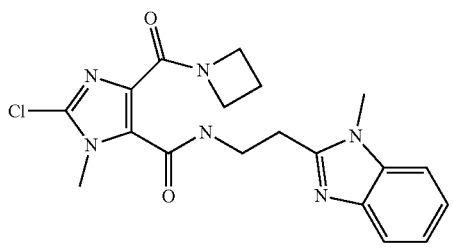 [SMILES: Cn1c(Cl)nc(C(=O)N2CCC2)c1C(=O)NCCc1nc2ccccc2n1C]

Step 1: Dimethyl 2-chloro-1-methyl-1H-imidazole-4,5-dicarboxylate

To a colorless solution of dimethyl 1-methyl-1H-imidazole-4,5-dicarboxylate (500 mg, 2.42 mmol, Eq: 1.00) in DMF (5.00 mL) was added under a nitrogen atmosphere 1,3-dichloro-5,5-dimethylhydantoin (487 mg, 2.42 mmol, Eq: 1.00). The reaction mixture was heated to 80° C. and stirred for 2 h, cooled down to ambient temperature, poured into saturated sodium bicarbonate solution (5 mL) and extracted with ethyl acetate (2×10 mL). The organic layers were washed with brine (5 mL), dried over MgSO4 and concentrated in vacuo. The crude material was purified by flash chromatography (using silica gel and an ethyl acetate/heptane gradient) to give the product as colorless oil (415 mg, 1.78 mmol, 73.7%). MS: M=233.0 (M+H)+

Step 2: 2-Chloro-1-methyl-1H-imidazole-4,5-dicarboxylic acid 4-methyl ester

The product was obtained starting from dimethyl 2-chloro-1-methyl-1H-imidazole-4,5-dicarboxylate (449 mg, 1.93 mmol) according to the method described in example 8, step 2 as white solid (336 mg, 1.54 mmol, 79.6%). MS: M=219.0 (M+H)+

Step 3: 2-Chloro-1-methyl-5-(2-(1-methyl-1H-benzo[d]imidazol-2-yl)ethylcarbamoyl)-1H-imidazole-4-carboxylic acid methyl ester The product was obtained starting from 2-(1-methyl-1H-benzo[d]imidazol-2-yl)ethanamine dihydrochloride (125 mg, 504 µmol) and 2-chloro-1-methyl-1H-imidazole-4,5-dicarboxylic acid 4-methyl ester (172 mg, 787 µmol) according to the method described in example 8, step 3 as purple solid (77 mg, 205 µmol, 40.7%). MS: M=376.3 (M+H)+

Step 4: 2-Chloro-1-methyl-5-(2-(1-methyl-1H-benzo[d]imidazol-2-yl)ethylcarbamoyl)-1H-imidazole-4-carboxylic acid The product was obtained starting from methyl 2-chloro-1-methyl-5-(2-(1-methyl-1H-benzo[d]imidazol-2-yl)ethylcarbamoyl)-1H-imidazole-4-carboxylate (73 mg, 194 µmol) according to the method described in example 8, step 4 after precipitation from the acid phase as white solid (60 mg, 166 µmol, 85.4%). MS: M=360.2 (M–H)–

Step 5: 5-(Azetidine-1-carbonyl)-2-chloro-3-methyl-3H-imidazole-4-carboxylic acid [2-(1-methyl-1H-benzoimidazol-2-yl)-ethyl]-amide The product was obtained starting from 2-chloro-1-methyl-5-(2-(1-methyl-1H-benzo[d]imidazol-2-yl)ethylcarbamoyl)-1H-imidazole-4-carboxylic acid (30 mg, 82.9 µmol) and azetidine (14.2 mg, 16.9 µl, 249 µmol) according to the method described in example 7, step 5 as white waxy solid (17.5 mg, 41.5 µmol, 50.0%). MS: M=401.2 (M+H)+

Example 14

4-(Azetidine-1-carbonyl)-2-methyl-2H-pyrazole-3-carboxylic acid [2-(5-pyridin-4-yl-2H-[1,2,4]triazol-3-yl)-ethyl]-amide

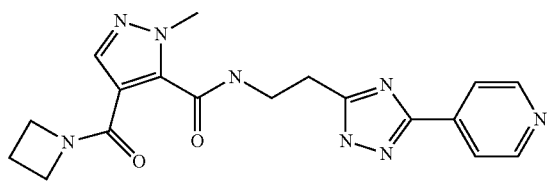 [SMILES: Cn1ncc(C(=O)N2CCC2)c1C(=O)NCCc1nc(-c2ccncc2)n[nH]1]

The product was obtained starting from intermediate A-1 (32 mg, 153 µmol) and 2-(3-(pyridin-4-yl)-1H-1,2,4-triazol-5-yl)ethanamine dihydrochloride (52.3 mg, 199 µmol) according to the method described in example 1 after purification using silical gel amine phase and subsequent trituration with ethyl acetate as white solid (14.7 mg, 38.6 µmol, 25.2%). MS: M=381.2 (M+H)+

Example 15

4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide

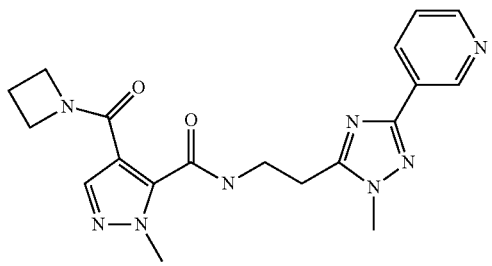 [SMILES: Cn1nc(-c2cccnc2)nc1CCNC(=O)c1c(C(=O)N2CCC2)cnn1C]

Step 1: 5-[2-Bis(tert-butoxycarbonyl)aminoethyl]-3-pyridin-3-yl-[1,2,4]triazole

To a suspension of 2-(3-(pyridin-3-yl)-1H-1,2,4-triazol-5-yl)ethanamine dihydrochloride (400 mg, 1.53 mmol) in dichloroethane (5 mL) were added N,N-diisopropylethylamine (493 mg, 666 µl, 3.81 mmol) and DMAP (9.32 mg, 76.3 µmol) under a nitrogen atmosphere at RT. A solution of di-tert-butyl dicarbonate (0.999 g, 1.06 mL, 4.58 mmol) in dichloroethane (5 mL) was added dropwise over 5 min at RT and stirring was continued at the same temperature for 2 h. The reaction mixture was poured into an aqueous potassium hydrogensulfate solution (10%, 25 mL) and extracted with ethyl acetate (2×75 mL). The combined organic phase was washed with water (2×25 mL) and brine (20 mL). The organic layer was dried over MgSO4, concentrated in vacuo, dissolved in dichloromethane and purified by flash chromatography (using silica gel and an ethyl acetate/heptane gradient, 30 mL/min., 254 nm) to give the product as light yellow oil (382 mg, 981 µmol, 64.3%). MS: M=390.3 (M+H)+

Step 2: 5-[2-Bis(tert-butoxycarbonyl)aminoethyl]-1-methyl-3-pyridin-3-yl-[1,2,4]triazole The product was obtained starting from 5-[2-bis(tert-butoxycarbonyl)aminoethyl]-3-pyridin-3-yl-[1,2,4]triazole (382 mg, 981 µmol) according to the method described in example 8, step 1 after purification by flash chromatography (using an ethyl acetate/heptane gradient) as colorless oil (133 mg, 330 µmol, 33.7%). MS: M=404.2 (M+H)+

Step 3: 2-(1-Methyl-3-(pyridin-3-yl)-1H-1,2,4-triazol-5-yl)ethanamine dihydrochloride 5-[2-Bis(tert-butoxycarbonyl)aminoethyl]-1-methyl-3-pyridin-3-yl-[1,2,4]triazole (133 mg, 330 µmol) was suspended in hydrochloric acid (4M solution in dioxane, 2 mL, 8.00 mmol) and the mixture was stirred at r. t. for 1 h. The reaction mixture was evaporated and dried to give the product as colorless solid (118 mg, 342 µmol, 104%) which was used without any further purification for the next step. MS: M=204.2 (M+H)+

Step 4: 4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide The product was obtained starting from intermediate A-1 (38 mg, 184 µmol) and 2-(1-methyl-3-(pyridin-3-yl)-1H-1,2,4-triazol-5-yl)ethanamine dihydrochloride (82.6 mg, 239 µmol) according to the method described in example 3 performing a preparative HPLC purification (using an acetonitrile/water (containing 0.1% triethylamine) gradient) and a subsequent flash chromatography (using a MeOH/ethyl acetate gradient) as colorless amorphous material (6.2 mg, 14.9 µmol, 8.12%). MS: M=395.2 (M+H)+

Example 16

4-(Azetidine-1-carbonyl)-2-methyl-2H-pyrazole-3-carboxylic acid [2-(5-chloro-1-methyl-1H-benzoimidazol-2-yl)-ethyl]-amide

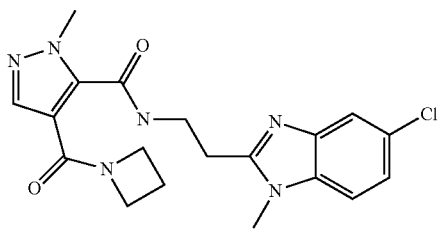 [SMILES: Cn1ncc(C(=O)N2CCC2)c1C(=O)NCCc1nc2cc(Cl)ccc2n1C]

The product was obtained starting from intermediate A-1 (32 mg, 153 µmol) and 2-(5-chloro-1-methyl-1H-benzo[d]imidazol-2-yl)ethanamine hydrochloride (49.1 mg, 199 µmol) according to the method described in example 3 after purification by preparative HPLC using an acetonitrile/water (containing 0.1% triethylamine) gradient as colorless solid (30 mg, 74.8 µmol, 48.8% yield). MS: M=401.2 (M+H)+

Example 17

4-(Azetidine-1-carbonyl)-2-methyl-2H-pyrazole-3-carboxylic acid [2-(2-methyl-5-pyridin-4-yl-2H-[1,2,4]triazol-3-yl)-ethyl]-amide

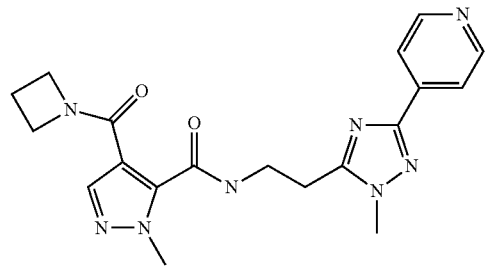 [SMILES: Cn1nc(-c2ccncc2)nc1CCNC(=O)c1c(C(=O)N2CCC2)cnn1C]

Step 1: 3-(1,3-Dioxo-1,3-dihydro-isoindol-2-yl)-thiopropionamide

A suspension of 3-(1,3-dioxoisoindolin-2-yl)-propionitrile (2 g, 9.99 mmol) and dithiophosphoric acid O,O'-diethyl ester (2.05 g, 1.74 mL, 11.0 mmol) in water (4 mL) was irradiated at 80° C. for 10 min. The obtained suspension was diluted with water (5 mL), filtered, washed with water and dried in vacuo to give the product as light yellow solid (2.13 g, 9.09 mmol, 91.0%) which was used without further purification for the next step. MS: M=235.1 (M+H)+

Step 2: 3-(1,3-Dioxo-1,3-dihydro-isoindol-2-yl)-thiopropionimidic acid methyl ester hydroiodide To a suspension of 3-(1,3-dioxo-1,3-dihydro-isoindol-2-yl)-thiopropionamide (2.13 g, 9.09 mmol) in acetone (30 mL) was added iodomethane (3.87 g, 1.71 mL, 27.3 mmol) at r. t. under a nitrogen atmosphere. The reaction mixture was stirred at RT for 48 h and the obtained suspension was filtered, washed with diethyl ether and dried in vacuo to give the product as light yellow solid (2.3 g, 6.11 mmol, 67.2%). MS: M=249.1 (M+H)+

Step 3: 2-(2-(5-(Pyridin-4-yl)-4H-1,2,4-triazol-3-yl)ethyl)isoindoline-1,3-dione To a suspension of 3-(1,3-dioxo-1,3-dihydro-isoindol-2-yl)-thiopropionimidic acid methyl ester hydroiodide (880 mg, 2.34 mmol) in 2-propanol (16 mL) were added isonicotinohydrazide (337 mg, 2.46 mmol) and sodium carbonate (248 mg, 2.34 mmol). The reaction mixture was stirred at 85° C. for 1 h. Acetic acid (32 mL) was added and the reaction mixture was stirred at 130° C. for 3 h. After cooling down to ambient temperature, all volatiles were evaporated. The residue was dissolved in acetic acid (30 mL) and the reaction mixture was stirred at 130° C. for 16 h. The reaction mixture was cooled down to RT and concentrated in vacuo. The residue was poured into saturated sodium bicarbonate solution (40 mL) and extracted with ethyl acetate (2×80 mL). The combined organic phase was washed water (40 mL) and brine (40 mL), dried over MgSO4 and concentrated in vacuo. The residue was suspended in dichloromethane, filtered, washed with dichloromethane and dried in vacuo to give the product as brown solid (480 mg (purity 80%), 0.96 mmol, 41%). The filtrate was evaporated and pure product was obtained after purification by flash chromatography (using silica gel and an ethyl acetate/heptane gradient) as light brown solid (180 mg, 562 µmol, 24.0%). MS: M=321.1 (M+H)+

Step 4: 2-(2-(1-Methyl-3-(pyridin-4-yl)-1H-1,2,4-triazol-5-yl)ethyl)isoindoline-1,3-dione The product was obtained starting from 2-(2-(5-(pyridin-4-yl)-4H-1,2,4-triazol-3-yl)ethyl)isoindoline-1,3-dione (300 mg, 752 µmol) according to the method described in example 8, step 1 using 1.3 equivalents of potassium tert-butoxide and iodomethane with a reaction time of 16 h and after purification by flash chromatography (using silica gel and a MeOH/ethyl acetate gradient) as white solid (114.9 mg, 345 µmol, 45.9%). MS: M=334.1 (M+H)+

Step 5: 2-(1-Methyl-3-(pyridin-4-yl)-1H-1,2,4-triazol-5-yl)ethanamine 2-(2-(1-Methyl-3-(pyridin-4-yl)-1H-1,2,4-triazol-5-yl) ethyl)isoindoline-1,3-dione (114.9 mg, 345 µmol) was dissolved in methylamine solution in EtOH (3.07 mL, 22.5 mmol) and stirred at RT for 1 h. The reaction mixture was evaporated to give light brown solid. The solid was again dissolved in methylamine solution in EtOH (3.07 mL, 22.5 mmol) and the mixture was heated to 50° C. and stirred for 3 h. All volatiles were removed in vacuo and the residue was suspended in dichloromethane (1.5 mL) and filtered. The filtrate was evaporated to give the product as light yellow solid (81.3 mg (80% purity), 256 µmol, 74.2%) which was used without purification for the next step. MS: M=204.2 (M+H)+

Step 6: 4-(Azetidine-1-carbonyl)-2-methyl-2H-pyrazole-3-carboxylic acid [2-(2-methyl-5-pyridin-4-yl-2H-[1,2,4]triazol-3-yl)-ethyl]-amide The product was obtained starting from intermediate A-1 (50 mg, 239 µmol) and 2-(1-methyl-3-(pyridin-4-yl)-1H-1,2,4-triazol-5-yl)ethanamine (77.9 mg, 307 µmol) according to the method described in example 1 as light yellow solid (42.2 mg, 107 µmol, 44.8% yield). MS: M=395.2 (M+H)+

Example 18

4-(Azetidine-1-carbonyl)-2-methyl-2H-pyrazole-3-carboxylic acid [2-(3-phenyl-[1,2,4]triazol-1-yl)-ethyl]-amide

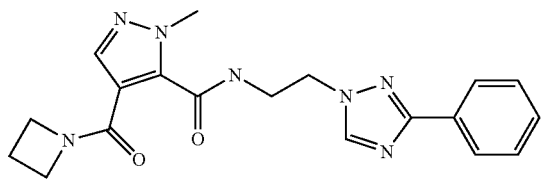 [SMILES: Cn1ncc(C(=O)N2CCC2)c1C(=O)NCCn1cnc(-c2ccccc2)n1]

Step 1: 3-Phenyl-1H-1,2,4-triazole

To a suspension of ethyl benzimidate hydrochloride (2 g, 10.8 mmol) in EtOH (10.0 mL) was added sodium ethoxide (21% in EtOH, 4.02 mL, 10.8 mmol). The precipitated sodium chloride was filtered off, washed with EtOH (14.0 mL) and formohydrazide (712 mg, 11.9 mmol) was added. The reaction mixture was stirred at 20° C. for 92 h and the solvent was removed in vacuo. Sodium hydroxide (1 M, 50 mL) was added and the resulting mixture was extracted with tert-butylmethylether (100 mL). The organic layer was washed with water and solid carbon dioxide was added to adjust the pH to 10. The resulting suspension was filtered and the liquid phase was evaporated. Dichloromethane/MeOH (9:1) was added, the reaction mixture was filtered and the solvent of the filtrate was evaporated to give the product as light brown semisolid material (1.48 g, 9.18 mmol, 85.2%). MS: M=146.1 (M+H)+

Step 2: 3-(3-Phenyl-1H-1,2,4-triazol-1-yl)propionoic acid

A mixture of 3-phenyl-1H-1,2,4-triazole (1.46 g, 9.05 mmol), 3-chloropropionic acid (1.08 g, 9.96 mmol) and sodium hydroxide (2M, 9.05 mL, 18.1 mmol) in water (3 mL) was heated to 115° C. and stirred for 66 h. Another 0.5 equivalents of each 3-chloropropanoic acid and sodium hydroxide were added (pH increase to 11) and stirring was continued for another 24 h. Hydrochloric acid (2M, 10 mL) was added, the suspension was filtered and extracted with dichloromethane. The product was obtained after purification by supercritical fluid chromatography as light brown solid (236 mg, 1.09 mmol, 12.0%). MS: M=218.1 (M+H)+

Step 3: tert-Butyl 2-(3-phenyl-1H-1,2,4-triazol-1-yl)ethylcarbamate

A mixture of 3-(3-phenyl-1H-1,2,4-triazol-1-yl)propionoic acid (195 mg, 862 µmol), diphenyl phosphorazidate (242 µl, 1.12 mmol), triethylamine (240 µl, 1.72 mmol) in ter-butanol (33 mL) was heated at 50° C. for 5 h. Stirring was continued at 90° C. for another 12 h and all volatiles were removed in vacuo. The crude product was purified by preparative HPLC using an acetonitrile/water (containing 0.1% formic acid) gradient to afford the product as colorless oil (37 mg, 122 µmol, 14.1%). MS: M=289.1 (M+H)+

Step 4: 2-(3-Phenyl-1H-1,2,4-triazol-1-yl)ethanamine dihydrochloride

To a solution of tert-butyl 2-(3-phenyl-1H-1,2,4-triazol-1-yl)ethylcarbamate (34 mg, 118 µmol) in dioxane (1 mL) was added hydrochloric acid (4M in dioxane, 590 µl, 2.36 mmol). The reaction mixture was stirred at RT for 18 h. All volatiles were removed in vacuo and the product was dried to yield a white solid (38 mg, 116 µmol, 98.7%) that was used without additional purification. MS: =189.3 M+H)+

Step 5: 4-(Azetidine-1-carbonyl)-2-methyl-2H-pyrazole-3-carboxylic acid [2-(3-phenyl-[1,2,4]triazol-1-yl)-ethyl]-amide The product was obtained starting from intermediate A-1 (20 mg, 95.6 µmol) and 2-(3-phenyl-1H-1,2,4-triazol-1-yl) ethanamine dihydrochloride (34 mg, 104 µmol) according to the method described in example 3 as white solid (26 mg, 68.5 µmol, 71.7%). MS: M=380.2 (M+H)+

Example 19

4-(Azetidine-1-carbonyl)-2-methyl-2H-pyrazole-3-carboxylic acid [2-(2-phenyl-2H-[1,2,3]triazol-4-yl)-ethyl]-amide

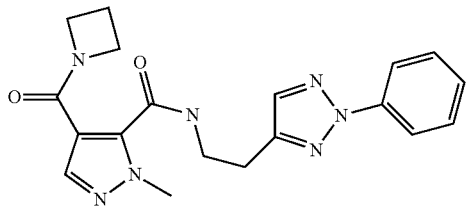 [SMILES: Cn1ncc(C(=O)N2CCC2)c1C(=O)NCCc1cnn(-c2ccccc2)n1]

The product was obtained starting from intermediate A-1 (50 mg, 239 μmol) and 2-(2-phenyl-2H-1,2,3-triazol-4-yl)ethanamine (49.5 mg, 263 μmol) according to the method described in example 3 as white solid (69 mg, 182 μmol, 76.1%). MS: M=380.3 (M+H)+

Example 20

4-(Azetidine-1-carbonyl)-2-methyl-2H-pyrazole-3-carboxylic acid [2-(5-methyl-2-phenyl-oxazol-4-yl)-ethyl]-amide

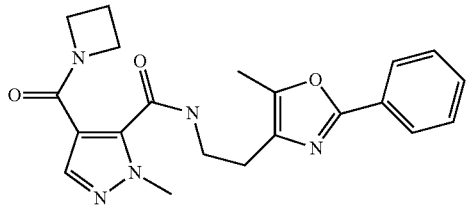 [SMILES: Cc1oc(-c2ccccc2)nc1CCNC(=O)c1c(C(=O)N2CCC2)cnn1C]

The product was obtained starting from intermediate A-1 (40 mg, 191 μmol) and 2-(5-methyl-2-phenyloxazol-4-yl)ethanamine (47 mg, 232 μmol) according to the method described in example 3 and subsequent purification by flash chromatography (using silica gel and an ethyl acetate/heptane gradient) as colorless solid (7.2 mg, 18.3 μmol, 9.57%). MS: M=394.2 (M+H)+

Example 21

4-(Azetidine-1-carbonyl)-2-methyl-2H-pyrazole-3-carboxylic acid [2-(5-phenyl-[1,2,4]oxadiazol-3-yl)-ethyl]-amide

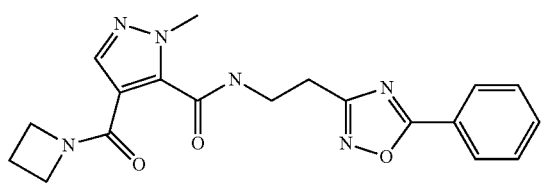 [SMILES: Cn1ncc(C(=O)N2CCC2)c1C(=O)NCCc1noc(-c2ccccc2)n1]

The product was obtained starting from intermediate A-1 (40 mg, 191 μmol) and 2-(5-phenyl-1,2,4-oxadiazol-3-yl)ethanamine hydrochloride (51.8 mg, 229 μmol) according to the method described in example 20 as white solid (46.6 mg, 123 μmol, 64.1%). MS: M=381.2 (M+H)+

Example 22

4-(Azetidine-1-carbonyl)-2-methyl-2H-pyrazole-3-carboxylic acid [2-(2-methyl-5-phenyl-2H-[1,2,4]triazol-3-yl)-ethyl]-amide

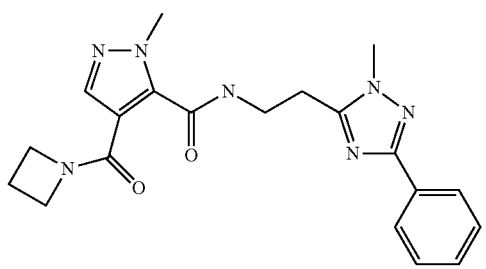 [SMILES: Cn1nc(-c2ccccc2)nc1CCNC(=O)c1c(C(=O)N2CCC2)cnn1C]

Step 1: 5-[2-Bis(tert-butoxycarbonyl)aminoethyl]-3-phenyl-[1,2,4]triazole

The product was obtained starting from 2-(3-phenyl-1H-1,2,4-triazol-5-yl)ethanamine trihydrochloride (500 mg, 1.68 mmol) according to the method described in example 15, step 1 as colorless oil (663 mg, 1.67 mmol, 99.6%). MS: M=389.3 (M+H)+

Step 2: 5-[2-Bis(tert-butoxycarbonyl)aminoethyl]-1-methyl-3-phenyl-[1,2,4]triazole The product was obtained starting from 5-[2-bis(tert-butoxycarbonyl)aminoethyl]-3-phenyl-[1,2,4]triazole (663 mg, 1.67 mmol) according to the method described in example 15, step 2 as colorless oil (251 mg, 0.62 mmol, 37.3%). MS: M=403.2 (M+H)+

Step 3: 2-(1-Methyl-3-phenyl-1H-1,2,4-triazol-5-yl)ethanamine hydrochloride

The product was obtained starting from 5-[2-bis(tert-butoxycarbonyl)aminoethyl]-1-methyl-3-phenyl-[1,2,4]triazole (247.5 mg, 615 μmol) according to the method described in example 15, step 3 as white solid (143 mg, 599 μmol, 97.4%). MS: M=203.2 (M+H)+

Step 4: 4-(Azetidine-1-carbonyl)-2-methyl-2H-pyrazole-3-carboxylic acid [2-(2-methyl-5-phenyl-2H-[1,2,4]triazol-3-yl)-ethyl]-amide The product was obtained starting from intermediate A-1 (40 mg, 191 μmol) and 2-(1-methyl-3-phenyl-1H-1,2,4-triazol-5-yl)ethanamine hydrochloride (59.3 mg, 249 μmol) according to the method described in example 3 as colorless oil (51.1 mg, 130 μmol, 67.9%). MS: M=394.2 (M+H)+

Example 23

4-(Azetidine-1-carbonyl)-2-methyl-2H-pyrazole-3-carboxylic acid [1,1-dimethyl-2-(5-methyl-2-phenyl-oxazol-4-yl)-ethyl]-amide

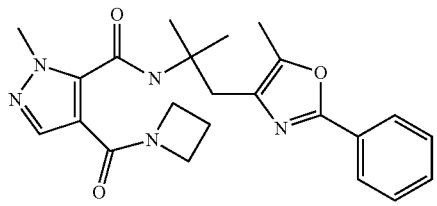 [SMILES: Cc1oc(-c2ccccc2)nc1CC(C)(C)NC(=O)c1c(C(=O)N2CCC2)cnn1C]

The product was obtained starting from intermediate A-1 (30 mg, 143 μmol) and 2-methyl-1-(5-methyl-2-phenyloxazol-4-yl)propan-2-amine (36.3 mg, 158 μmol; prepared according to WO 2003/037327, example 60) according to the method described in example 7, step 5 as colorless viscous oil (46.1 mg, 109 μmol, 76.3%). MS: M=422.2 (M+H)+

Example 24

2-Methyl-4-(morpholine-4-carbonyl)-2H-pyrazole-3-carboxylic acid [2-(1-methyl-4-phenyl-1H-imidazol-2-yl)-ethyl]-amide

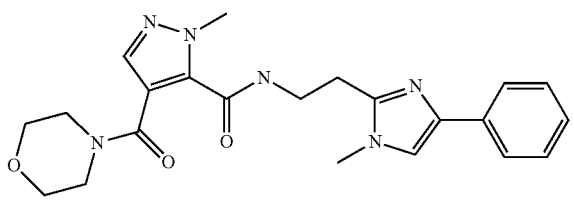 [SMILES: Cn1cc(-c2ccccc2)nc1CCNC(=O)c1c(C(=O)N2CCOCC2)cnn1C]

The product was obtained starting from intermediate A-2 (50 mg, 209 μmol) and 2-(1-methyl-4-phenyl-1H-imidazol-2-yl)ethanamine dihydrochloride (63.0 mg, 230 μmol; example 7, steps 1-4) according to the method described in example 8, step 5 as white solid (44 mg, 104 μmol, 49.8%). MS: M=423.2 (M+H)+

Example 25

4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide

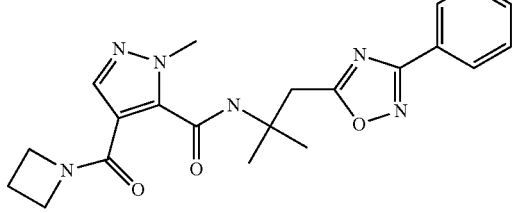

Step 1: tert-Butyl 2-methyl-1-(3-phenyl-1,2,4-oxadiazol-5-yl)propan-2-ylcarbamate A solution of 3-(tert-butoxycarbonylamino)-3-methylbutanoic acid (2.75 g, 12.7 mmol) and N,N'-carbonyldiimidazole (CDI; 2.05 g, 12.7 mmol) in DMF (20.0 mL) was stirred at RT under nitrogen atmosphere for 5 h. N-Hydroxybenzamidine (1.72 g, 12.7 mmol) was added and the reaction mixture was heated to 100° C. and stirred for 15 h. The crude reaction mixture was concentrated in vacuo, poured into ethyl acetate (100 mL) and extracted with water (3×100 mL). The combined aqueous layer was back-extracted with ethyl acetate (100 mL). The combined organic layer was dried over MgSO4, concentrated in vacuo and purified by flash chromatography (using silica gel and an ethyl acetate/heptane gradient) to yield the product as white solid (2.72 g, 8.57 mmol, 67.5%). MS: M=318.1 (M+H)+

Step 2: 2-Methyl-1-(3-phenyl-1,2,4-oxadiazol-5-yl)propan-2-amine hydrochloride A solution of tert-butyl 2-methyl-1-(3-phenyl-1,2,4-oxadiazol-5-yl)propan-2-ylcarbamate (2.72 g, 8.57 mmol) and HCl (4M in dioxane; 21.4 mL, 85.7 mmol) was stirred at 25° C. for 3 h. The resulting white suspension was diluted with tert-butylmethylether (100 mL) and stirred for 1 h. The reaction mixture was filtered and the precipitate was dried in vacuo to give the product as white solid (2.01 g, 7.92 mmol, 92.4%). MS: M=218.1 (M+H−HCl)+

Step 3: 4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide The product was obtained starting from intermediate A-1 (30 mg, 143 μmol) and 2-methyl-1-(3-phenyl-1,2,4-oxadiazol-5-yl)propan-2-amine hydrochloride (40.0 mg, 158 μmol) according to the method described in example 7, step 5 as white solid (50 mg, 122 μmol, 85.4%). MS: M=409.3 (M+H)+

Example 26

4-(Azetidine-1-carbonyl)-2-methyl-2H-pyrazole-3-carboxylic acid [2-(2-pyrimidin-2-yl-thiazol-4-yl)-ethyl]-amide

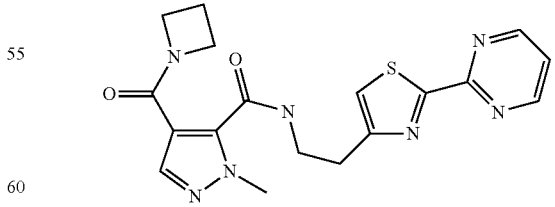

The product was obtained starting from intermediate A-1 (30 mg, 143 μmol) and 2-(2-(pyrimidin-2-yl)thiazol-4-yl)ethanamine dihydrochloride (40.0 mg, 143 μmol) according to the method described in example 7, step 5 as brown waxy solid (32.5 mg, 81.8 μmol, 57.0%). MS: M=398.2 (M+H)+

Example 27

4-(Azetidine-1-carbonyl)-2-methyl-2H-pyrazole-3-carboxylic acid [2-(1-methyl-4-pyridin-3-yl-1H-imidazol-2-yl)-ethyl]-amide

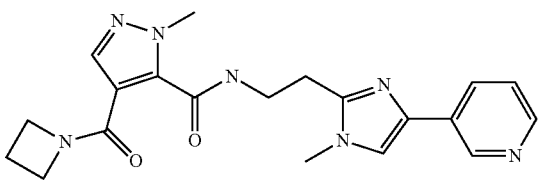 [SMILES: Cn1cc(-c2cccnc2)nc1CCNC(=O)c1c(C(=O)N2CCC2)cnn1C]

Step 1: 2-Oxo-2-(pyridin-3-yl)ethyl 3-(tert-butoxycarbonylamino)propanoate

The product was obtained starting from 3-(tert-butoxycarbonylamino)propanoic acid (1 g, 5.29 mmol) and 2-bromo-1-(pyridin-3-yl)ethanone hydrobromide (1.48 g, 5.29 mmol) according to the method described in example 7, step 1 after purification by flash chromatography (using silica gel and an ethyl acetate/heptane gradient) as white solid (1.255 g, 4.07 mmol, 77.0%). MS: M=309.2 (M+H)+

Step 2: tert-Butyl 2-(4-(pyridin-3-yl)-1H-imidazol-2-yl)ethylcarbamate

The product was obtained starting from 2-oxo-2-(pyridin-3-yl)ethyl 3-(tert-butoxycarbonylamino)propanoate (1.252 g, 4.06 mmol) according to the method described in example 7, step 2 as light yellow foam (744 mg, 2.58 mmol, 63.5%). MS: M=189.3 (M-Boc+H)+

Step 3: 3-(2-(2-(tert-Butoxycarbonylamino)ethyl)-1-methyl-1H-imidazol-4-yl)-1-methylpyridinium iodide The product was obtained starting from tert-butyl 2-(4-(pyridin-3-yl)-1H-imidazol-2-yl)ethylcarbamate (732 mg, 2.54 mmol) according to the method described in example 7, step 3 after purification by flash chromatography (using silica gel amine phase and a MeOH/ethyl acetate gradient) as brown foam (819 mg, 2.06 mmol, 81.3%). MS: M=317.2 (M−I+H)+

Step 4: tert-Butyl 2-(1-methyl-4-(pyridin-3-yl)-1H-imidazol-2-yl)ethylcarbamate A solution of 3-(2-(2-(tert-butoxycarbonylamino)ethyl)-1-methyl-1H-imidazol-4-yl)-1-methylpyridinium iodide (655 mg, 2.06 mmol) in 1-methylimidazole (2 mL, 25.1 mmol) was heated to 160° C. and stirred for 9 h. The reaction mixture was poured into water (5 mL) and extracted with dichloromethane (2×5 mL). The organic layers were combined, dried over MgSO4 and concentrated in vacuo. The crude material was purified by flash chromatography (using silica gel amine phase and an ethyl acetate/heptane gradient) to give 1.04 g of a light yellow liquid. The residual 1-methylimidazole was distilled of in a "Kugelrohr" (ball tube) vacuum distillation apparatus at 100-120° C. at ~0.2 mbar to yield the product as light yellow oil (102 mg, 337 μmol, 16.3%). MS: M=303.1 (M+H)+

Step 5: 2-(1-Methyl-4-(pyridin-3-yl)-1H-imidazol-2-yl)ethanamine trihydrochloride The product was obtained starting from tert-butyl 2-(1-methyl-4-(pyridin-3-yl)-1H-imidazol-2-yl)ethylcarbamate (100 mg, 331 μmol) according to the method described in example 7, step 4 as white solid (110 mg, 318 μmol, 96.1%). MS: M=203.2 (M+H)+

Step 6: 4-(Azetidine-1-carbonyl)-2-methyl-2H-pyrazole-3-carboxylic acid [2-(1-methyl-4-pyridin-3-yl-1H-imidazol-2-yl)-ethyl]-amide The product was obtained starting from intermediate A-1 (40 mg, 191 μmol) and 2-(1-methyl-4-(pyridin-3-yl)-1H-imidazol-2-yl)ethanamine trihydrochloride (66.2 mg, 191 μmol) according to the method described

Example 28

4-(Azetidine-1-carbonyl)-2-methyl-2H-pyrazole-3-carboxylic acid [2-(1-phenyl-1-pyrazol-3-yl)-ethyl]-amide

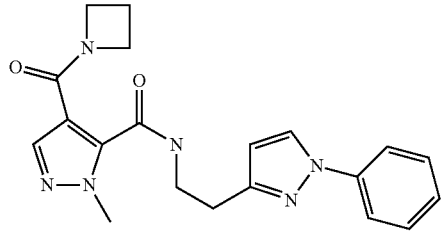 [SMILES: Cn1ncc(C(=O)N2CCC2)c1C(=O)NCCc1ccn(-c2ccccc2)n1]

The product was obtained starting from intermediate A-1 (30 mg, 143 μmol) and 2-(1-phenyl-1H-pyrazol-3-yl)ethanamine (26.9 mg, 143 μmol) according to the method described in example 7, step 5 as colorless solid (21 mg, 55.5 μmol, 38.7%). MS: M=379.3 (M+H)+

Example 29

4-(Azetidine-1-carbonyl)-2-methyl-2H-pyrazole-3-carboxylic acid [2-(2-phenyl-thiazol-4-yl)-ethyl]-amide

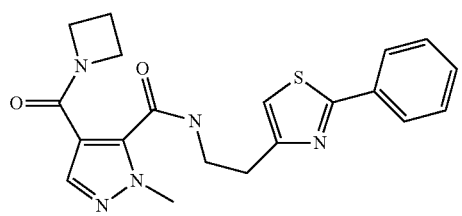 [SMILES: Cn1ncc(C(=O)N2CCC2)c1C(=O)NCCc1csc(-c2ccccc2)n1]

The product was obtained starting from intermediate A-1 (30 mg, 143 μmol) and 2-(2-phenylthiazol-4-yl)ethanamine (29.3 mg, 143 μmol) according to the method described in example 7, step 5 as light yellow solid (23 mg, 58.2 μmol, 40.6%). MS: M=396.2 (M+H)+

Example 30

4-(Azetidine-1-carbonyl)-2-methyl-2H-pyrazole-3-carboxylic acid {2-[4-(3-methoxy-phenyl)-1-methyl-1H-imidazol-2-yl]-ethyl}-amide

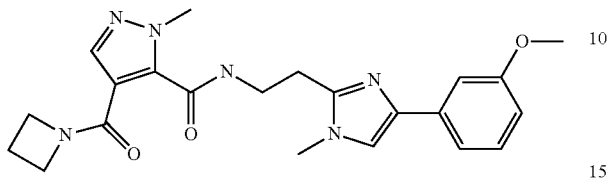

Step 1: 2-(3-Methoxyphenyl)-2-oxoethyl 3-(tert-butoxycarbonylamino)propanoate The product was obtained starting from 3-(tert-butoxycarbonylamino)propanoic acid (400 mg, 2.11 mmol) and 2-bromo-1-(3-methoxyphenyl)ethanone (484 mg, 2.11 mmol) according to the method described in example 7, step 1 as yellow oil (759 mg, 2.11 mmol, 100%). MS: M=238.2 (M−Boc+H)+

Step 2: tert-Butyl 2-(4-(3-methoxyphenyl)-1H-imidazol-2-yl)ethylcarbamate

The product was obtained starting from 2-(3-methoxyphenyl)-2-oxoethyl 3-(tert-butoxycarbonylamino)propanoate (755 mg, 2.1 mmol) according to the method described in example 7, step 2 as yellow foam (533 mg, 1.68 mmol, 79.8%). MS: M=318.3 (M+H)+

Step 3: tert-Butyl 2-(4-(3-methoxyphenyl)-1-methyl-1H-imidazol-2-yl)ethylcarbamate The product was obtained starting from tert-butyl 2-(4-(3-methoxyphenyl)-1H-imidazol-2-yl)ethylcarbamate (528 mg, 1.66 mmol) according to the method described in example 7, step 3 as white solid (350 mg, 1.06 mmol, 63.5%). MS: M=332.2 (M+H)+

Step 4: 2-(4-(3-Methoxyphenyl)-1-methyl-1H-imidazol-2-yl)ethanamine dihydrochloride The product was obtained starting from tert-butyl 2-(4-(3-methoxyphenyl)-1-methyl-1H-imidazol-2-yl)ethylcarbamate (344 mg, 1.04 mmol) according to the method described in example 7, step 4 as white solid (321 mg, 1.03 mmol, 99.6%). MS: M=232.1 (M−2HCl+H)+

Step 5: 4-(Azetidine-1-carbonyl)-2-methyl-2H-pyrazole-3-carboxylic acid {2-[4-(3-methoxy-phenyl)-1-methyl-1H-imidazol-2-yl]-ethyl}-amide The product was obtained starting from intermediate A-1 (40 mg, 191 µmol) and 2-(4-(3-methoxyphenyl)-1-methyl-1H-imidazol-2-yl)ethanamine dihydrochloride (64.0 mg, 210 µmol) according to the method described in example 7, step 5 after purification by flash chromatography using silica gel and an ethyl acetate/heptane gradient as white foam (49 mg, 116 µmol, 60.7%). MS: M=423.3 (M+H)+

Example 31

4-(Azetidine-1-carbonyl)-2-methyl-2H-pyrazole-3-carboxylic acid {2-[4-(2-methoxy-phenyl)-1-methyl-1H-imidazol-2-yl]-ethyl}-amide

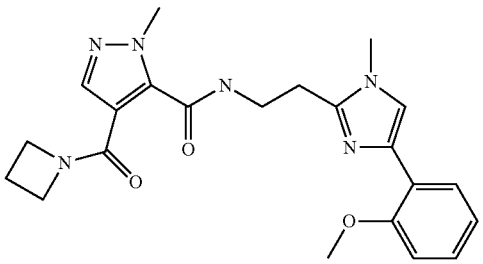 [SMILES: COc1ccccc1-c1cn(C)c(CCNC(=O)c2c(C(=O)N3CCC3)cnn2C)n1]

Step 1: 2-(2-Methoxyphenyl)-2-oxoethyl 3-(tert-butoxycarbonylamino)propanoate The product was obtained starting from 3-(tert-butoxycarbonylamino)propanoic acid (400 mg, 2.11 mmol) and 2-bromo-1-(2-methoxyphenyl)ethanone (484 mg, 2.11 mmol) according to the method described in example 7, step 1 as black oil (786 mg, 2.1 mmol, 99.2%). MS: M=238.2 (M−Boc+H)+

Step 2: tert-Butyl 2-(4-(2-methoxyphenyl)-1H-imidazol-2-yl)ethylcarbamate

The product was obtained starting from 2-(2-methoxyphenyl)-2-oxoethyl 3-(tert-butoxycarbonylamino)propanoate (784 mg, 2.09 mmol) according to the method described in example 7, step 2 as yellow foam (501 mg, 1.58 mmol, 75.5%). MS: M=218.3 (M−Boc+H)+

Step 3: tert-Butyl 2-(4-(2-methoxyphenyl)-1-methyl-1H-imidazol-2-yl)ethylcarbamate The product was obtained starting from tert-butyl 2-(4-(2-methoxyphenyl)-1H-imidazol-2-yl)ethylcarbamate (499 mg, 1.57 mmol) according to the method described in example 7, step 3 as brown solid (303 mg, 914 µmol, 58.2%). MS: M=332.2 (M+H)+

Step 4: 2-(4-(2-Methoxyphenyl)-1-methyl-1H-imidazol-2-yl)ethanamine dihydro chloride The product was obtained starting from tert-butyl 2-(4-(2-methoxyphenyl)-1-methyl-1H-imidazol-2-yl)ethylcarbamate (293 mg, 884 µmol) according to the method described in example 7, step 4 as light brown solid (271 mg, 873 µmol, 98.7%). MS: M=232.1 (M−2HCl+H)+

Step 5: 4-(Azetidine-1-carbonyl)-2-methyl-2H-pyrazole-3-carboxylic acid {2-[4-(2-methoxy-phenyl)-1-methyl-1H-imidazol-2-yl]ethyl}-amide The product was obtained starting from intermediate A-1 (40 mg, 191 µmol) and 2-(4-(2-methoxyphenyl)-1-methyl-1H-imidazol-2-yl)ethanamine dihydrochloride (64.0 mg, 210 µmol) according to the method described in example 30, step 5 as light brown solid (48 mg, 114 µmol, 59.4%). MS: M=423.2 (M+H)+

Example 32

4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide

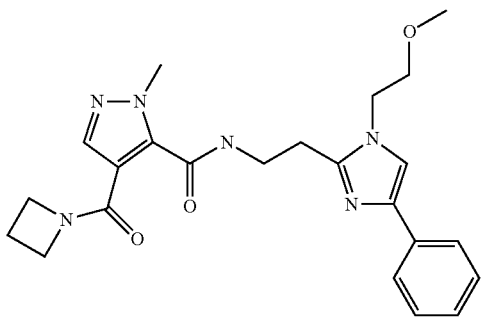 [SMILES: COCCn1cc(-c2ccccc2)nc1CCNC(=O)c1c(C(=O)N2CCC2)cnn1C]

Step 1: tert-Butyl 2-(1-(2-methoxyethyl)-4-phenyl-1H-imidazol-2-yl)ethylcarbamate A suspension of tert-butyl 2-(4-phenyl-1H-imidazol-2-yl) ethylcarbamate (400 mg, 1.39 mmol, prepared according to example 7, steps 1-2) and potassium carbonate (423 mg, 3.06 mmol) in DMF (4 mL) was stirred for 30 min at RT. After cooling to 0-5° C., 1-bromo-2-methoxyethane (157 μL, 1.67 mmol) was added. The ice bath was removed after 5 min and the reaction mixture was stirred at RT for 16 h. Another two equivalents of both potassium carbonate (618 mg, 4.45 mmol) and 1-bromo-2-methoxyethane (262 μL, 2.78 mmol) were added at RT and the reaction mixture was heated to 60° C. and stirred for 20 h. The reaction mixture was poured into ethyl acetate (50 mL) and the organic phase was washed with water (3×20 mL) and brine (25 mL). The aqueous layers were back-extracted with ethyl acetate (50 mL). The organic layers were dried over MgSO4 and concentrated in vacuo. The product was obtained after purification by flash chromatography (using silica gel and an ethyl acetate/heptane gradient) as colorless solid (359 mg, 1.04 mmol, 74.7%). MS: M=346.2 (M+H)+

Step 2: 2-(1-(2-Methoxyethyl)-4-phenyl-1H-imidazol-2-yl)ethanamine hydrochloride The product was obtained starting from tert-butyl 2-(1-(2-methoxyethyl)-4-phenyl-1H-imidazol-2-yl)ethylcarbamate (359 mg, 1.04 mmol) according to the method described in example 7, step 4 as light yellow solid (273 mg, 969 μmol, 93.2%). MS: M=246.2 (M–HCl+H)+

Step 3: 4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide The product was obtained starting from intermediate A-1 (30 mg, 143 μmol) and 2-(1-(2-methoxyethyl)-4-phenyl-1H-imidazol-2-yl)ethanamine hydrochloride (56.5 mg, 201 μmol) according to the method described in example 7, step 5 using 8 equivalents of N,N-diisopropylethylamine and performing a 2nd purification by flash chromatography (using silica gel amine phase and a MeOH/ethyl acetate gradient) as colorless semisolid material (20.3 mg, 46.5 μmol, 32.4%). MS: M=437.3 (M+H)+

Example 33

5-(Azetidine-1-carbonyl)-2,3-dimethyl-3H-imidazole-4-carboxylic acid [2-(1-methyl-4-phenyl-1H-imidazol-2-yl)-ethyl]-amide

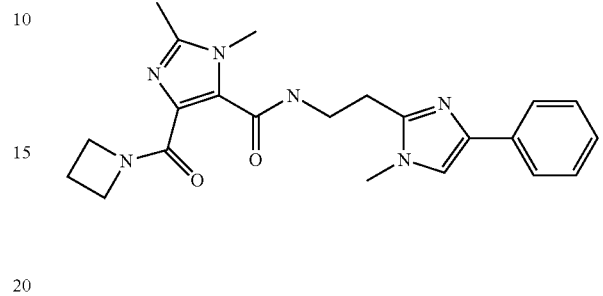

Step 1: 1,2-Dimethyl-5-(2-(1-methyl-4-phenyl-1H-imidazol-2-yl)ethylcarbamoyl)-1H-imidazole-4-carboxylic acid methyl ester The product was obtained starting from 1,2-dimethyl-1H-imidazole-4,5-dicarboxylic acid 4-methyl ester (100 mg, 505 μmol; example 8, steps 1-2) and 2-(1-methyl-4-phenyl-1H-imidazol-2-yl)ethanamine dihydrochloride (152 mg, 555 μmol; example 7, steps 1-4) according to the method described in example 10, step 5 after stirring at 70° C. for 16 h, aqueous workup and purification as light yellow oil (111 mg, 291 μmol, 57.7%). MS: M=382.4 (M+H)+

Step 2: 1,2-Dimethyl-5-(2-(1-methyl-4-phenyl-1H-imidazol-2-yl)ethylcarbamoyl)-1H-imidazole-4-carboxylic acid The product was obtained starting from 1,2-dimethyl-5-(2-(1-methyl-4-phenyl-1H-imidazol-2-yl)ethylcarbamoyl)-1H-imidazole-4-carboxylic acid methyl ester (110 mg, 288 μmol) according to the method described in example 8, step 4 as colorless foam (60 mg, 163 μmol, 56.6%). MS: M=368.2 (M+H)+

Step 3: 5-(Azetidine-1-carbonyl)-2,3-dimethyl-3H-imidazole-4-carboxylic acid [2-(1-methyl-4-phenyl-1H-imidazol-2-yl)-ethyl]-amide To a solution of 1,2-dimethyl-5-(2-(1-methyl-4-phenyl-1H-imidazol-2-yl)ethylcarbamoyl)-1H-imidazole-4-carboxylic acid (30 mg, 81.7 μmol) in DMF (1 mL) were added under nitrogen atmosphere at 0-5° C. (1-cyano-2-ethoxy-2-oxoethylidenaminooxy)dimethylamino-morpholino-carbenium hexafluorophosphate (COMU; 38.5 mg, 89.8 μmol) and N,N-diisopropylethylamine (14.3 μL, 81.7 μmol). After stirring for 5 min, azetidine (6.18 μL, 89.8 μmol) and N,N-diisopropylethylamine (14.3 μL, 81.7 μmol) were added, the ice bath was removed after additional 10 min and the reaction mixture was stirred at RT for 2 h. The product was obtained after purification by preparative HPLC using an acetonitrile/water (containing 0.1% formic acid) gradient as colorless waxy solid (1.9 mg, 4.67 μmol, 5.72%). MS: M=407.4 (M+H)+

Example 34

4-(Azetidine-1-carbonyl)-2-methyl-2H-pyrazole-3-carboxylic acid {2-[2-(2-methoxy-ethyl)-5-phenyl-2H-[1,2,4]triazol-3-yl]-ethyl}-amide

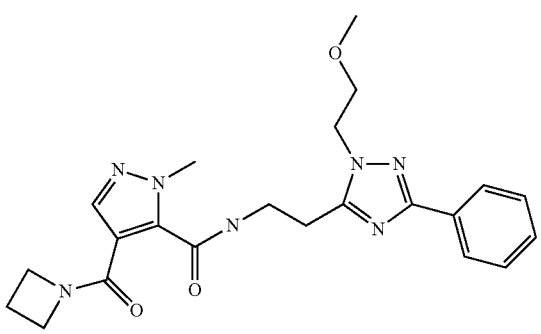 [SMILES: COCCn1nc(-c2ccccc2)nc1CCNC(=O)c1c(C(=O)N2CCC2)cnn1C]

Step 1: tert-Butyl 2-(1-(2-methoxyethyl)-3-phenyl-1H-1,2,4-triazol-5-yl)ethylcarbamate 5-[2-Bis(tert-butoxycarbonyl)aminoethyl]-3-phenyl-[1,2,4]triazole (96 mg, 247 µmol; example 22, step 1) and potassium carbonate (85.4 mg, 618 µmol) were combined with DMF (1 mL) and the mixture was stirred for 30 min at RT. 1-Bromo-2-methoxyethane (34.3 mg, 23.2 µL, 247 µmol) was added and the mixture was stirred at 60° C. for 16 h. The reaction mixture was cooled down to RT, a second portion of 1-bromo-2-methoxyethane (34.3 mg, 23.2 µL, 247 µmol) and potassium carbonate (34.2 mg, 247 µmol) were added and the mixture was stirred at 60° C. for another 4 h. The reaction mixture was poured into ethyl acetate (25 mL) and the organic phase was washed with water (3×10 mL) and brine (1×15 mL). The aqueous layers were back-extracted with ethyl acetate (1×25 mL). The organic layers were dried over MgSO4 and concentrated in vacuo to give 120 mg crude product. The product was obtained after purification by flash chromatography (using silica gel and an ethyl acetate/heptane gradient) as colorless oil (29 mg, 83.7 µmol, 33.9%).

MS: M=347.2 (M+H)+

Step 2: 2-(1-(2-Methoxyethyl)-3-phenyl-1H-1,2,4-triazol-5-yl)ethanamine hydrochloride The product was obtained starting from tert-butyl 2-(1-(2-methoxyethyl)-3-phenyl-1H-1,2,4-triazol-5-yl)ethylcarbamate (29 mg, 83.7 µmol) according to the method described in example 15, step 3 as white solid (27.2 mg, 81.8 µmol, 97.7%).

MS: M=247.2 (M−HCl+H)+

Step 3: 4-(Azetidine-1-carbonyl)-2-methyl-2H-pyrazole-3-carboxylic acid {2-[2-(2-methoxy-ethyl)-5-phenyl-2H-[1,2,4]triazol-3-yl]-ethyl}-amide The product was obtained starting from intermediate A-1 (12.6 mg, 60.2 µmol) and 2-(1-(2-methoxyethyl)-3-phenyl-1H-1,2,4-triazol-5-yl)ethanamine hydrochloride (26.0 mg, 78.3 µmol) according to the method described in example 3 as colorless oil (15.2 mg, 34.7 µmol, 57.7%).

MS: M=438.3 (M+H)+

Example 35

4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide

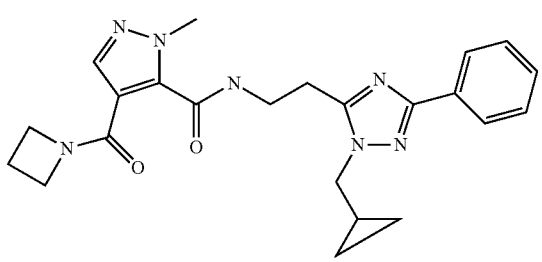 [SMILES: Cn1ncc(C(=O)N2CCC2)c1C(=O)NCCc1nc(-c2ccccc2)nn1CC1CC1]

Step 1: tert-Butyl 2-(1-(cyclopropylmethyl)-3-phenyl-1H-1,2,4-triazol-5-yl)ethylcarbamate The product was obtained starting from 5-[2-bis(tert-butoxycarbonyl)aminoethyl]-3-phenyl-[1,2,4]triazole (250 mg, 644 µmol, example 22, step 1) and (bromomethyl)cyclopropane (104 mg, 73.9 µL, 772 µmol) according to the method described in example 34, step 1 as colorless oil (69 mg, 201 µmol, 31.3%).

MS: M=343.3 (M+H)+

Step 2: 2-(1-(Cyclopropylmethyl)-3-phenyl-1H-1,2,4-triazol-5-yl)ethanamine hydro-chloride The product was obtained starting from tert-butyl 2-(1-(cyclopropylmethyl)-3-phenyl-1H-1,2,4-triazol-5-yl)ethylcarbamate (67 mg, 196 µmol) according to the method described in example 15, step 3 as colorless solid (59 mg, 190 µmol, 97.3%).

MS: M=243.4 (M−HCl+H)+

Step 3: 4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide The product was obtained starting from intermediate A-1 (30 mg, 143 µmol) and 2-(1-(cyclopropylmethyl)-3-phenyl-1H-1,2,4-triazol-5-yl)ethanamine hydrochloride (53.3 mg, 172 µmol) according to the method described in example 3 as light brown solid (34 mg, 78.4 µmol, 54.7%).

MS: M=434.3 (M+H)+

Example 36

4-(Azetidine-1-carbonyl)-2-methyl-2H-pyrazole-3-carboxylic acid [2-(5-phenyl-2H-[1,2,4]triazol-3-yl)-ethyl]-amide

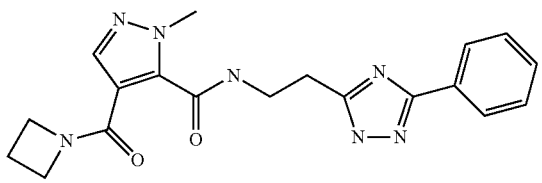 [SMILES: Cn1ncc(C(=O)N2CCC2)c1C(=O)NCCc1nc(-c2ccccc2)n[nH]1]

The product was obtained starting from intermediate A-1 (30 mg, 143 µmol) and 2-(3-phenyl-1H-1,2,4-triazol-5-yl)ethanamine trihydrochloride (53.9 mg, 172 µmol) according to the method described in example 3 as light brown solid (29 mg, 76.4 µmol, 53.3%).

MS: M=380.3 (M+H)+

Example 37

2-Methyl-4-(morpholine-4-carbonyl)-2H-pyrazole-3-carboxylic acid [2-(5-methyl-2-phenyl-oxazol-4-yl)-ethyl]-amide

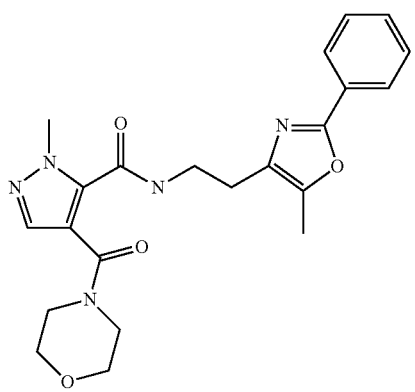 [SMILES: Cc1oc(-c2ccccc2)nc1CCNC(=O)c1c(C(=O)N2CCOCC2)cnn1C]

Step 1: Ethyl 1-methyl-5-(2-(5-methyl-2-phenyloxazol-4-yl)ethylcarbamoyl)-1H-pyrazole-4-carboxylate To a suspension of 4-(ethoxycarbonyl)-1-methyl-1H-pyrazole-5-carboxylic acid (500 mg, 2.52 mmol, prepared as described in US 2011/0071128) in THF (12.5 mL) were added 2-(5-methyl-2-phenyloxazol-4-yl)ethanamine hydrochloride (602 mg, 2.52 mmol), 1-propanephosphonic acid cyclic anhydride (4.01 g, 3.75 mL, 6.31 mmol) and N,N-diisopropylethylamine (2.61 g, 3.53 mL, 20.2 mmol) at RT. The mixture was stirred at 70° C. for 2 h, poured into KHSO4 (10% aqueous solution, 50 mL) and extracted with ethyl acetate (2×75 mL). The organic phases were washed with water (50 mL) and brine (50 mL). The combined organic layer was dried over MgSO4 and concentrated in vacuo to give 735 mg crude product. The product was obtained after purification by flash chromatography (using silica gel and an ethyl acetate/heptane gradient) as white solid (410 mg, 1.07 mmol, 42.5%).

MS: M=383.2 (M+H)+

Step 2: 1-Methyl-5-(2-(5-methyl-2-phenyloxazol-4-yl)ethylcarbamoyl)-1H-pyrazole-4-carboxylic acid To a solution of ethyl 1-methyl-5-(2-(5-methyl-2-phenyloxazol-4-yl)ethylcarbamoyl)-1H-pyrazole-4-carboxylate (407 mg, 1.06 mmol) in THF (3.00 mL) and Ethanol (1.5 mL) was added LiOH (1M aqueous solution, 2.13 mL, 2.13 mmol) at 0-5° C. The reaction mixture was stirred at RT for 2 h and poured into HCl (1 M, 2.15 mL). The resulting thick suspension was filtered and the filtrate was extracted with dichloromethane (3×50 mL). The organic layers were combined, dried over MgSO4 and concentrated in vacuo to give 341 mg (90.4%) off-white solid as crude product which was used without any further purification.

MS: M=355.2 (M+H)+

Step 3: 2-Methyl-4-(morpholine-4-carbonyl)-2H-pyrazole-3-carboxylic acid [2-(5-methyl-2-phenyl-oxazol-4-yl)-ethyl]-amide To a suspension of 1-methyl-5-(2-(5-methyl-2-phenyloxazol-4-yl)ethylcarbamoyl)-1H-pyrazole-4-carboxylic acid (40 mg, 113 µmol) in DMF (1 mL) were added COMU (58.0 mg, 135 µmol) and N,N-diisopropylethylamine (14.6 mg, 19.7 µL, 113 µmol) at 0-5° C. After 10 min the suspension became a clear solution and subsequently morpholine (11.8 mg, 135 µmol) and N,N-diisopropylethylamine (14.6 mg, 19.7 µL, 113 µmol) were added. The ice bath was removed after 10 min and the mixture was stirred at RT for 3 h. The product was obtained after purification by preparative HPLC using an acetonitrile/water (containing 0.1% formic acid) gradient as off-white waxy solid (31 mg, 73.2 µmol, 64.9%).

MS: M=424.2 (M+H)+

Example 38

2-Methyl-4-(pyrrolidine-1-carbonyl)-2H-pyrazole-3-carboxylic acid [2-(5-methyl-2-phenyl-oxazol-4-yl)-ethyl]-amide

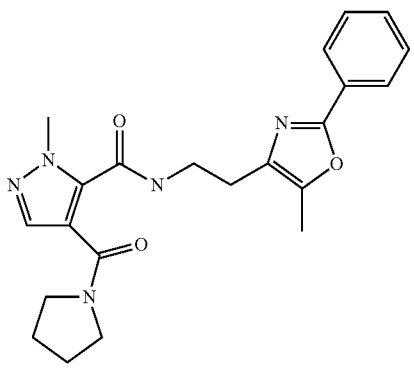 [SMILES: Cc1oc(-c2ccccc2)nc1CCNC(=O)c1c(C(=O)N2CCCC2)cnn1C]

The product was obtained starting from 1-methyl-5-(2-(5-methyl-2-phenyloxazol-4-yl)ethylcarbamoyl)-1H-pyrazole-4-carboxylic acid (40 mg, 113 µmol) and pyrrolidine (8.03 mg, 9.34 µL, 113 µmol) according to the method described in example 37, step 3 as off-white solid (22.1 mg, 54.2 µmol, 48.0%).

MS: M=408.4 (M+H)+

Example 39

4-(3-Fluoro-azetidine-1-carbonyl)-2-methyl-2H-pyrazole-3-carboxylic acid [2-(5-methyl-2-phenyl-oxazol-4-yl)-ethyl]-amide

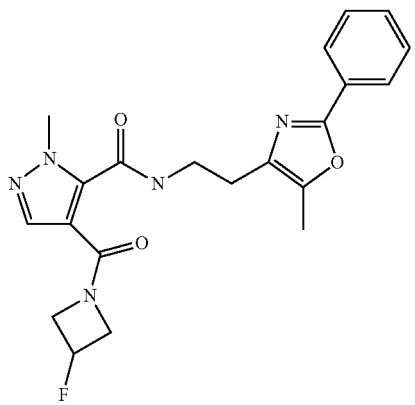 [SMILES: Cc1oc(-c2ccccc2)nc1CCNC(=O)c1c(C(=O)N2CC(F)C2)cnn1C]

The product was obtained starting from 1-methyl-5-(2-(5-methyl-2-phenyloxazol-4-yl)ethylcarbamoyl)-1H-pyrazole-4-carboxylic acid (40 mg, 113 µmol) and 3-fluoroazetidine hydrochloride (15.1 mg, 135 µmol) according to the method described in example 37, step 3 as white solid (39 mg, 94.8 µmol, 84.0%).

MS: M=412.2 (M+H)+

Example 40

2-Methyl-2H-pyrazole-3,4-dicarboxylic acid 4-(cyclopropyl-methyl-amide) 3-{[2-(5-methyl-2-phenyl-oxazol-4-yl)-ethyl]-amide}

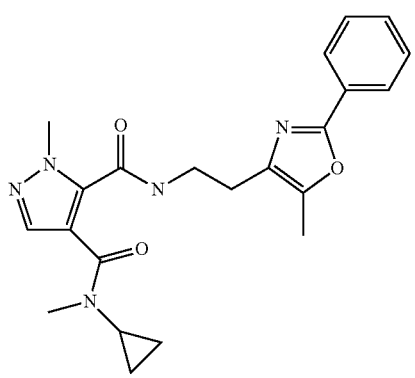 [SMILES: Cc1oc(-c2ccccc2)nc1CCNC(=O)c1c(C(=O)N(C)C2CC2)cnn1C]

The product was obtained starting from 1-methyl-5-(2-(5-methyl-2-phenyloxazol-4-yl)ethylcarbamoyl)-1H-pyrazole-4-carboxylic acid (40 mg, 113 µmol) and N-methylcyclopropanamine (9.63 mg, 135 µmol) according to the method described in example 37, step 3 as colorless oil (35.5 mg, 87.1 µmol, 77.2%).

MS: M=408.4 (M+H)+

Example 41

2-Methyl-4-(2-oxa-6-aza-spiro[3.3]heptane-6-carbonyl)-2H-pyrazole-3-carboxylic acid [2-(5-methyl-2-phenyl-oxazol-4-yl)-ethyl]amide

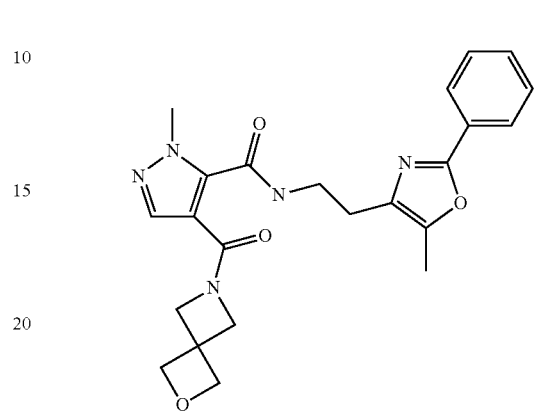

The product was obtained starting from 1-methyl-5-(2-(5-methyl-2-phenyloxazol-4-yl)ethylcarbamoyl)-1H-pyrazole-4-carboxylic acid (40 mg, 113 µmol) and 2-oxa-6-azaspiro[3.3]heptane hemioxalate (32.5 mg, 112.9 µmol) according to the method described in example 37, step 3 after purification by flash chromatography (using silica gel and an ethyl acetate/heptane gradient) as light yellow solid (24.6 mg, 50%).

MS: M=436.2 (M+H)+

Example 42

2-Methyl-4-(thiomorpholine-4-carbonyl)-2H-pyrazole-3-carboxylic acid [2-(5-methyl-2-phenyl-oxazol-4-yl)-ethyl]-amide

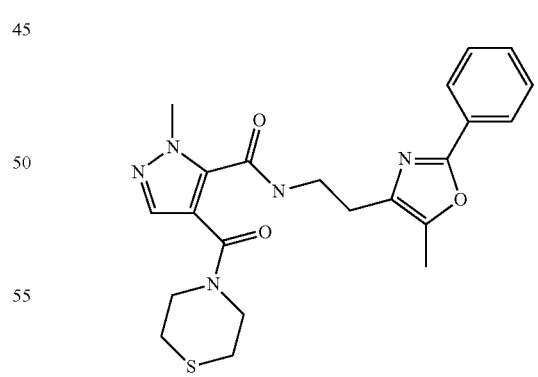

The product was obtained starting from 1-methyl-5-(2-(5-methyl-2-phenyloxazol-4-yl)ethylcarbamoyl)-1H-pyrazole-4-carboxylic acid (40 mg, 113 µmol) and thiomorpholine (14.4 mg, 14.3 µL, 135 µmol) according to the method described in example 37, step 3 as colorless oil (41.7 mg, 94.9 µmol, 84.0%).

MS: M=440.3 (M+H)+

Example 43

4-(Azetidine-1-carbonyl)-2-methyl-2H-pyrazole-3-carboxylic acid [2-(5-methyl-2-phenyl-thiazol-4-yl)-ethyl]-amide

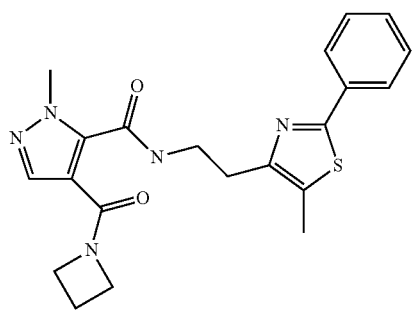 [SMILES: Cc1sc(-c2ccccc2)nc1CCNC(=O)c1c(C(=O)N2CCC2)cnn1C]

Step 1: 4-(2-Azidoethyl)-5-methyl-2-phenylthiazole

To a brown solution of 2-(5-methyl-2-phenylthiazol-4-yl) ethyl methanesulfonate (200 mg, 673 μmol; prepared according to WO 2001/021602) in DMF (2.5 mL) was added sodium azide (52.5 mg, 807 μmol) at RT. The mixture was heated to 60° C. and stirred for 3 h and was then allowed to slowly cool down to RT. The reaction mixture was poured into ethyl acetate (50 mL) and the organic phase was washed with water (3×25 mL) and brine (1×25 mL). The aqueous layers were back-extracted with ethyl acetate (1×50 mL). The combined organic layer was dried over MgSO4 and concentrated in vacuo to give 174 mg crude product. The product was obtained after purification by flash chromatography (using silica gel and an ethyl acetate/heptane gradient) as colorless oil (107 mg, 438 μmol, 65.1%).

MS: M=245.2 (M+H)+

Step 2: 2-(5-Methyl-2-phenylthiazol-4-yl)ethanamine 4-(2-Azidoethyl)-5-methyl-2-phenylthiazole (104 mg, 426 μmol) was combined with triphenylphosphine (123 mg, 468 μmol) and water (1 drop, 4 μL, 222 μmol) at RT. The reaction mixture was stirred at RT overnight and the solvent was removed in vacuo to give a light brown residue. The product was obtained after purification by flash chromatography (using silica gel and a 1M ammonia in methanol/dichloromethane gradient) as colorless semisolid (72.3 mg, 331 μmol, 77.8%).

MS: M=219.2 (M+H)+

Step 3: 4-(Azetidine-1-carbonyl)-2-methyl-2H-pyrazole-3-carboxylic acid [2-(5-methyl-2-phenyl-thiazol-4-yl)-ethyl]-amide The product was obtained starting from intermediate A-1 (30 mg, 143 μmol) and 2-(5-methyl-2-phenylthiazol-4-yl) ethanamine (31.3 mg, 143 μmol) according to the method described in example 7, step 5 after purification by preparative HPLC using an acetonitrile/water (containing 0.1% formic acid) gradient as white solid (36 mg, 87.9 μmol, 61.3%).

MS: M=410.2 (M+H)+

Example 44

4-(Azetidine-1-carbonyl)-2-methyl-2H-pyrazole-3-carboxylic acid [2-(5-methyl-3-phenyl-[1,2,4]triazol-1-yl)-ethyl]-amide

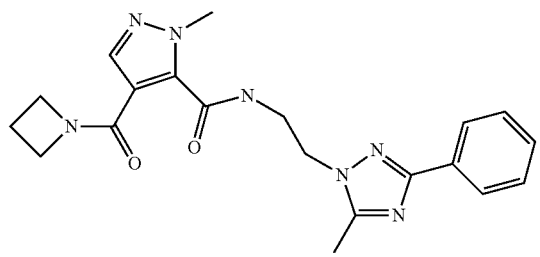 [SMILES: Cc1nc(-c2ccccc2)nn1CCNC(=O)c1c(C(=O)N2CCC2)cnn1C]

Step 1: 5-Methyl-3-phenyl-1H-1,2,4-triazole

To a suspension of ethyl benzimidate hydrochloride (2.0 g, 10.8 mmol) in EtOH (10 mL) was added sodium ethoxide (3.49 g, 4 mL, 10.8 mmol) at RT. The precipitated NaCl was filtrated off and washed with EtOH (14 mL). The filtrate was charged with acetohydrazide (880 mg, 11.9 mmol) and stirred at RT for 6 d. The crude reaction mixture was concentrated in vacuo. The crude product was suspended in NaOH (1M aqueous solution, 50 mL) and extracted with tert-butyl methyl ether (100 mL). The organic layer was washed with water (50 mL) and the aqueous layers were back-extracted with tert-butyl methyl ether (50 mL). After addition of dry ice to adjust the pH to 7, the organic layer appeared to contain almost no product and was discarded. The aqueous layer was adjusted to pH=7 by addition of HCl (25% aqueous solution) and extracted with dichloromethane (6×50 mL). The combined organic layer was dried over MgSO4 and concentrated in vacuo. The product was obtained after purification by flash chromatography (using silica gel and an ethyl acetate/hexane gradient) as white solid (154 mg, 9%).

MS: M=160.1 (M+H)+

Step 2: tert-Butyl 2-(5-methyl-3-phenyl-1H-1,2,4-triazol-1-yl)ethylcarbamate 5-Methyl-3-phenyl-1H-1,2,4-triazole (120 mg, 754 μmol) was dissolved in DMF (2.4 mL) and potassium carbonate (208 mg, 1.51 mmol) was added. After 20 min tert-butyl 2-bromoethylcarbamate (186 mg, 829 μmol) was added at 0-5° C. and the reaction mixture was stirred at RT for 25 h. The reaction mixture was extracted with ethyl acetate (30 mL) and washed with water (3×50 mL). The aqueous layers were back-extracted with ethyl acetate (20 mL) and the combined organic layer was dried over MgSO4 and concentrated in vacuo. The product was obtained after purification by flash chromatography (using silica gel and an ethyl acetate/heptane gradient) as white solid (237 mg, 784 μmol, 83.2%).

MS: M=303.2 (M+H)+

Step 3: 2-(5-Methyl-3-phenyl-1H-1,2,4-triazol-1-yl)ethanamine hydrochloride tert-Butyl 2-(5-methyl-3-phenyl-1H-1,2,4-triazol-1-yl)ethylcarbamate (235 mg, 777 μmol) was suspended in HCl (4M in dioxane, 2.5 mL, 10.0 mmol) and stirred at RT for 2 h. The suspension was poured into diethyl ether (3 mL) and filtered. The obtained crystals were washed with diethyl ether (2 mL) and dried. The white crystals (193 mg, 777 μmol, 100%) were used without any further purification for the next step.

MS: M=203.2 (M−HCl+H)+

Step 4: 4-(Azetidine-1-carbonyl)-2-methyl-2H-pyrazole-3-carboxylic acid [2-(5-methyl-3-phenyl-[1,2,4]triazol-1-yl)-ethyl]-amide The product was obtained starting from intermediate A-1 (40 mg, 191 μmol) and 2-(5-methyl-3-phenyl-1H-1,2,4-triazol-1-yl)ethanamine hydrochloride (50.2 mg, 210 μmol) according to the method described in example 43, step 3 and additional purification by flash chromatography (using silica gel and an ethyl acetate/methanol gradient) as light yellow semisolid (27.1 mg, 36%)
MS: M=394.2 (M+H)+

Example 45

4-(Azetidine-1-carbonyl)-2-methyl-2H-pyrazole-3-carboxylic acid [2-(2-benzyl-5-phenyl-2H-[1,2,4]triazol-3-yl)-ethyl]-amide

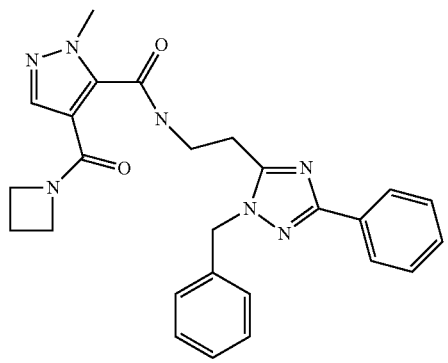 [SMILES: Cn1ncc(C(=O)N2CCC2)c1C(=O)NCCc1nc(-c2ccccc2)nn1Cc1ccccc1]

Step 1: 5-[2-Bis(tert-butoxycarbonyl)aminoethyl]-1-benzyl-3-phenyl-[1,2,4]triazole and tert-butyl 2-(1-benzyl-3-phenyl-1H-1,2,4-triazol-5-yl)ethylcarbamate To a solution of 5-[2-bis(tert-butoxycarbonyl)aminoethyl]-3-phenyl-[1,2,4]triazole (232 mg, 597 μmol; example 22, step 1) in DMF (2.83 mL) was added sodium hydride (55%, 25 mg, 574 μmol) at 0-5° C. The resulting suspension was stirred for 30 min. Then benzylbromide (102 mg, 71 μL, 597 μmol) was added at 0-5° C. and after 45 min the ice bath was removed and stirring was continued for 1 h. The reaction mixture was extracted with ethyl acetate (40 mL) and washed with water (3×20 mL) and brine (1×20 mL). The aqueous layers were back-extracted with ethyl acetate (40 mL) and the combined organic layer was dried over MgSO4 and concentrated in vacuo. The crude material was purified by flash chromatography (using silica gel and an ethyl acetate/heptane gradient) to obtain 5-[2-bis(tert-butoxycarbonyl)aminoethyl]-1-benzyl-3-phenyl-[1,2,4]triazole (115 mg, 240 μmol, 73.2%, MS: M=479.3 (M+H)+) and tert-butyl 2-(1-benzyl-3-phenyl-1H-1,2,4-triazol-5-yl)ethylcarbamate (43 mg, 114 μmol, 34.6%, MS: M=379.4 (M+H)+) both as colorless oils which were combined for the next step.

Step 2: 2-(1-benzyl-3-phenyl-1H-1,2,4-triazol-5-yl)ethanamine hydrochloride A solution of 5-[2-bis(tert-butoxycarbonyl)aminoethyl]-1-benzyl-3-phenyl-[1,2,4]triazole (103 mg, 215 μmol) and tert-butyl 2-(1-benzyl-3-phenyl-1H-1,2,4-triazol-5-yl)ethylcarbamate (38.5 mg, 102 μmol) in HCl (4M in Dioxane, 3 mL, 12.0 mmol) was stirred at RT for 1 h. The reaction mixture was concentrated in vacuo and the resulting solid was poured on diethyl ether (2.5 mL), filtrated off and washed with little diethyl ether. The obtained white crystals were dried (74 mg, 74%) and used without further purification for the next step.
MS: M=279.3 (M+H)+

Step 3: 4-(Azetidine-1-carbonyl)-2-methyl-2H-pyrazole-3-carboxylic acid [2-(2-benzyl-5-phenyl-2H-[1,2,4]triazol-3-yl)-ethyl]-amide The product was obtained starting from intermediate A-1 (40 mg, 191 μmol) and 2-(1-benzyl-3-phenyl-1H-1,2,4-triazol-5-yl)ethanamine hydrochloride (66.2 mg, 210 μmol) according to the method described in example 43, step 3 as colorless solid (40 mg, 85.2 μmol, 44.6%).
MS: M=470.4 (M+H)+

Example 46

4-(Azetidine-1-carbonyl)-2-methyl-2H-pyrazole-3-carboxylic acid [2-(5-methyl-2-p-tolyl-thiazol-4-yl)-ethyl]-amide

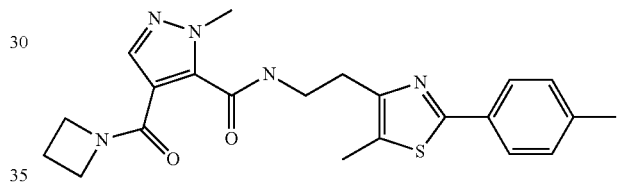

Step 1: 2-(5-Methyl-2-p-tolylthiazol-4-yl)ethyl methanesulfonate

To a yellow solution of 2-(5-methyl-2-p-tolylthiazol-4-yl)ethanol (200 mg, 857 μmol) in dichloromethane (3 mL) was added N,N-diisopropylethylamine (166 mg, 225 μL, 1.29 mmol) at RT. Methanesulfonyl chloride (113 mg, 76.8 μL, 986 μmol) was added at 0-5° C. and stirring was continued for 4 h at 0° C. The reaction mixture was poured into ethyl acetate (25 mL) and extracted with KHSO4 (10% aqueous solution, 15 mL). The organic phase was washed with water (2×15 mL) and brine (1×20 mL). The aqueous layers were back-extracted with ethyl acetate (1×25 mL) and the combined organic layer was dried over MgSO4 and concentrated in vacuo to give 280 mg (99%) of yellow oil which was used without further purification for the next step.
MS: M=312.2 (M+H)+

Step 2: 4-(2-Azidoethyl)-5-methyl-2-p-tolylthiazole

The product was obtained starting from 2-(5-methyl-2-p-tolylthiazol-4-yl)ethyl methanesulfonate (271 mg, 827 μmol) according to the method described in example 43, step 1 as colorless oil (163 mg, 631 μmol, 76.3%).
MS: M=259.1 (M+H)+

Step 3: 2-(5-methyl-2-p-tolylthiazol-4-yl)ethanamine 4-(2-Azidoethyl)-5-methyl-2-p-tolylthiazole (160 mg, 619 μmol), triphenylphosphine polymer bound (270 mg, 803

μmol) and water (2 drops, 8 μL, 444 μmol) were combined at RT to give a brown suspension. The mixture was stirred at RT overnight. The suspension was filtered and the liquid was evaporated to give the product as light yellow oil (151 mg, 617 μmol, 99.7%) which was used without further purification for the next step.

MS: M=233.2 (M+H)+

Step 4: 4-(Azetidine-1-carbonyl)-2-methyl-2H-pyrazole-3-carboxylic acid [2-(5-methyl-2-p-tolyl-thiazol-4-yl)-ethyl]-amide The product was obtained starting from intermediate A-1 (30 mg, 143 μmol) and 2-(5-methyl-2-p-tolylthiazol-4-yl)ethanamine (35.1 mg, 143 μmol) according to the method described in example 43, step 3 as white solid (41 mg, 96.8 μmol, 67.5%).

MS: M=424.3 (M+H)+

Example 47

4-(Azetidine-1-carbonyl)-2-methyl-2H-pyrazole-3-carboxylic acid [2-(4-methyl-1-phenyl-1H-pyrazol-3-yl)-ethyl]-amide

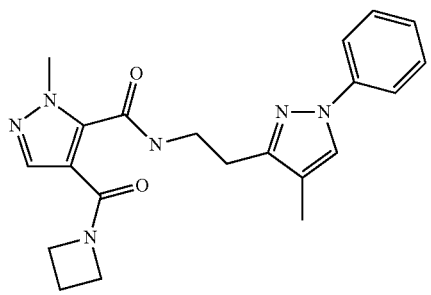 [SMILES: Cc1cn(-c2ccccc2)nc1CCNC(=O)c1c(C(=O)N2CCC2)cnn1C]

Step 1: (E)-1,1,1-Trichloro-4-ethoxy-3-methylbut-3-en-2-one

To a solution of 2,2,2-trichloroacetyl chloride (10.6 g, 6.52 mL, 58.1 mmol) in dichloromethane (15 mL) cooled to −10° C. was added a mixture of (E)-1-ethoxyprop-1-ene (5 g, 6.43 mL, 58.1 mmol) and pyridine (4.59 g, 4.7 mL, 58.1 mmol) over a period of 15 min. After the addition was complete, the mixture was stirred at RT for 16 h. The resulting precipitate was filtered and washed with dichloromethane. The filtrate was concentrated in vacuo and dried at 40° C. in high vacuum to give the product as brown semisolid (16.1 g with 80% purity, 95.8%). The crude material was used directly in the next step without any further purification.

Step 2: Ethyl 4-methyl-1-phenyl-1H-pyrazole-3-carboxylate

A mixture of (E)-1,1,1-trichloro-4-ethoxy-3-methylbut-3-en-2-one (16.1 g with 80% purity, 55.6 mmol) and phenylhydrazine (8.09 g, 7.36 mL, 71.0 mmol) in ethanol (70 mL) was refluxed for 4 h. The reaction mixture was poured into dichloromethane (150 mL) and extracted with HCl (1 M, 1×75 mL). The organic phase was washed water (1×75 mL) and the aqueous layers were back-extracted with dichloromethane (1×150 mL). The combined organic layer was dried over MgSO4 and concentrated in vacuo to give 11.94 g crude product. The product was obtained after purification by flash chromatography (using silica gel and an ethyl acetate/heptane gradient) as brown oil (1.51 g, 6.56 mmol, 11.1%)

MS: M=231.2 (M+H)+

Step 3: (4-Methyl-1-phenyl-1H-pyrazol-3-yl)methanol

To a solution of ethyl 4-methyl-1-phenyl-1H-pyrazole-3-carboxylate (100 mg, 434 μmol) in toluene (1 mL) cooled to −78° C. was added dropwise DIBAL-H (1M solution in toluene, 868 μL, 868 μmol) keeping the temperature below −68° C. The reaction mixture was stirred at −78° C. for 30 min and at −15° C. for 1 h. At that temperature, KHSO4 (10% aqueous solution, 10 mL) was added dropwise and the resulting reaction mixture was extracted with ethyl acetate (2×50 mL). The organic phases were washed with water (1×30 mL) and brine (1×20 mL). The combined organic layer was dried over MgSO4 and concentrated in vacuo to give 112 mg crude material. The product was obtained after purification by flash chromatography (using silica gel and an ethyl acetate/heptane gradient) as yellow viscous oil (52 mg, 276 μmol, 63.6%).

MS: M=189.3 (M+H)+

Step 4: 3-(Bromomethyl)-4-methyl-1-phenyl-1H-pyrazole

To a solution of (4-methyl-1-phenyl-1H-pyrazol-3-yl)methanol (158 mg, 0.84 mmol) and triphenylphosphine polymer bound (422 mg, 1.26 mmol) in dichloromethane (4.5 mL) was added carbon tetrabromide (416 mg, 1.26 mmol) at 0-5° C. The ice bath was removed after 15 min and the mixture was stirred at RT for 2 h. The mixture was filtered, washed with dichloromethane and the solvent was evaporated to give 426 mg crude material. The product was obtained after purification by flash chromatography (using silica gel and an ethyl acetate/heptane gradient) as light yellow oil (115 mg, 458 μmol, 38.3%).

MS: M=251.2 (M+H)+

Step 5: 2-(4-Methyl-1-phenyl-1H-pyrazol-3-yl)acetonitrile

A mixture of 3-(bromomethyl)-4-methyl-1-phenyl-1H-pyrazole (112 mg, 446 μmol) and potassium cyanide (33.3 mg, 491 μmol) in DMSO (2 mL) was heated to 60° C. for 2 h. The reaction mixture was cooled to RT, poured into water (25 mL) and extracted with ethyl acetate (2×50 mL). The organic phases were washed with water (3×25 mL) and brine 1×25 mL). The combined organic layer was dried over MgSO4 and concentrated in vacuo to give 99.6 mg crude material. The product was obtained after purification by flash chromatography (using silica gel and an ethyl acetate/heptane gradient) as light yellow oil (58 mg, 294 μmol, 65.9%).

MS: M=198.3 (M+H)+

Step 6: 2-(4-Methyl-1-phenyl-1H-pyrazol-3-yl)ethanamine

To lithium borohydride (2M solution in THF, 629 μL, 1.26 mmol) was added dropwise trimethylchlorosilane (273 mg, 321 μL, 2.51 mmol) over a period of 5 min at 0-5° C. At that temperature a solution of 2-(4-methyl-1-phenyl-1H-pyrazol-3-yl)acetonitrile (62 mg, 314 μmol) in THF (0.5 mL) was added dropwise. The mixture was stirred at 70° C. for 1.5 h. After cooling down to 0-5° C., MeOH (0.5 mL) was added dropwise. After 10 min the ice bath was removed and the mixture was allowed to warm up to RT. The reaction mixture was poured into NaOH (1 M, 10 mL) and extracted with dichloromethane (3×25 mL). The combined organic layer was dried over MgSO4 and concentrated in vacuo to give the product as light yellow semisolid (46 mg, 206 μmol, 65.4%) which was used without further purification for the next step.
MS: M=202.9 (M+H)+

Step 7: 4-(Azetidine-1-carbonyl)-2-methyl-2H-pyrazole-3-carboxylic acid [2-(4-methyl-1-phenyl-1H-pyrazol-3-yl)-ethyl]-amide The product was obtained starting from intermediate A-1 (43.0 mg, 206 μmol) and 2-(4-methyl-1-phenyl-1H-pyrazol-3-yl)ethanamine (46 mg, 206 μmol) according to the method described in example 43, step 3 as colorless foam (20.5 mg, 52.2 μmol, 25.4%).
MS: M=393.2 (M+H)+

Example 48

4-(Azetidine-1-carbonyl)-2-methyl-2H-pyrazole-3-carboxylic acid {2-[2-(2-ethyl-pyridin-4-yl)-5-methyl-thiazol-4-yl]-ethyl}-amide

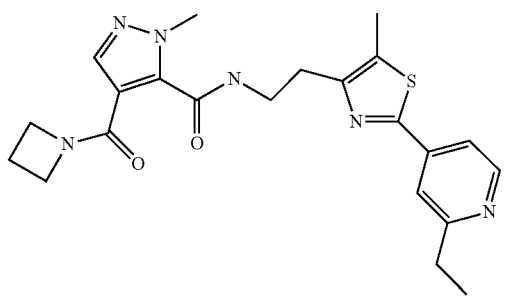 [SMILES: CCc1cc(-c2nc(CCNC(=O)c3c(C(=O)N4CCC4)cnn3C)c(C)s2)ccn1]

Step 1: 2-(2-(2-Ethylpyridin-4-yl)-5-methylthiazol-4-yl)ethyl methanesulfonate

The product was obtained starting from 2-(2-(2-ethylpyridin-4-yl)-5-methylthiazol-4-yl)ethanol (200 mg, 805 μmol, prepared as described in WO 2003/037327) and methanesulfonyl chloride (111 mg, 75.3 μL, 966 μmol) according to the method described in example 46, step 1 as yellow oil (226 mg, 692 μmol, 86%) which was used without further purification for the next step.
MS: M=327.1 (M+H)+

Step 2: 4-(2-Azidoethyl)-2-(2-ethylpyridin-4-yl)-5-methylthiazole

The product was obtained starting from 2-(2-(2-ethylpyridin-4-yl)-5-methylthiazol-4-yl)ethyl methanesulfonate (226 mg, 692 μmol) and sodium azide (63.0 mg, 969 μmol) according to the method described in example 46, step 2 as light yellow oil (138 mg, 505 μmol, 72.9%).
MS: M=274.1 (M+H)+

Step 3: 2-(2-(2-Ethylpyridin-4-yl)-5-methylthiazol-4-yl)ethanamine

The product was obtained starting from 4-(2-azidoethyl)-2-(2-ethylpyridin-4-yl)-5-methylthiazole (134 mg, 490 μmol) and triphenylphosphine polymer bound (248 mg, 735 μmol) according to the method described in example 46, step 3 as yellow oil (117 mg, 473 μmol, 96.5%).
MS: M=248.3 (M+H)+

Step 4: 4-(Azetidine-1-carbonyl)-2-methyl-2H-pyrazole-3-carboxylic acid {2-[2-(2-ethyl-pyridin-4-yl)-5-methyl-thiazol-4-yl]-ethyl}-amide The product was obtained starting from intermediate A-1 (30 mg, 143 μmol) and 2-(2-(2-ethylpyridin-4-yl)-5-methylthiazol-4-yl)ethanamine (35.5 mg, 143 μmol) according to the method described in example 43, step 3 as colorless semisolid (35 mg, 79.8 μmol, 55.7%).
MS: M=439.3 (M+H)+

Example 49

4-(Azetidine-1-carbonyl)-2-methyl-2H-pyrazole-3-carboxylic acid {2-[5-phenyl-2-(2,2,2-trifluoro-ethyl)-2H-[1,2,4]triazol-3-yl]ethyl}-amide

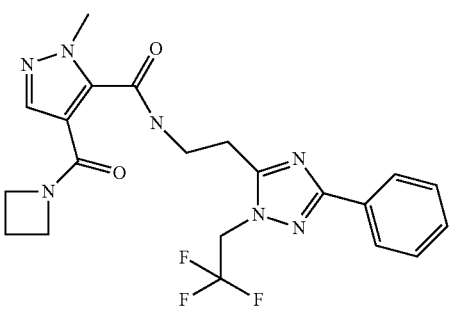 [SMILES: Cn1ncc(C(=O)N2CCC2)c1C(=O)NCCc1nc(-c2ccccc2)nn1CC(F)(F)F]

Step 1: tert-Butyl 2-(3-phenyl-1-(2,2,2-trifluoro ethyl)-1H-1,2,4-triazol-5-yl)ethylcarbamate 5-[2-Bis(tert-butoxycarbonyl)aminoethyl]-3-phenyl-[1,2,4]triazole (200 mg, 515 μmol; example 22, step 1) was dissolved in DMF (3.57 mL) and potassium carbonate (157 mg, 1.14 mmol) was added at RT. The mixture was stirred for 20 min, 2,2,2-trifluoroethyl trifluoromethanesulfonate (165 mg, 710 μmol) was added and stirring was continued at RT overnight. The reaction mixture was extracted with ethyl acetate (40 mL) and washed with water (3×20 mL) and brine (1×20 mL). The aqueous layers were back-extracted with ethyl acetate (40 mL) and the combined organic layer was dried over MgSO4 and concentrated in vacuo. The product was obtained after purification by flash chromatography (using silica gel and an ethyl acetate/heptane gradient) as white solid (140 mg, 378 μmol, 73.4%).
MS: M=371.2 (M+H)+

Step 2: 2-(3-Phenyl-1-(2,2,2-trifluoroethyl)-1H-1,2,4-triazol-5-yl)ethanamine hydrochloride The product was obtained starting from tert-butyl 2-(3-phenyl-1-(2,2,2-trifluoroethyl)-1H-1,2,4-triazol-5-yl)ethylcarbamate (133 mg, 359 μmol) according to the method described in example 45, step 2 as white solid (108 mg, 352 μmol, 98%).
MS: M=271.3 (M−HCl+H)+

Step 3: 4-(Azetidine-1-carbonyl)-2-methyl-2H-pyrazole-3-carboxylic acid {2-[5-phenyl-2-(2,2,2-trifluoro-ethyl)-2H-[1,2,4]triazol-3-yl]-ethyl}-amide The product was obtained starting from intermediate A-1 (40 mg, 191 µmol) and 2-(3-phenyl-1-(2,2,2-trifluoro ethyl)-1H-1,2,4-triazol-5-yl)ethanamine hydrochloride (65 mg, 212 µmol) according to the method described in example 43, step 3 as white solid (43 mg, 93.2 µmol, 47.5%).
MS: M=462.2 (M+H)+

Example 50

2-Methyl-4-(morpholine-4-carbonyl)-2H-pyrazole-3-carboxylic acid [2-(1-methyl-1H-benzoimidazol-2-yl)-ethyl]-amide

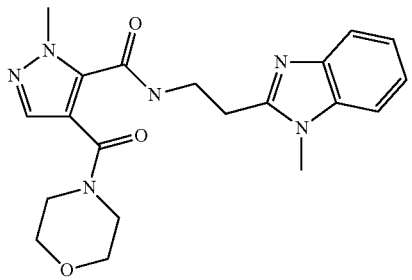 [SMILES: Cn1ncc(C(=O)N2CCOCC2)c1C(=O)NCCc1nc2ccccc2n1C]

The product was obtained starting from intermediate A-2 (40 mg, 167 µmol) and 2-(1-methyl-1H-benzo[d]imidazol-2-yl)ethanamine dihydrochloride (49.8 mg, 201 µmol) according to the method described in example 8, step 3 after purification by flash chromatography (using silica gel and an ethyl acetate/heptane gradient) as light red solid (22 mg, 55.5 µmol, 33.2%).
MS: M=397.4 (M+H)+

Example 51

2-Methyl-4-(pyrrolidine-1-carbonyl)-2H-pyrazole-3-carboxylic acid [2-(1-methyl-1-benzoimidazol-2-yl)-ethyl]-amide

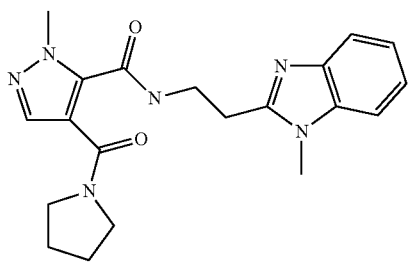 [SMILES: Cn1ncc(C(=O)N2CCCC2)c1C(=O)NCCc1nc2ccccc2n1C]

Step 1: Ethyl 1-methyl-5-(2-(1-methyl-1H-benzo[d]imidazol-2-yl)ethylcarbamoyl)-1H-pyrazole-4-carboxylate The product was obtained starting from 4-(ethoxycarbonyl)-1-methyl-1H-pyrazole-5-carboxylic acid (150 mg, 757 µmol, prepared as described in US 2011/0071128) and 2-(1-methyl-1H-benzo[d]imidazol-2-yl)ethanamine dihydrochloride (225 mg, 908 µmol) according to the method described in example 8, step 3 as red viscous oil (80 mg, 225 µmol, 29.7%).
MS: M=356.2 (M+H)+

Step 2: 1-Methyl-5-(2-(1-methyl-1H-benzo[d]imidazol-2-yl)ethylcarbamoyl)-1H-pyrazole-4-carboxylic acid To a solution of ethyl 1-methyl-5-(2-(1-methyl-1H-benzo[d]imidazol-2-yl)ethylcarbamoyl)-1H-pyrazole-4-carboxylate (76 mg, 214 µmol) in THF (0.9 mL) and ethanol (0.3 mL) was added LiOH (1M aqueous solution, 428 µL, 428 µmol) at 0-5° C. The mixture was stirred at RT for 2 h. HCl (1M aqueous solution, 0.43 mL, 0.43 mmol) was added and the precipitating product was filtered, washed with THF/water 4:1 and dried in vacuo to give the product as colorless solid (52 mg, 159 µmol, 74.3%).
MS: M=328.3 (M+H)+

Step 3: 2-Methyl-4-(pyrrolidine-1-carbonyl)-2H-pyrazole-3-carboxylic acid [2-(1-methyl-1H-benzo imidazol-2-yl)-ethyl]-amide The product was obtained starting from 1-methyl-5-(2-(1-methyl-1H-benzo[d]imidazol-2-yl)ethylcarbamoyl)-1H-pyrazole-4-carboxylic acid (25 mg, 76.4 µmol) and pyrrolidine (6.52 mg, 7.58 µL, 91.6 µmol) according to the method described in example 37, step 3 as light red solid (15 mg, 39.4 µmol, 51.6%).
MS: M=381.4 (M+H)+

Example 52

5-(Azetidine-1-carbonyl)-3-methyl-3H-[1,2,3]triazole-4-carboxylic acid [2-(1-methyl-4-phenyl-1H-imidazol-2-yl)-ethyl]-amide

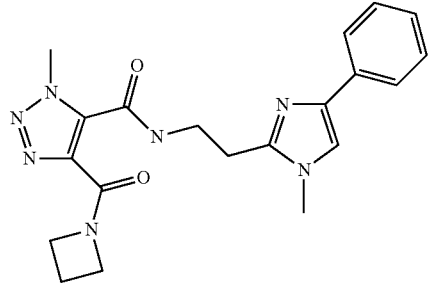 [SMILES: Cn1cc(-c2ccccc2)nc1CCNC(=O)c1c(C(=O)N2CCC2)nnn1C]

Step 1: 1-Trimethylsilanylmethyl-1H-[1, 2, 3]triazole-4,5-dicarboxylic acid dimethyl ester A solution of azidomethyl-trimethyl-silane (5.0 g, 38.69 mmol) and dimethyl acetylenedicarboxylate (4.74 mL, 38.69 mmol) in benzene (200 mL) was refluxed for 2 h. The solvent was removed in vacuo and the resultant crude material was diluted with water (100 mL), and extracted with ethyl acetate (3×100 mL). The combined organic layer was washed with brine (50 mL), dried over anhydrous Na2SO4, filtered, and evaporated in vacuo. The product was obtained after purification by flash chromatography (using silica gel and 20% ethyl acetate/hexane) as colorless liquid (10 g, 36.9 mmol, 95.2%).

MS: M=272.0 (M+H)+

Step 2: 1-Methyl-1H-[1, 2, 3]triazole-4,5-dicarboxylic acid dimethyl ester

To a solution of 1-trimethylsilanylethyl-1H-[1,2,3]triazole-4,5-dicarboxylic acid dimethyl ester (10 g, 36.9 mmol) in methanol (100 mL) was added potassium fluoride (11.07 g, 184.5 mmol) at RT. The reaction mixture was stirred at RT for 6 h. After solvent removal in vacuo, the crude material was diluted with water (100 mL) and extracted with ethyl acetate (2×150 mL). The combined organic layer was washed with water (2×50 mL) and brine (50 mL), dried over anhydrous Na2SO4, filtered, and evaporated in vacuo. The product was obtained after purification by flash chromatography (using silica gel and 30% ethyl acetate/hexane) as white solid (4.3 g, 21.6 mmol, 58.5%).

MS: M=200.2 (M+H)+

Step 3: Lithium 4-(methoxycarbonyl)-1-methyl-1H-1,2,3-triazole-5-carboxylate To a solution of 1-methyl-1H-[1,2,3]triazole-4,5-dicarboxylic acid dimethyl ester (1 g, 5.025 mmol) in THF (20 mL) and ethanol (5 mL) was added at 0° C. a solution of lithium hydroxide monohydrate (169 mg, 4.02 mmol) in water (5 mL) over a period of 10 min. The reaction mixture was allowed to stir at 0° C. for 3 h. The mixture was diluted with water (10 mL) and washed with ethyl acetate (2×50 mL). The aqueous layer was evaporated under reduced pressure and the crude material thus obtained was dried by azeotropic distillation with toluene to afford the product as white solid (0.6 g, 3.24 mmol, 64.5%).

Step 4: Methyl 1-methyl-5-(2-(1-methyl-4-phenyl-1H-imidazol-2-yl)ethylcarbamoyl)-1H-1,2,3-triazole-4-carboxylate The product was obtained starting from lithium 4-(methoxycarbonyl)-1-methyl-1H-1,2,3-triazole-5-carboxylate (150 mg, 785 µmol) and 2-(1-methyl-4-phenyl-1H-imidazol-2-yl)ethanamine dihydrochloride (226 mg, 824 µmol, example 7, step 4) according to the method described in example 7, step 5 after aqueous work-up and purification by flash chromatography (using silica gel and an ethyl acetate/heptane gradient) as light yellow solid (79 mg, 214 µmol, 27.3%).

MS: M=369.2 (M+H)+

Step 5: 1-Methyl-5-(2-(1-methyl-4-phenyl-1H-imidazol-2-yl)ethylcarbamoyl)-1H-1,2,3-triazole-4-carboxylic acid To a solution of methyl 1-methyl-5-(2-(1-methyl-4-phenyl-1H-imidazol-2-yl)ethylcarbamoyl)-1H-1,2,3-triazole-4-carboxylate (77 mg, 209 µmol) in THF (0.9 mL) and MeOH (0.3 mL) was added LiOH (1M aqueous solution, 418 µL, 418 µmol) at 0-5° C. The ice bath was removed and the mixture was stirred at RT for 4 h. HCl (1M aqueous solution, 0.42 mL, 0.42 mmol) was added and the solution was poured into dichloromethane (40 mL) to result in a suspension. The solid precipitate was filtered, washed with THF/water 4:1 and dried in vacuo to give the product as colorless solid (52 mg, 147 µmol, 70.2%).

MS: M=355.2 (M+H)+

Step 6: 5-(Azetidine-1-carbonyl)-3-methyl-3H[1,2,3]triazole-4-carboxylic acid [2-(1-methyl-4-phenyl-1H-imidazol-2-yl)-ethyl]-amide The product was obtained starting from 1-methyl-5-(2-(1-methyl-4-phenyl-1H-imidazol-2-yl)ethylcarbamoyl)-1H-1,2,3-triazole-4-carboxylic acid (30 mg, 84.7 µmol) and azetidine (6.8 mg, 8 µL, 119 µmol) according to the method described in example 37, step 3 as colorless solid (11 mg, 28 µmol, 33%).

MS: M=394.2 (M+H)+

Example 53

2-Methyl-2H-pyrazole-3,4-dicarboxylic acid 4-(cyclopropyl-methyl-amide) 3-{[2-(1-methyl-1H-benzoimidazol-2-yl)-ethyl]-amide}

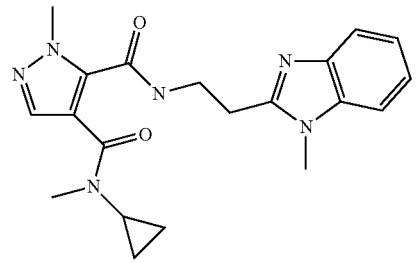 [SMILES: CN(C(=O)c1cnn(C)c1C(=O)NCCc1nc2ccccc2n1C)C1CC1]

The product was obtained starting from 1-methyl-5-(2-(1-methyl-1H-benzo[d]imidazol-2-yl)ethylcarbamoyl)-1H-pyrazole-4-carboxylic acid (25 mg, 76.4 µmol, example 51, step 2) and N-methylcyclopropanamine hydrochloride (10.4 mg, 91.6 µmol) according to the method described in example 37, step 3 after purification by preparative HPLC using an acetonitrile/water (containing 0.1% triethylamine) gradient as colorless foam (16.6 mg, 43.6 µmol, 57.1%).

MS: M=381.3 (M+H)+

Example 54

4-(Azetidine-1-carbonyl)-2-methyl-2H-pyrazole-3-carboxylic acid [2-(5-methyl-4-phenyl-thiazol-2-yl)-ethyl]-amide

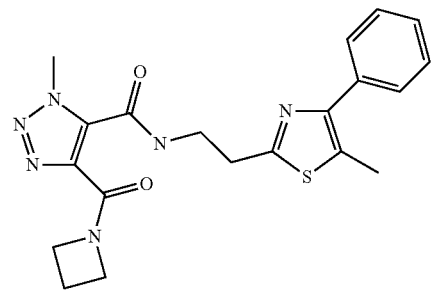 [SMILES: Cc1sc(CCNC(=O)c2c(C(=O)N3CCC3)nnn2C)nc1-c1ccccc1]

The product was obtained starting from intermediate A-1 (30 mg, 143 µmol) and 2-(5-methyl-4-phenylthiazol-2-yl)ethanamine dihydrochloride (45.9 mg, 158 µmol) according to the method described in example 43, step 3 as light yellow waxy solid (31.6 mg, 77.2 µmol, 53.8%).

MS: M=410.3 (M+H)+

Example 55

4-(Azetidine-1-carbonyl)-2-methyl-2H-pyrazole-3-carboxylic acid [2-(2,5-diphenyl-2H-[1,2,4]triazol-3-yl)-ethyl]-amide

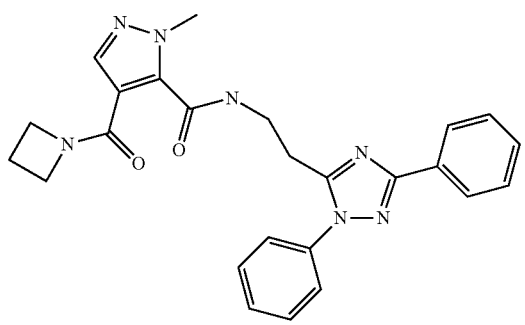 [SMILES: Cn1ncc(C(=O)N2CCC2)c1C(=O)NCCc1nc(-c2ccccc2)nn1-c1ccccc1]

Step 1: 2-Phenyloxazol-4(5H)-one

To a solution of benzoyl isocyanate (2 g, 12.2 mmol) in acetonitrile (40 mL) was added rapidly (diazomethyl)trimethylsilane (2M solution in hexane, 7.34 mL, 14.7 mmol) at 0-5° C., whereby the temperature rose to 15° C. (bubbling). The mixture was stirred at 0-5° C. for 1 h. Following solvent evaporation, the product was obtained after purification by flash chromatography (using silica gel and an ethyl acetate/heptane gradient) as yellow solid (1.84 g with 90% purity, 10.3 mmol, 84.0%) which was used without further purification for the next step.

MS: M=162.3 (M+H)+

Step 2:
(1,3-Diphenyl-1H-1,2,4-triazol-5-yl)methanol

A mixture of 2-phenyloxazol-4(5H)-one (600 mg, 3.35 mmol) and phenylhydrazine (420 mg, 382 µL, 3.69 mmol) in ethanol (10 mL) was refluxed for 2 h. The reaction mixture was concentrated in vacuo. The obtained suspension was filtered, washed with EtOH and dried in vacuo to give 513 mg of a light yellow solid which proofed to be product. The filtrate was evaporated to give 430 mg of a yellow solid which also contained a considerable amount of product. Thus, the product was obtained after purification of the evaporated filtrate by flash chromatography (using silica gel and an ethyl acetate/dichloromethane gradient) and combination with the precipitated product as light yellow solid (711 mg, 2.83 mmol, 84.4%). MS: M=252.2 (M+H)+

Step 3:
5-(Bromomethyl)-1,3-diphenyl-1H-1,2,4-triazole

To a suspension of (1,3-diphenyl-1H-1,2,4-triazol-5-yl)methanol (350 mg, 1.39 mmol) and triphenylphosphine polymer bound (679 mg, 2.02 mmol) in dichloromethane (6 mL) was added at 0-5° C. carbon tetrabromide (670 mg, 2.02 mmol). The ice bath was removed and the mixture was stirred at RT for 18 h. The suspension was filtered, washed with dichloromethane and evaporated to give 844 mg of yellow oil. The product was obtained after purification by flash chromatography (using silica gel and an ethyl acetate/heptane gradient) as colorless solid (267 mg, 850 µmol, 61.0%).

MS: M=316.0 (M+H)+

Step 4:
2-(1,3-Diphenyl-1H-1,2,4-triazol-5-yl)acetonitrile

A mixture of 5-(bromomethyl)-1,3-diphenyl-1H-1,2,4-triazole (265 mg, 843 µmol) and potassium cyanide (62.3 mg, 928 µmol) in DMSO (5 mL) was heated at 60° C. for 1.5 h. The reaction mixture was cooled to RT, poured into water (25 mL) and extracted with ethyl acetate (2×50 mL). The organic phases were washed with water (2×25 mL) and brine (1×25 mL), and the combined organic layer was dried over MgSO4 and concentrated in vacuo to give 251 mg of crude product. The product was obtained after purification by flash chromatography (using silica gel and an ethyl acetate/heptane gradient) as light yellow waxy solid (120 mg, 461 µmol, 54.7%).

MS: M=261.2 (M+H)+

Step 5:
2-(1,3-Diphenyl-1H-1,2,4-triazol-5-yl)ethanamine

To lithium borohydride (2M solution in THF, 899 µL, 1.8 mmol) was added dropwise trimethylchlorosilane (391 mg, 460 µL, 3.6 mmol) over a period of 5 min at 0-5° C., followed by the dropwise addition of a solution of 2-(1,3-diphenyl-1H-1,2,4-triazol-5-yl)acetonitrile (117 mg, 449 µmol) in THF (1.5 mL). The ice bath was removed after 10 min and the mixture was stirred at 60° C. for 1.5 h. The reaction mixture was cooled to 0-5° C. and 1 mL MeOH was added slowly (bubbling!). After 10 min the ice bath was removed and the mixture was allowed to warm up to RT. The mixture was poured into NaOH (1M aqueous solution, 15 mL) and extracted with dichloromethane (3×50 mL). The combined organic phase was dried over MgSO4, filtered and evaporated to give the product (118 mg with 90% purity, 402 µmol, 89.4%) as yellow viscous oil which was used without further purification.

MS: M=265.2 (M+H)+

Step 6: 4-(Azetidine-1-carbonyl)-2-methyl-2H-pyrazole-3-carboxylic acid [2-(2,5-diphenyl-2H-[1,2,4]triazol-3-yl)-ethyl]-amide The product was obtained starting from intermediate A-1 (30 mg, 143 µmol) and 2-(1,3-diphenyl-1H-1,2,4-triazol-5-yl)ethanamine (50.5 mg, 172 µmol) via HATU coupling according to the method described in example 1 and direct purification by preparative HPLC using an acetonitrile/water (containing 0.1% formic acid) gradient as colorless solid (36 mg, 79.0 µmol, 55.1%).

MS: M=456.5 (M+H)+

Example 56

4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide

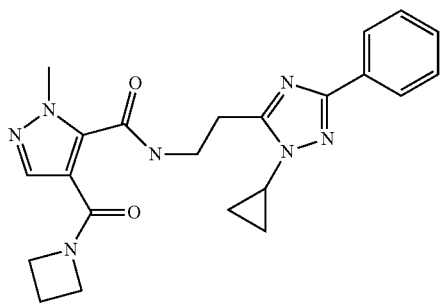 [SMILES: Cn1ncc(C(=O)N2CCC2)c1C(=O)NCCc1nc(-c2ccccc2)nn1C1CC1]

Step 1: tert-Butyl 2-(1-cyclopropyl-3-phenyl-1H-1,2,4-triazol-5-yl)ethylcarbamate A suspension of 5-[2-bis(tert-butoxycarbonyl)aminoethyl]-3-phenyl-[1,2,4]triazole (218 mg, 561 µmol, example 22, step 1), cyclopropylboronic acid (192.8 mg, 2.24 mmol) and sodium carbonate (119 mg, 1.12 mmol) in dichloroethane (4 mL) was evacuated and backfilled with argon. A hot suspension of copper (II) acetate (102 mg, 561 µmol) and 2,2'-bipyridine (87.6 mg, 561 µmol) in dichloroethane (1.5 mL) was added and the reaction mixture was stirred at 85° C. for 40 h. The reaction mixture was cooled to RT, filtered and washed with dichloromethane. The filtrate was extracted with water (2×20 mL), dried over MgSO4, filtered and evaporated to give 285 mg of green oil. The product was obtained after purification by flash chromatography (using silica gel and an ethyl acetate/heptane gradient) as colorless viscous oil (105 mg, 320 µmol, 57.0%).

MS: M=329.3 (M+H)+

Step 2: 2-(1-Cyclopropyl-3-phenyl-1H-1,2,4-triazol-5-yl)ethanamine hydrochloride tert-Butyl 2-(1-cyclopropyl-3-phenyl-1H-1,2,4-triazol-5-yl)ethylcarbamate (105 mg, 320 µmol) was dissolved in HCl (4M in dioxane, 2 mL, 8.00 mmol). The mixture was stirred at RT for 2 h. The obtained suspension was filtered, washed with diethyl ether and dried in vacuo to give the product as colorless solid (75.5 mg, 285 µmol, 89.2%) which was used without further purification for the next step.

MS: M=229.4 (M+H)+

Step 3: 4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide The product was obtained starting from intermediate A-1 (30 mg, 143 µmol) and 2-(1-cyclopropyl-3-phenyl-1H-1,2,4-triazol-5-yl)ethanamine hydrochloride (45.6 mg, 172 µmol) via HATU coupling according to the method described in example 55, step 6 as colorless solid (34 mg, 81.1 µmol, 56.5%).

MS: M=420.3 (M+H)+

Example 57

4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide

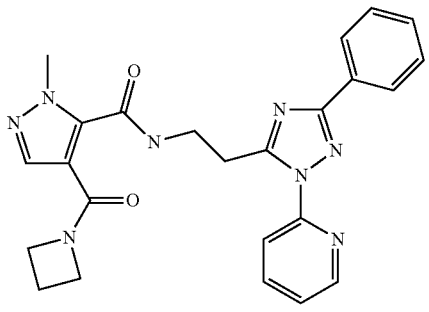 [SMILES: Cn1ncc(C(=O)N2CCC2)c1C(=O)NCCc1nc(-c2ccccc2)nn1-c1ccccn1]

Step 1: (Z)-Ethyl N-2-chloroacetylbenzimidate

To a suspension of ethyl benzimidate hydrochloride (500 mg, 2.69 mmol) in dichloroethane (25 mL) was added under argon atmosphere triethylamine (872 mg, 1.2 mL, 8.62 mmol). The stirred reaction mixture was cooled to 0° C. and chloroacetyl chloride (608 mg, 431 µL, 5.39 mmol) was added. After 30 min the cooling bath was removed and stirring was continued at RT for 4 h. After filtration the organic phase was extracted with KHSO4 (10% aqueous solution), dried and evaporated to yield the product as light brown semi-solid (740 mg with 80% purity, 2.62 mmol, 97%) which was used without further purification for the next step.

MS: M=226.1 (M+H)+

Step 2: 245-(Chloro methyl)-3-phenyl-1H-1,2,4-triazol-1-yl)pyridine

To a solution of (Z)-ethyl N-2-chloroacetylbenzimidate (160 mg, 709 µmol) in THF (5 mL) was added 2-hydrazinylpyridine (139.2 mg, 1.28 mmol) in THF (1.5 mL) at 0° C. under argon atmosphere. The resulting red-brown solution was stirred at RT overnight. The volatiles were removed and the product was obtained after purification by flash chromatography (using silica gel and an ethyl acetate/heptane gradient) as white solid (130 mg, 480 µmol, 67.7%).

MS: M=271.3 (M+H)+

Step 3: 2-(3-Phenyl-1-(pyridin-2-yl)-1H-1,2,4-triazol-5-yl)acetonitrile

A mixture of 2-(5-(chloromethyl)-3-phenyl-1H-1,2,4-triazol-1-yl)pyridine (130 mg, 480 µmol) and potassium cyanide (43.8 mg, 672 µmol) in DMSO (3.5 mL) was heated to 50° C. for 1.5 h. The cooled reaction mixture was poured into water (25 mL) and extracted with ethyl acetate (2×50 mL). The combined organic phase was washed with water (2×25 mL), dried over MgSO4 and concentrated in vacuo to give 110 mg crude product. The product was obtained after purification by flash chromatography (using silica gel and an ethyl acetate/heptane gradient) as white solid (30 mg, 114 µmol, 23.7%).

MS: M=262.1 (M+H)+

Step 4: 2-(3-Phenyl-1-(pyridin-2-yl)-1H-1,2,4-triazol-5-yl)ethanamine

A solution of 2-(3-phenyl-1-(pyridin-2-yl)-1H-1,2,4-triazol-5-yl)acetonitrile (28 mg, 96.4 µmol) in THF (1.5 mL)

was, under argon atmosphere, cooled to 0-5° C. Trimethylchlorosilane (83.8 mg, 98.6 μL, 772 μmol) and lithium borohydride (2M solution in THF, 193 μL, 386 μmol) were consecutively added very slowly. The ice bath was removed after 10 min and the mixture was stirred at 60° C. for 1.5 h. The reaction mixture was cooled to 0-5° C. and MeOH (1 mL) was added slowly (bubbling!). After the temperature adjusted to RT, the mixture was poured into NaOH (1M aqueous solution, 15 mL) and was extracted with dichloromethane (2×25 mL) and ethyl acetate (1×25 mL). The combined organic phase was dried over MgSO4, filtered and evaporated to give the product as yellow waxy solid (18 mg, 67.8 μmol, 70%) which was used without further purification for the next step.
MS: M=266.3 (M+H)+

Step 5: 4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide The product was obtained starting from intermediate A-1 (25.5 mg, 121.4 μmol) and 2-(3-phenyl-1-(pyridin-2-yl)-1H-1,2,4-triazol-5-yl)ethanamine (18 mg, 67.8 μmol) via HATU coupling (using 2 eq. of coupling reagent) according to the method described in example 55, step 6 as white semi-solid (9.5 mg, 20.8 mol, 30.7%).
MS: M=457.4 (M+H)+

Example 58

4-(Azetidine-1-carbonyl)-2-methyl-2H-pyrazole-3-carboxylic acid [2-(2,5-diphenyl-oxazol-4-yl)-ethyl]-amide

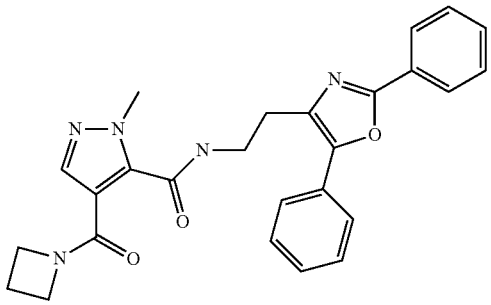 [SMILES: Cn1ncc(C(=O)N2CCC2)c1C(=O)NCCc1nc(-c2ccccc2)oc1-c1ccccc1]

Step 1: 4-Methyl-2,5-diphenyloxazole 3-oxide

To a solution of benzaldehyde (325 mg, 311 μL, 3.06 mmol) in HCl (4M in dioxane, 10 mL was added (E)-2-(hydroxyimino)-1-phenylpropan-1-one (500 mg, 3.06 mmol) at 0-5° C. The ice bath was removed and the mixture was stirred at RT for 24 h. All volatiles were removed and the residue was dissolved in HCl (4M in dioxane, 10 mL). The reaction mixture was stirred at RT for 6 h and concentrated. The obtained suspension was filtered, washed with diethyl ether and dried in vacuo to give the product as colorless solid (398 mg, 1.58 mmol, 51.7%).
MS: M=252.3 (M+H)+

Step 2: 4-(Chloromethyl)-2,5-diphenyloxazole

To a solution of 4-methyl-2,5-diphenyloxazole 3-oxide (395 mg, 1.57 mmol) in chloroform (2 mL) was added dropwise a solution of phosphorus oxychloride (265 mg, 161 μL, 1.73 mmol) in chloroform (2.00 mL) over a period of 10 min. The reaction mixture was stirred at 65° C. for 4 h and cooled to 0-5° C. At that temperature, NH4OH (25% aqueous solution, 10 mL) was added dropwise and the mixture was extracted with dichloromethane (3×40 mL). The combined organic phase was dried over MgSO4, filtered and concentrated in vacuo. The product was obtained after purification by flash chromatography (using silica gel and a dichloromethane/heptane gradient) as colorless solid (249 mg, 923 μmol, 58.7%).
MS: M=270.3 (M+H)+

Step 3: 2-(2,5-Diphenyloxazol-4-yl)acetonitrile

To a suspension of potassium cyanide (67.1 mg, 0.999 mmol) in DMSO (2 mL) was added dropwise at RT a solution of 4-(chloromethyl)-2,5-diphenyloxazole (245 mg, 908 μmol) in DMSO (3 mL) over a period of 5 min. The reaction mixture was stirred at RT for 2 h and at 45° C. for another 3 h. The reaction mixture was cooled to RT, poured into water (25 mL) and extracted with ethyl acetate (2×75 mL). The organic phases were washed with water (2×20 mL) and brine (1×20 mL). The combined organic layer was dried over MgSO4 and concentrated in vacuo to give 245 mg crude product. The product was obtained after purification by flash chromatography (using silica gel and an ethyl acetate/heptane gradient) as light yellow solid (189 mg, 726 μmol, 79.9%).
MS: M=261.2 (M+H)+

Step 4: 2-(2,5-Diphenyloxazol-4-yl)ethanamine

The product was obtained starting from 2-(2,5-diphenyloxazol-4-yl)acetonitrile (185 mg, 711 μmol) according to the method described in example 55, step 5 as yellow foam (202 mg, 535 μmol, 75.3%).
MS: M=265.2 (M+H)+

Step 5: 4-(Azetidine-1-carbonyl)-2-methyl-2H-pyrazole-3-carboxylic acid [2-(2,5-diphenyl-oxazol-4-yl)-ethyl]-amide The product was obtained starting from intermediate A-1 (30 mg, 143 μmol) and 2-(2,5-diphenyloxazol-4-yl)ethanamine (65.0 mg, 172 μmol) via HATU coupling according to the method described in example 55, step 6 as colorless solid (31 mg, 68.1 μmol, 47.5%).
MS: M=456.2 (M+H)+

Example 59

4-(Azetidine-1-carbonyl)-2-methyl-2H-pyrazole-3-carboxylic acid [2-(5-phenyl-2-pyridin-3-yl-2H-[1,2,4]triazol-3-yl)-ethyl]-amide

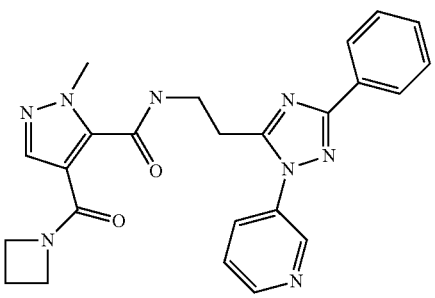 [SMILES: Cn1ncc(C(=O)N2CCC2)c1C(=O)NCCc1nc(-c2ccccc2)nn1-c1cccnc1]

Step 1: (3-Phenyl-1-(pyridin-3-yl)-1H-1,2,4-triazol-5-yl)methanol

To a solution of 3-hydrazinylpyridine dihydrochloride (336 mg, 1.84 mmol) and N,N-diisopropylethylamine (476 mg, 644 µL, 3.69 mmol) in ethanol (7 mL) was added 2-phenyloxazol-4(5H)-one (300 mg, 1.68 mmol, example 55, step 1) and the reaction mixture was refluxed for 2 h. All volatiles were removed in vacuo, and the product was obtained after purification by flash chromatography (using silica gel and a methanol/ethyl acetate gradient) as light yellow solid (390 mg, 1.546 mmol, 92.3%).

MS: M=253.1 (M+H)+

Step 2: 3-(5-(Bromomethyl)-3-phenyl-1H-1,2,4-triazol-1-yl)pyridine

The product was obtained starting from (3-phenyl-1-(pyridin-3-yl)-1H-1,2,4-triazol-5-yl)methanol (390 mg, 1.55 mmol) according to the method described in example 55, step 3 as colorless solid (130 mg, 412 µmol, 26.7%).

MS: M=317.0 (M+H)+

Step 3: 2-(3-Phenyl-1-(pyridin-3-yl)-1H-1,2,4-triazol-5-yl)acetonitrile

A mixture of potassium cyanide (30.7 mg, 472 µmol) and 3-(5-(bromomethyl)-3-phenyl-1H-1,2,4-triazol-1-yl)pyridine (124 mg, 393 µmol) in DMSO (3 mL) was stirred at RT for 2 h. The reaction mixture was poured into water (20 mL) and extracted with ethyl acetate (2×25 mL). The combined organic phase was washed with water and brine, dried, filtrated and evaporated. The product was obtained after purification by flash chromatography (using silica gel and an ethyl acetate/heptane gradient) as light brown solid (47 mg with 80% purity, 180 µmol, 36.6%).

MS: M=262.5 (M+H)+

Step 4: 2-(3-Phenyl-1-(pyridin-3-yl)-1H-1,2,4-triazol-5-yl)ethanamine

The product was obtained starting from 2-(3-phenyl-1-(pyridin-3-yl)-1H-1,2,4-triazol-5-yl)acetonitrile (47 mg, 144 µmol) according to the method described in example 55, step 5 as yellow semi-solid (28 mg with 80% purity, 84 µmol, 58.7%).

MS: M=266.5 (M+H)+

Step 5: 4-(Azetidine-1-carbonyl)-2-methyl-2H-pyrazole-3-carboxylic acid [2-(5-phenyl-2-pyridin-3-yl-2H-[1,2,4]triazol-3-yl)-ethyl]-amide The product was obtained starting from intermediate A-1 (15 mg, 71.7 µmol) and 2-(3-phenyl-1-(pyridin-3-yl)-1H-1,2,4-triazol-5-yl)ethanamine (28.5 mg, 86.0 µmol) via HATU coupling according to the method described in example 55, step 6 as colorless waxy solid (7.7 mg, 16.9 µmol, 23.5%).

MS: M=457.5 (M+H)+

Example 60

4-(Azetidine-1-carbonyl)-2-methyl-2H-pyrazole-3-carboxylic acid {2-[5-(3-fluoro-phenyl)-2-phenyl-2H-[1,2,4]triazol-3-yl]-ethyl}-amide

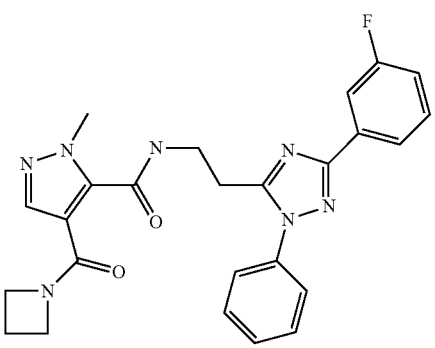 [SMILES: Cn1ncc(C(=O)N2CCC2)c1C(=O)NCCc1nc(-c2cccc(F)c2)nn1-c1ccccc1]

Step 1: Ethyl 3-fluorobenzimidate hydrochloride

A solution of 3-fluorobenzonitrile (1 g, 8.26 mmol) in ethanol (12 mL) was cooled to 0-5° C. HCl (gas) was bubbled through the mixture until saturation and the mixture was stirred at RT for 16 h. All volatiles were removed and to the residue was added diethyl ether (20 mL). The obtained suspension was filtered, washed with diethyl ether and dried in vacuo to give the product as colorless solid (1.57 g, 7.71 mmol, 93.4% yield).

MS: M=168.2 (M−HCl+H)+

Step 2: (Z)-Ethyl N-2-chloroacetyl-3-fluorobenzimidate

To a suspension of ethyl 3-fluorobenzimidate hydrochloride (400 mg, 1.96 mmol) in dichloromethane (15 mL) was added triethylamine (497 mg, 684 µL, 4.91 mmol) at RT. The reaction mixture was cooled to 0-5° C. and 2-chloroacetyl chloride (333 mg, 234 µL, 2.95 mmol) was added dropwise over a period of 5 min. After 20 min the ice bath was removed and the mixture was stirred at RT for 2 h. The reaction mixture was poured into KHSO4 (10% aqueous solution, 25 mL) and extracted with dichloromethane (3×50 mL). The combined organic layer was dried over MgSO4 and concentrated in vacuo to give the product as light brown oil (537 mg, 1.98 mmol, 101%) which was used without further purification for the next step.

MS: M=244.3 (M+H)+

Step 3: 5-(Chloromethyl)-3-(3-fluorophenyl)-1-phenyl-1H-1,2,4-triazole

The product was obtained starting from (Z)-ethyl N-2-chloroacetyl-3-fluorobenzimidate (535 mg, 1.98 mmol) and phenylhydrazine (270 mg, 246 µL, 2.37 mmol) according to the method described in example 57, step 2 as orange solid (448 mg, 1.56 mmol, 78.8%).

MS: M=288.1 (M+H)+

Step 4: 2-(3-(3-Fluorophenyl)-1-phenyl-1H-1,2,4-triazol-5-yl)acetonitrile

The product was obtained starting from 5-(chloromethyl)-3-(3-fluorophenyl)-1-phenyl-1H-1,2,4-triazole (445 mg, 1.55 mmol) according to the method described in example 58, step 3 as brown viscous oil (103 mg, 370 µmol, 23.9%).

MS: M=279.2 (M+H)+

Step 5: 2-(3-(3-Fluorophenyl)-1-phenyl-1H-1,2,4-triazol-5-yl)ethanamine

The product was obtained starting from 2-(3-(3-fluorophenyl)-1-phenyl-1H-1,2,4-triazol-5-yl)acetonitrile (100 mg, 359 µmol) according to the method described in example 55, step 5 as yellow oil (105 mg with 80% purity, 298 µmol, 82.8%).

MS: M=283.2 (M+H)+

Step 6: 4-(Azetidine-1-carbonyl)-2-methyl-2H-pyrazole-3-carboxylic acid {2-[5-(3-fluoro-phenyl)-2-phenyl-2H-[1,2,4]triazol-3-yl]-ethyl}-amide The product was obtained starting from intermediate A-1 (20 mg, 95.6 µmol) and 2-(3-(3-fluorophenyl)-1-phenyl-1H-1,2,4-triazol-5-yl)ethanamine (40.5 mg, 115 µmol) via HATU coupling according to the method described in example 55, step 6 as colorless solid (21 mg, 44.4 µmol, 46.4%).

MS: M=474.3 (M+H)+

Example 61

2-Methyl-2H-pyrazole-3,4-dicarboxylic acid 4-(cyclopentyl-methyl-amide) 3-{[2-(1-methyl-4-phenyl-1H-imidazol-2-yl)-ethyl]-amide}

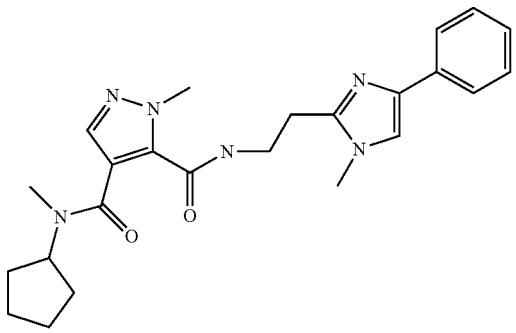 [SMILES: CN(C(=O)c1cnn(C)c1C(=O)NCCc1nc(-c2ccccc2)cn1C)C1CCCC1]

Step 1: Ethyl 1-methyl-5-(2-(1-methyl-4-phenyl-1H-imidazol-2-yl)ethylcarbamoyl)-1H-pyrazole-4-carboxylate The product was obtained starting from 4-(ethoxycarbonyl)-1-methyl-1H-pyrazole-5-carboxylic acid (200 mg, 1.01 mmol, prepared as described in US 2011/0071128) and 2-(1-methyl-4-phenyl-1H-imidazol-2-yl)ethanamine hydrochloride (288 mg, 1.21 mmol, example 7, step 4) according to the method described in example 37, step 1 as light yellow solid (252 mg, 661 µmol, 65.5%).

MS: M=382.3 (M+H)+

Step 2: 1-Methyl-5-(2-(1-methyl-4-phenyl-1H-imidazol-2-yl)ethylcarbamoyl)-1H-pyrazole-4-carboxylic acid The product was obtained starting from ethyl 1-methyl-5-(2-(1-methyl-4-phenyl-1H-imidazol-2-yl)ethylcarbamoyl)-1H-pyrazole-4-carboxylate (250 mg, 655 µmol) according to the method described in example 37, step 2 as colorless solid (224 mg, 634 µmol, 96.7%).

MS: M=354.5 (M+H)+

Step 3: 2-Methyl-2H-pyrazole-3,4-dicarboxylic acid 4-(cyclopentyl-methyl-amide) 3-{[2-(1-methyl-4-phenyl-1H-imidazol-2-yl)-ethyl]-amide}

The product was obtained starting from 1-methyl-5-(2-(1-methyl-4-phenyl-1H-imidazol-2-yl)ethylcarbamoyl)-1H-pyrazole-4-carboxylic acid (30 mg, 84.9 µmol) and N-methylcyclopentanamine (10.1 mg, 102 µmol) via COMU coupling overnight according to the method described in example 37, step 3 and after purification by preparative HPLC using an acetonitrile/water (containing 0.1% triethylamine) gradient as light red solid (27 mg, 62.1 µmol, 73.2%).

MS: M=435.4 (M+H)+

Example 62

2-Methyl-2H-pyrazole-3,4-dicarboxylic acid 4-(cyclobutyl-methyl-amide) 3-{[2-(1-methyl-4-phenyl-1H-imidazol-2-yl)-ethyl]-amide}

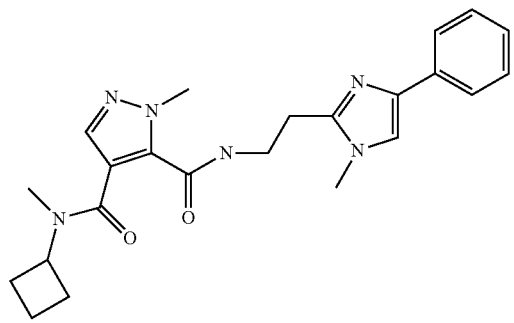 [SMILES: CN(C(=O)c1cnn(C)c1C(=O)NCCc1nc(-c2ccccc2)cn1C)C1CCC1]

The product was obtained starting from 1-methyl-5-(2-(1-methyl-4-phenyl-1H-imidazol-2-yl)ethylcarbamoyl)-1H-pyrazole-4-carboxylic acid (30 mg, 84.9 µmol, example 61, step 2) and N-methylcyclobutanamine hydrochloride (13.0 mg, 102 µmol) according to the method described in example 61, step 3 as colorless solid (25 mg, 59.5 µmol, 70.0%).

MS: M=421.3 (M+H)+

Example 63

5-(Azetidine-1-carbonyl)-3-methyl-2-trifluoromethyl-3H-imidazole-4-carboxylic acid [2-(1-methyl-4-phenyl-1H-imidazol-2-yl)-ethyl]-amide

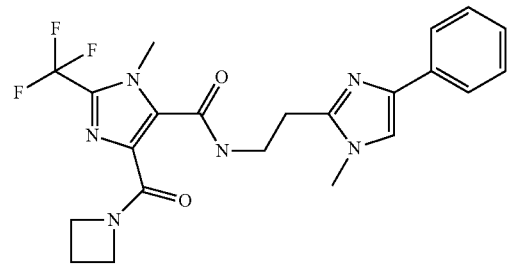 [SMILES: Cn1cc(-c2ccccc2)nc1CCNC(=O)c1c(C(=O)N2CCC2)nc(C(F)(F)F)n1C]

Step 1: 2-(Trifluoromethyl)-1H-imidazole-4,5-dicarboxylic acid

To a solution of 2-(trifluoromethyl)-1H-benzo[d]imidazole (2 g, 10.7 mmol) in H2SO4 (55.2 g, 30 mL, 535 mmol) was added slowly hydrogen peroxide (35% solution, 10.4 g, 9.41 mL, 107 mmol) at 0-5° C. The reaction mixture was stirred at 120° C. for 3 h, cooled to RT, poured into water (80 mL) under ice bath cooling and extracted with diethyl ether (3×80 mL). The combined organic phase was dried over MgSO4, filtered and evaporated to give the product as colorless solid (1.98 g, 8.84 mmol, 82.2%) which was used without further purification for the next step.
MS: M=225.4 (M+H)+

Step 2: Dimethyl 1-methyl-2-(trifluoromethyl)-1H-imidazole-4,5-dicarboxylate A mixture of 2-(trifluoromethyl)-1H-imidazole-4,5-dicarboxylic acid (1.98 g, 8.84 mmol) and 1,1,1-trimethoxyethane (14.9 g, 15.5 mL, 124 mmol) was stirred at 120° C. for 2 h. All volatiles were removed resulting in 2.58 g of light brown oil which was purified by flash chromatography (using silica gel and an ethyl acetate/heptane gradient) to give the product as light yellow oil (1.94 g, 7.29 mmol, 82.5%).
MS: M=267.4 (M+H)+

Step 3: 4-(Methoxycarbonyl)-1-methyl-2-(trifluoromethyl)-1H-imidazole-5-carboxylic acid The product was obtained starting from dimethyl 1-methyl-2-(trifluoromethyl)-1H-imidazole-4,5-dicarboxylate (500 mg, 1.88 mmol) according to the method described in example 37, step 2 as colorless solid (460 mg, 1.82 mmol, 97.1%).
MS: M=253.4 (M+H)+

Step 4: Methyl 1-methyl-5-(2-(1-methyl-4-phenyl-1H-imidazol-2-yl)ethylcarbamoyl)-2-(trifluoromethyl)-1H-imidazole-4-carboxylate The product was obtained starting from 4-(methoxycarbonyl)-1-methyl-2-(trifluoromethyl)-1H-imidazole-5-carboxylic acid (200 mg, 793 µmol) and 2-(1-methyl-4-phenyl-1H-imidazol-2-yl)ethanamine hydrochloride (226 mg, 952 µmol, example 7, step 4) according to the method described in example 7, step 5 after aqueous work-up and purification by flash chromatography (using silica gel and an ethyl acetate/heptane gradient) as white foam (128 mg, 294 µmol, 37.1%).
MS: M=436.5 (M+H)+

Step 5: 1-Methyl-5-(2-(1-methyl-4-phenyl-1H-imidazol-2-yl)ethylcarbamoyl)-2-(trifluoromethyl)-1H-imidazole-4-carboxylic acid The product was obtained starting from methyl 1-methyl-5-(2-(1-methyl-4-phenyl-1H-imidazol-2-yl)ethylcarbamoyl)-2-(trifluoromethyl)-1H-imidazole-4-carboxylate (125 mg, 287 µmol) according to the method described in example 37, step 2 as with solid (118 mg, 280 µmol, 97.5%).
MS: M=422.2 (M+H)+

Step 6: 5-(Azetidine-1-carbonyl)-3-methyl-2-trifluoromethyl-3H-imidazole-4-carboxylic acid [2-(1-methyl-4-phenyl-1H-imidazol-2-yl)-ethyl]-amide The product was obtained starting from 1-methyl-5-(2-(1-methyl-4-phenyl-1H-imidazol-2-yl)ethylcarbamoyl)-2-(trifluoromethyl)-1H-imidazole-4-carboxylic acid (30 mg, 71.2 µmol) and azetidine (4.98 mg, 5.88 µL, 85.4 µmol) via COMU coupling according to the method described in example 61, step 3 as white solid (20.5 mg, 44.5 µmol, 62.5%).
MS: M=461.5 (M+H)+

Example 64

4-(Azetidine-1-carbonyl)-2-methyl-2H-pyrazole-3-carboxylic acid (2-[1,2,4]triazolo[1,5-a]pyridin-2-yl-ethyl)-amide

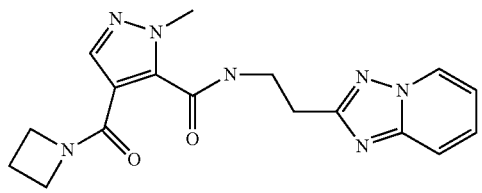 [SMILES: Cn1ncc(C(=O)N2CCC2)c1C(=O)NCCc1nc2ccccn2n1]

Step 1: O-(Mesitylsulfonyl)hydroxylamine

Under argon atmosphere, (Z)-ethyl N-mesitylsulfonyloxyacetimidate (15 g, 52.6 mmol) was dissolved in THF (13 mL) at 0° C. Perchloric acid (70% aqueous solution, 22.6 g, 13.6 mL, 158 mmol) was then added dropwise at 0-5° C. over a period of 50 min. After 10 min, precipitation started and THF (3 mL) was added. After stirring at 0° C. for 30 min, the mixture was poured into ice water (200 mL) under vigorous stirring giving a white suspension. After additional stirring for 15 min, the suspension was filtered and the precipitate was washed with ice water. The white solid was dissolved in diethyl ether (150 mL), dried over MgSO4 and evaporated at RT without heating while the flask was cooled (very important, because the compound can decompose at 25° C.!) to give O-(mesitylsulfonyl)hydroxylamine as white solid (9.2 g, 42.7 mmol, 81.3%). The crude product was used further without purification since O-(mesitylsulfonyl)hydroxylamine is unstable at 25° C.!

Step 2: 1,2-Diaminopyridinium 2,4,6-trimethylbenzenesulfonate

To a suspension of O-(mesitylsulfonyl)hydroxylamine (9.2 g, 42.7 mmol) in dichloromethane (110 mL) was added pyridin-2-amine (4.02 g, 42.7 mmol) in four portions at 0-5° C. to give a yellow solution. After 5 min the yellow solution turned into a light yellow suspension. The ice bath was removed after 10 min and the reaction mixture was stirred at RT for 1 h. The suspension was diluted with diethyl ether (100 mL), filtered, washed with diethyl ether and dried in vacuo to give the product (10.9 g, 35.2 mmol, 82.4%) as light red solid which was used without further purification for the next step.

Step 3: Ethyl[1,2,4]triazolo[1,5-a]pyridine-2-carboxylate

To a light red solution of 1,2-diaminopyridinium 2,4,6-trimethylbenzenesulfonate (10.9 g, 35.2 mmol) in pyridine (50 mL) was added ethyl 2-chloro-2-oxoacetate (9.62 g, 7.84 mL, 70.5 mmol) at RT (exotherm reaction!). The light red solution turned into a dark red solution. The mixture was heated to 100° C. and stirred overnight. The reaction mixture was evaporated and the black residue was triturated for 30 min with Na2CO3 (saturated aqueous solution, 300 mL). The reaction mixture was extracted with dichloromethane (4×250 mL) and the combined organic layer was dried over MgSO4 and concentrated in vacuo to give 6.64 g of crude product. The crude product was suspended in diethyl ether (30 mL), filtered and washed with diethyl ether. The obtained precipitate was dried in vacuo to give the product as light brown solid (6.1 g, 31.9 mmol, 90.6%).

MS: M=192.2 (M+H)+

Step 4: [1,2,4]Triazolo[1,5-a]pyridin-2-ylmethanol

Under argon atmosphere, ethyl[1,2,4]triazolo[1,5-a]pyridine-2-carboxylate (1 g, 5.23 mmol) was combined with THF (10 mL) at RT to give a brown suspension. Sodium borohydride (1.19 g, 31.4 mmol) was added in four portions. The mixture was heated to 65° C. for 15 min. After cooling down to RT, ethanol (10 mL) was added dropwise over a period of 15 min. The mixture was stirred at 65° C. for 4 h. The mixture was cooled down to 0-5° C. and NH4Cl (saturated aqueous solution, 20 mL) was added dropwise over a period of 10 min (foam!). Water (20 mL) was added and the yellow suspension was poured into dichloromethane (100 mL) and extracted with dichloromethane (4×75 mL). The combined organic layer was dried over MgSO4 and concentrated in vacuo to give the product as light yellow solid (720 mg, 4.76 mmol, 91%) which was used without further purification for the next step.

MS: M=150.1 (M+H)+

Step 5: 2-(Bromomethyl)-[1,2,4]triazolo[1,5-a]pyridine

To a brown suspension of [1,2,4]triazolo[1,5-a]pyridin-2-ylmethanol (870 mg, 5.83 mmol) and triphenylphosphine polymer bound (2.94 g, 8.75 mmol) in dichloromethane (18 mL) was slowly added carbon tetrabromide (2.9 g, 8.75 mmol) at 0-5° C. The ice bath was removed after 5 min and the reaction mixture was stirred at RT overnight. The solvent was evaporated, the brown residue was suspended in ethyl acetate (100 mL) and the organic phase was washed with water (3×50 mL) and brine (1×50 mL). The aqueous layers were back-extracted with ethyl acetate (1×100 mL) and the combined organic layer was dried over MgSO4 and concentrated in vacuo to give the product as colorless waxy solid (1.35 g with 90% purity, 5.7 mmol, 98.2%) which was used without further purification for the next step.

MS: M=214.0 (M+H)+

Step 6: 2-([1,2,4]Triazolo[1,5-a]pyridin-2-yl)acetonitrile

The product was obtained starting from 2-(bromomethyl)-[1,2,4]triazolo[1,5-a]pyridine (1.35 g, 5.73 mmol) according to the method described in example 47, step 5 as colorless solid (240 mg, 1.52 mmol, 26.5%).

MS: M=159.1 (M+H)+

Step 7: 2-([1,2,4]Triazolo[1,5-a]pyridin-2-yl)ethanamine

The product was obtained starting from 2-([1,2,4]triazolo[1,5-a]pyridin-2-yl)acetonitrile (235 mg, 1.49 mmol) according to the method described in example 55, step 5 as yellow oil (103 mg, 0.635 mmol, 42.7%) which was used without further purification for the next step.

MS: M=163.3 (M+H)+

Step 8: 4-(Azetidine-1-carbonyl)-2-methyl-2H-pyrazole-3-carboxylic acid (2-[1,2,4]triazolo[1,5-a]pyridin-2-yl-ethyl)-amide The product was obtained starting from intermediate A-1 (30 mg, 143 μmol) and 2-([1,2,4]triazolo[1,5-a]pyridin-2-yl)ethanamine (27.9 mg, 172 μmol) via HATU coupling according to the method described in example 55, step 6 as white solid (12.8 mg, 36.2 μmol, 25.3%).

MS: M=354.4 (M+H)+

Example 65

4-(Azetidine-1-carbonyl)-2-methyl-2H-pyrazole-3-carboxylic acid [2-(2-phenyl-5-pyridin-3-yl-oxazol-4-yl)-ethyl]-amide

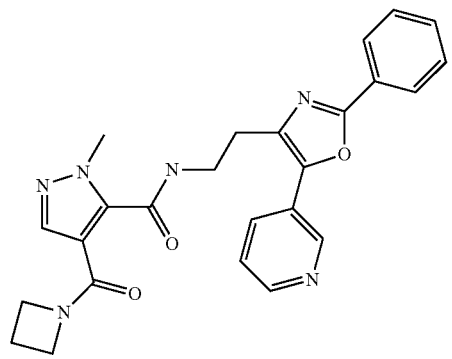 [SMILES: Cn1ncc(C(=O)N2CCC2)c1C(=O)NCCc1nc(-c2ccccc2)oc1-c1cccnc1]

Step 1: Methyl 2-phenyl-5-(pyridin-3-yl)oxazole-4-carboxylate

To a solution of methyl 3-oxo-3-(pyridin-3-yl)propanoate (4 g, 22.3 mmol) in ethyl acetate (200 mL) were added at RT tetrabutylammonium iodide (1.65 g, 4.46 mmol), benzylamine (4.78 g, 4.87 mL, 44.6 mmol) and tert-butyl hydroperoxide (5.5M solution in decane, 16.2 mL, 89.3 mmol). The reaction mixture was stirred at 40° C. for 19 h. Sodium thiosulphate (10% aqueous solution, 200 mL) was added at RT and the reaction mixture was stirred for 10 min (until negative peroxide test). The aqueous phase was separated, the organic phase was washed with water (2×100 mL) and brine (20 mL). The aqueous phases were back-extracted with ethyl acetate (1×100 mL) and the combined organic phase was dried over MgSO4, filtered and evaporated to give 11.18 g of yellow semi-solid. The product was obtained after purification by flash chromatography (using silica gel and an ethyl acetate/heptane gradient) as yellow solid (1.33 g, 4.75 mmol, 21.3% yield).

MS: M=281.2 (M+H)+

Step 2: (2-Phenyl-5-(pyridin-3-yl)oxazol-4-yl)methanol

To a solution of methyl 2-phenyl-5-(pyridin-3-yl)oxazole-4-carboxylate (1.33 g, 4.75 mmol) in THF (25 mL) was added dropwise at 0-5° C. lithium aluminum hydride (1M solution in THF, 4.75 mL, 4.75 mmol) over a period of 15 min. The reaction mixture was stirred at 0-5° C. for 1 h. Water (20 mL)

was added dropwise over a period of 10 min. The reaction mixture was poured into KHSO4 (10% aqueous solution, 75 mL) and extracted with ethyl acetate (2×100 mL). The organic phase was washed with water (2×50 mL) and brine (1×50 mL), dried over MgSO4 and concentrated in vacuo to give 490 mg crude product. The combined aqueous phases were adjusted to pH 8 with NaOH (1M solution) and extracted with dichloromethane (3×100 mL). The dichloromethane phase was dried over MgSO4, filtered and evaporated to give 480 mg brown foam. The product was obtained after purification of the combined crude products by flash chromatography (using silica gel and an ethyl acetate/heptane gradient) as light brown solid (210 mg, 832 µmol, 17.5%).

MS: M=253.1 (M+H)+

Step 3: 4-(Chloromethyl)-2-phenyl-5-(pyridin-3-yl) oxazole

To a solution of (2-phenyl-5-(pyridin-3-yl)oxazol-4-yl) methanol (210 mg, 832 µmol) and triethylamine (253 mg, 348 µL, 2.5 mmol) in dichloromethane (4 mL) was added at 0-5° C. methanesulfonyl chloride (191 mg, 130 µL, 1.66 mmol). The ice bath was removed after 10 min and the reaction mixture was stirred at RT for 2 h. The reaction mixture was poured into water (25 mL) and extracted with ethyl acetate (2×50 mL). The combined organic layer was washed with water (1×25 mL) and brine (1×25 mL), dried over MgSO4 and concentrated in vacuo to give the product as light brown solid (197 mg, 728 µmol, 87.4%) which was used without further purification for the next step.

MS: M=271.1 (M+H)+

Step 4: 2-(2-Phenyl-5-(pyridin-3-yl)oxazol-4-yl) acetonitrile

To a solution of 4-(chloromethyl)-2-phenyl-5-(pyridin-3-yl)oxazole (197 mg, 728 µmol) in DMSO (4 mL) was added at RT potassium cyanide (56.9 mg, 873 µmol). Stirring was continued for 1 h and the reaction mixture was poured into water (25 mL) and extracted with ethyl acetate (2×50 mL). The organic phases were washed with water (2×20 mL) and brine (1×20 mL). The combined organic layer was dried over MgSO4 and concentrated in vacuo to give 168 mg crude product. The product was obtained after purification by flash chromatography (using silica gel and an ethyl acetate/heptane gradient) as light yellow solid (80 mg, 306 µmol, 42.1%).

MS: M=262.2 (M+H)+

Step 5: 2-(2-Phenyl-5-(pyridin-3-yl)oxazol-4-yl) ethanamine

The product was obtained starting from 2-(2-phenyl-5-(pyridin-3-yl)oxazol-4-yl)acetonitrile (95 mg, 364 µmol) according to the method described in example 55, step 5 as light yellow viscous oil (47 mg, 177 µmol, 48.7%) which was used without further purification for the next step.

MS: M=266.2 (M+H)+

Step 6: 4-(Azetidine-1-carbonyl)-2-methyl-2H-pyrazole-3-carboxylic acid [2-(2-phenyl-5-pyridin-3-yl-oxazol-4-yl)-ethyl]-amide The product was obtained starting from intermediate A-1 (30 mg, 143 µmol) and 2-(2-phenyl-5-(pyridin-3-yl)oxazol-4-yl)ethanamine (47 mg, 177 µmol) via HATU coupling according to the method described in example 55, step 6 and consecutive purification by flash chromatography (using silica gel and a methanol/ethyl acetate gradient) as light yellow viscous oil (5.2 mg, 11.4 µmol, 8.0%).

MS: M=457.5 (M+H)+

The invention claimed is:
1. A compound of formula (I)

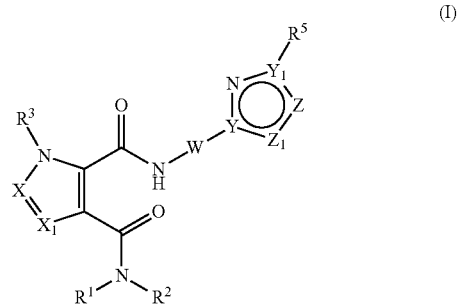

wherein:
X and $X_1$ are each independently $CR^4$ or N;
Y and $Y_1$ are each independently C or N;
Z and $Z_1$ are each independently $CR^6$, $NR^7$, N, O or S;
$R^1$ and $R^2$ are each independently selected from hydrogen, $C_1$-$C_7$-alkyl, $C_3$-$C_8$-cycloalkyl, $C_1$-$C_7$-haloalkyl, $C_1$-$C_7$-alkoxy-$C_1$-$C_7$-alkyl, heterocycloalkyl and $C_1$-$C_7$-alkyl optionally substituted by aryl or heteroaryl or
$R^1$ and $R^2$, together with the nitrogen atom to which they are attached, form a bicyclic ring system or a heterocycloalkyl optionally substituted by 1 to 3 substituents independently selected from the group consisting of hydroxyl, halogen, $C_1$-$C_7$-alkyl, $C_1$-$C_7$-alkoxy, $C_1$-$C_7$-haloalkyl and oxo;
$R^3$ is hydrogen or $C_1$-$C_7$-alkyl;
$R^4$ is hydrogen, $C_1$-$C_7$-alkyl, $C_3$-$C_8$-cycloalkyl, $C_1$-$C_7$-haloalkyl or halogen;
$R^5$ is aryl or heteroaryl each of which is optionally substituted by $C_1$-$C_7$-alkyl, $C_3$-$C_8$-cycloalkyl, halogen, $C_1$-$C_7$-haloalkyl, $C_1$-$C_7$-alkoxy, hydroxyl, $C_1$-$C_7$-hydroxyalkyl, $C_1$-$C_7$-alkoxyalkyl, acetyl, cyano, or amino optionally substituted by one or two $C_1$-$C_7$-alkyl groups;
$R^6$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl; or
$R^5$ and $R^6$, together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$-haloalkyl;
$R^7$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$ alkoxyalkyl, heterocycloalkyl, aryl, heteroaryl, or $C_1$-$C_7$-alkyl optionally substituted by aryl, heteroaryl, heterocycloalkyl, or cycloalkyl; or
$R^5$ and $R^7$, together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$ haloalkyl; and
W is ethylene which is optionally substituted by $C_1$-$C_7$ alkyl.
2. The compound of claim 1, wherein
X and $X_1$ are each independently $CR^4$ or N;
Y and $Y_1$ are each independently C or N;
Z and $Z_1$ are each independently $CR^6$, $NR^7$, O or S;

R[1] and R[2] are each independently selected from hydrogen, $C_1$-$C_7$-alkyl, $C_3$-$C_8$-cycloalkyl, $C_1$-$C_7$-haloalkyl, $C_1$-$C_7$-alkoxy-$C_1$-$C_7$-alkyl, heterocycloalkyl and $C_1$-$C_7$-alkyl optionally substituted by aryl or heteroaryl; or R[1] and R[2], together with the nitrogen atom to which they are attached, form a heterocycloalkyl optionally substituted by 1 to 3 substituents independently selected from the group consisting of hydroxyl, halogen, $C_1$-$C_7$-alkyl, $C_1$-$C_7$-alkoxy, $C_1$-$C_7$-haloalkyl and oxo;

R[3] is hydrogen or $C_1$-$C_7$-alkyl;

R[4] is hydrogen, $C_1$-$C_7$-alkyl, $C_3$-$C_8$-cycloalkyl or halogen;

R[5] is aryl or heteroaryl each of which is optionally substituted by $C_1$-$C_7$-alkyl, $C_3$-$C_8$-cycloalkyl, halogen, $C_1$-$C_7$-haloalkyl, $C_1$-$C_7$-alkoxy, hydroxyl, $C_1$-$C_7$-hydroxyalkyl, $C_1$-$C_7$-alkoxyalkyl, acetyl, cyano, or amino optionally substituted by one or two $C_1$-$C_7$-alkyl groups;

R[6] is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl; or R[5] and R[6], together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$-haloalkyl;

R[7] is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl; or R[5] and R[7], together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$-haloalkyl; and W is ethylene which is optionally substituted by $C_1$-$C_7$ alkyl.

3. The compound of claim 1, wherein W optionally substituted by $C_1$-$C_7$ alkyl.

4. The compound of claim 1, wherein R[1] and R[2], together with the nitrogen atom to which they are attached, form a 4, 5 or 6 membered heterocycloalkyl containing two heteroatoms selected from N and O;

R[3] is hydrogen or methyl;

X is nitrogen; and $X_1$ is CR[4], wherein R[4] is hydrogen.

5. The compound of claim 4, wherein R[1] and R[2], together with the nitrogen atom to which they are attached, form an azetidinyl or morpholinyl group.

6. The compound of claim 1, wherein R[1] and R[2], together with the nitrogen atom to which they are attached, form a 4, 5 or 6 membered heterocycloalkyl containing two heteroatoms selected from N and O;

R[3] is hydrogen or methyl;

X is CR[4], wherein R[4] is methyl or halogen; and $X_1$ is nitrogen.

7. The compound of claim 6, wherein R[1] and R[2], together with the nitrogen atom to which they are attached, form an azetidinyl or morpholinyl group.

8. The compound of claim 1, wherein Y is C and $Y_1$ is C or N.

9. The compound of claim 1, wherein Y is N and $Y_1$ is C.

10. The compound of claim 1, wherein Z is C and $Z_1$ is N or Z is N and $Z_1$ is C or O.

11. The compound of claim 1, wherein $Y_1$ is C, Z is CR[6] or NR[7], wherein R[5] and R[6] or R[5] and R[7], together with $Y_1$ and Z to which they are attached, form heteroaryl selected from imidazopyridinyl and benzoimidazolyl, each of which is optionally substituted by $C_1$-$C_7$ alkyl, halogen, $C_1$-$C_7$-alkoxy, or $C_1$-$C_7$-haloalkyl.

12. The compound of claim 1 having formula (Ib)

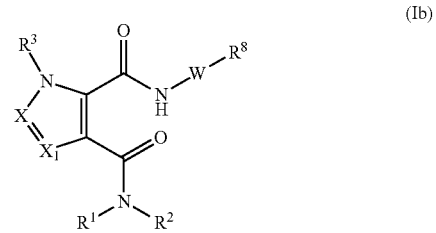

(Ib)

wherein R[8] is selected from the group consisting of:

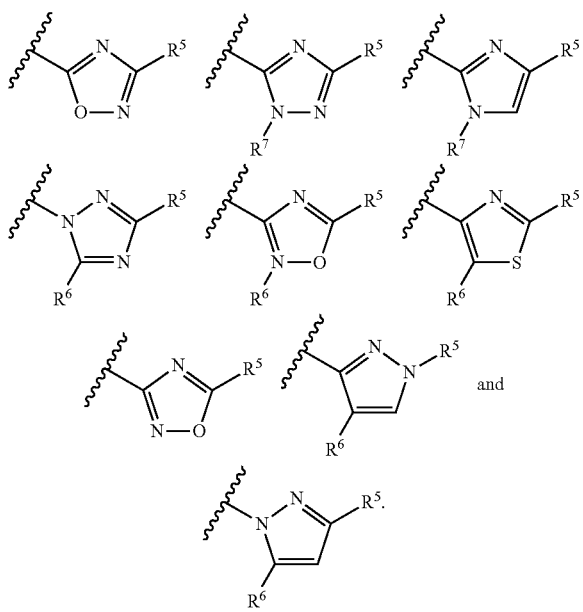

13. The compound of claim 10, wherein R[8] is selected from the group consisting of:

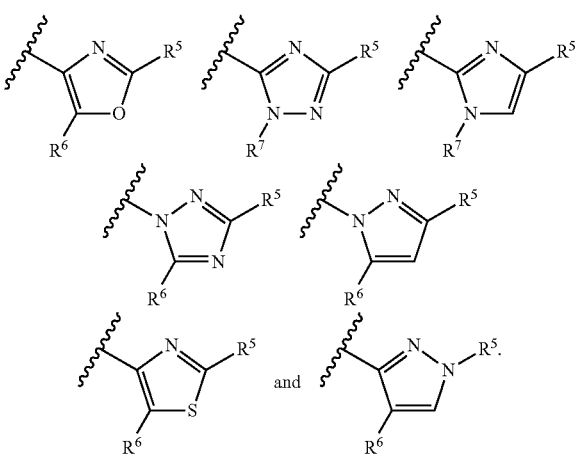

14. The compound of claim 1, wherein $R^6$ is selected from hydrogen, $C_1$-$C_7$-alkyl and heteroaryl.

15. The compound of claim 1, wherein $R^7$ is selected from hydrogen, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, and $C_1$-$C_7$-alkyl optionally substituted by aryl, heteroaryl, heterocycloalkyl, or $C_3$-$C_8$-cycloalkyl.

16. The compound of claim 1, wherein $R^5$ is selected from phenyl and pyridinyl, each of which is optionally substituted with halogen or $C_1$-$C_7$ alkoxy.

17. The compound of claim 1, selected from the group consisting of
   4-(Azetidine-1-carbonyl)-2-methyl-2H-pyrazole-3-carboxylic acid (2-imidazo[1,2-a]pyridin-2-yl-ethyl)-amide;
   4-(Azetidine-1-carbonyl)-2-methyl-2H-pyrazole-3-carboxylic acid [2-(1-methyl-1H-benzoimidazol-2-yl)-ethyl]-amide;
   4-(Azetidine-1-carbonyl)-2-methyl-2H-pyrazole-3-carboxylic acid [2-(3-phenyl-[1,2,4]oxadiazol-5-yl)-ethyl]-amide;
   4-(Azetidine-1-carbonyl)-2-methyl-2H-pyrazole-3-carboxylic acid [2-(5-pyridin-3-yl-2H-[1,2,4]triazol-3-yl)-ethyl]-amide;
   4-(Azetidine-1-carbonyl)-2-methyl-2H-pyrazole-3-carboxylic acid [2-(8-methyl-imidazo[1,2-a]pyridin-2-yl)-ethyl]-amide;
   4-(Azetidine-1-carbonyl)-2-methyl-2H-pyrazole-3-carboxylic acid {2-[3-(4-chloro-phenyl)-[1,2,4]oxadiazol-5-yl]-ethyl}-amide;
   4-(Azetidine-1-carbonyl)-2-methyl-2H-pyrazole-3-carboxylic acid [2-(1-methyl-4-phenyl-1-imidazol-2-yl)-ethyl]-amide;
   2,3-Dimethyl-5-(morpholine-4-carbonyl)-3H-imidazole-4-carboxylic acid [2-(1-methyl-1-benzoimidazol-2-yl)-ethyl]-amide;
   4-(Azetidine-1-carbonyl)-2-methyl-2H-pyrazole-3-carboxylic acid (2-benzothiazol-2-yl-ethyl)-amide;
   5-(Azetidine-1-carbonyl)-3-methyl-3H-imidazole-4-carboxylic acid [2-(1-methyl-1H-benzoimidazol-2-yl)-ethyl]-amide; and
   4-(Azetidine-1-carbonyl)-2-methyl-2H-pyrazole-3-carboxylic acid [2-(1,5-dimethyl-1H-benzoimidazol-2-yl)-ethyl]-amide.

18. The compound of claim 1, selected from the group consisting of
   4-(Azetidine-1-carbonyl)-2-methyl-2H-pyrazole-3-carboxylic acid [2-(3-phenyl-pyrazol-1-yl)-ethyl]-amide;
   5-(Azetidine-1-carbonyl)-2-chloro-3-methyl-3H-imidazole-4-carboxylic acid [2-(1-methyl-1H-benzoimidazol-2-yl)-ethyl]-amide;
   4-(Azetidine-1-carbonyl)-2-methyl-2H-pyrazole-3-carboxylic acid [2-(5-pyridin-4-yl-2H-[1,2,4]triazol-3-yl)-ethyl]-amide;
   4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide;
   4-(Azetidine-1-carbonyl)-2-methyl-2H-pyrazole-3-carboxylic acid [2-(5-chloro-1-methyl-1H-benzoimidazol-2-yl)-ethyl]-amide;
   4-(Azetidine-1-carbonyl)-2-methyl-2H-pyrazole-3-carboxylic acid [2-(2-methyl-5-pyridin-4-yl-2H-[1,2,4]triazol-3-yl)-ethyl]-amide;
   4-(Azetidine-1-carbonyl)-2-methyl-2H-pyrazole-3-carboxylic acid [2-(3-phenyl-[1,2,4]triazol-1-yl)-ethyl]-amide;
   4-(Azetidine-1-carbonyl)-2-methyl-2H-pyrazole-3-carboxylic acid [2-(2-phenyl-2H-[1,2,3]triazol-4-yl)-ethyl]-amide;
   4-(Azetidine-1-carbonyl)-2-methyl-2H-pyrazole-3-carboxylic acid [2-(5-methyl-2-phenyl-oxazol-4-yl)-ethyl]-amide;
   4-(Azetidine-1-carbonyl)-2-methyl-2H-pyrazole-3-carboxylic acid [2-(5-phenyl-[1,2,4]oxadiazol-3-yl)-ethyl]-amide; and
   4-(Azetidine-1-carbonyl)-2-methyl-2H-pyrazole-3-carboxylic acid [2-(2-methyl-5-phenyl-2H-[1,2,4]triazol-3-yl)-ethyl]-amide.

19. The compound of claim 1, selected from the group consisting of
   4-(Azetidine-1-carbonyl)-2-methyl-2H-pyrazole-3-carboxylic acid [1,1-dimethyl-2-(5-methyl-2-phenyl-oxazol-4-yl)-ethyl]-amide;
   2-Methyl-4-(morpholine-4-carbonyl)-2H-pyrazole-3-carboxylic acid [2-(1-methyl-4-phenyl-1-imidazol-2-yl)-ethyl]-amide;
   4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide;
   4-(Azetidine-1-carbonyl)-2-methyl-2H-pyrazole-3-carboxylic acid [2-(2-pyrimidin-2-yl-thiazol-4-yl)-ethyl]-amide;
   4-(Azetidine-1-carbonyl)-2-methyl-2H-pyrazole-3-carboxylic acid [2-(1-methyl-4-pyridin-3-yl-1H-imidazol-2-yl)-ethyl]-amide;
   4-(Azetidine-1-carbonyl)-2-methyl-2H-pyrazole-3-carboxylic acid [2-(1-phenyl-1H-pyrazol-3-yl)-ethyl]-amide;
   4-(Azetidine-1-carbonyl)-2-methyl-2H-pyrazole-3-carboxylic acid [2-(2-phenyl-thiazol-4-yl)-ethyl]-amide;
   4-(Azetidine-1-carbonyl)-2-methyl-2H-pyrazole-3-carboxylic acid {2-[4-(3-methoxy-phenyl)-1-methyl-1H-imidazol-2-yl]-ethyl}-amide;
   4-(Azetidine-1-carbonyl)-2-methyl-2H-pyrazole-3-carboxylic acid {2-[4-(2-methoxy-phenyl)-1-methyl-1H-imidazol-2-yl]-ethyl}-amide;
   4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide; and
   5-(Azetidine-1-carbonyl)-2,3-dimethyl-3H-imidazole-4-carboxylic acid [2-(1-methyl-4-phenyl-1-imidazol-2-yl)-ethyl]-amide.

20. The compound of claim 1, selected from the group consisting of
   4-(Azetidine-1-carbonyl)-2-methyl-2H-pyrazole-3-carboxylic acid {2-[2-(2-methoxy-ethyl)-5-phenyl-2H-[1,2,4]triazol-3-yl]-ethyl}-amide;
   4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide;
   4-(Azetidine-1-carbonyl)-2-methyl-2H-pyrazole-3-carboxylic acid [2-(5-phenyl-2H-[1,2,4]triazol-3-yl)-ethyl]-amide;
   2-Methyl-4-(morpholine-4-carbonyl)-2H-pyrazole-3-carboxylic acid [2-(5-methyl-2-phenyl-oxazol-4-yl)-ethyl]-amide;
   2-Methyl-4-(pyrrolidine-1-carbonyl)-2H-pyrazole-3-carboxylic acid [2-(5-methyl-2-phenyl-oxazol-4-yl)-ethyl]-amide;
   4-(3-Fluoro-azetidine-1-carbonyl)-2-methyl-2H-pyrazole-3-carboxylic acid [2-(5-methyl-2-phenyl-oxazol-4-yl)-ethyl]-amide;

2-Methyl-2H-pyrazole-3,4-dicarboxylic acid 4-(cyclopropyl-methyl-amide) 3-{[2-(5-methyl-2-phenyl-oxazol-4-yl)-ethyl]-amide};

2-Methyl-4-(2-oxa-6-aza-spiro[3.3]heptane-6-carbonyl)-2H-pyrazole-3-carboxylic acid [2-(5-methyl-2-phenyl-oxazol-4-yl)-ethyl]-amide;

2-Methyl-4-(thiomorpholine-4-carbonyl)-2H-pyrazole-3-carboxylic acid [2-(5-methyl-2-phenyl-oxazol-4-yl)-ethyl]-amide;

4-(Azetidine-1-carbonyl)-2-methyl-2H-pyrazole-3-carboxylic acid [2-(5-methyl-2-phenyl-thiazol-4-yl)-ethyl]-amide; and 4-(Azetidine-1-carbonyl)-2-methyl-2H-pyrazole-3-carboxylic acid [2-(5-methyl-3-phenyl-[1,2,4]triazol-1-yl)-ethyl]-amide.

21. The compound of claim 1, selected from the group consisting of 4-(Azetidine-1-carbonyl)-2-methyl-2H-pyrazole-3-carboxylic acid [2-(2-benzyl-5-phenyl-2H-[1,2,4]triazol-3-yl)-ethyl]-amide;

4-(Azetidine-1-carbonyl)-2-methyl-2H-pyrazole-3-carboxylic acid [2-(5-methyl-2-p-tolyl-thiazol-4-yl)-ethyl]-amide;

4-(Azetidine-1-carbonyl)-2-methyl-2H-pyrazole-3-carboxylic acid [2-(4-methyl-1-phenyl-1H-pyrazol-3-yl)-ethyl]-amide;

4-(Azetidine-1-carbonyl)-2-methyl-2H-pyrazole-3-carboxylic acid {2-[2-(2-ethyl-pyridin-4-yl)-5-methyl-thiazol-4-yl]-ethyl}-amide;

4-(Azetidine-1-carbonyl)-2-methyl-2H-pyrazole-3-carboxylic acid {2-(5-phenyl-2-(2,2,2-trifluoro-ethyl)-2H-[1,2,4]triazol-3-A-ethyl}-amide;

2-Methyl-4-(morpholine-4-carbonyl)-2H-pyrazole-3-carboxylic acid [2-(1-methyl-1H-benzoimidazol-2-yl)-ethyl]-amide;

2-Methyl-4-(pyrrolidine-1-carbonyl)-2H-pyrazole-3-carboxylic acid [2-(1-methyl-1H-benzoimidazol-2-yl)-ethyl]-amide;

5-(Azetidine-1-carbonyl)-3-methyl-3H-[1,2,3]triazole-4-carboxylic acid [2-(1-methyl-4-phenyl-1-imidazol-2-yl)-ethyl]-amide;

2-Methyl-2H-pyrazole-3,4-dicarboxylic acid 4-(cyclopropyl-methyl-amide) 3-{[2-(1-methyl-1H-benzoimidazol-2-yl)-ethyl]-amide};

4-(Azetidine-1-carbonyl)-2-methyl-2H-pyrazole-3-carboxylic acid [2-(5-methyl-4-phenyl-thiazol-2-yl)-ethyl]-amide; and 4-(Azetidine-1-carbonyl)-2-methyl-2H-pyrazole-3-carboxylic acid [2-(2,5-diphenyl-2H-[1,2,4]triazol-3-yl)-ethyl]-amide.

22. The compound of claim 1, selected from the group consisting of 4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide;

4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide;

4-(Azetidine-1-carbonyl)-2-methyl-2H-pyrazole-3-carboxylic acid [2-(2,5-diphenyl-oxazol-4-yl)-ethyl]-amide;

4-(Azetidine-1-carbonyl)-2-methyl-2H-pyrazole-3-carboxylic acid [2-(5-phenyl-2-pyridin-3-yl-2H-[1,2,4]triazol-3-yl)-ethyl]-amide;

4-(Azetidine-1-carbonyl)-2-methyl-2H-pyrazole-3-carboxylic acid {2-[5-(3-fluoro-phenyl)-2-phenyl-2H-[1,2,4]triazol-3-yl]-ethyl}-amide;

2-Methyl-2H-pyrazole-3,4-dicarboxylic acid 4-(cyclopentyl-methyl-amide) 3-{[2-(1-methyl-4-phenyl-1H-imidazol-2-yl)-ethyl]-amide};

2-Methyl-2H-pyrazole-3,4-dicarboxylic acid 4-(cyclobutyl-methyl-amide) 3-{[2-(1-methyl-4-phenyl-1H-imidazol-2-yl)-ethyl]-amide};

5-(Azetidine-1-carbonyl)-3-methyl-2-trifluoromethyl-3H-imidazole-4-carboxylic acid [2-(1-methyl-4-phenyl-1H-imidazol-2-yl)-ethyl]-amide;

4-(Azetidine-1-carbonyl)-2-methyl-2H-pyrazole-3-carboxylic acid (2-[1,2,4]triazolo[1,5-a]pyridin-2-yl-ethyl)-amide; and 4-(Azetidine-1-carbonyl)-2-methyl-2H-pyrazole-3-carboxylic acid [2-(2-phenyl-5-pyridin-3-yl-oxazol-4-yl)-ethyl]-amide.

23. The compound of claim 1, selected from the group consisting of 4-(Azetidine-1-carbonyl)-2-methyl-2H-pyrazole-3-carboxylic acid {2-[1-(2-methoxy-ethyl)-4-phenyl-1H-imidazol-2-yl]-ethyl}-amide;

4-(Azetidine-1-carbonyl)-2-methyl-2H-pyrazole-3-carboxylic acid [2-(1-methyl-4-pyridin-3-yl-1H-imidazol-2-yl)-ethyl]-amide;

4-(Azetidine-1-carbonyl)-2-methyl-2H-pyrazole-3-carboxylic acid [2-(2-methyl-5-phenyl-2H-[1,2,4]triazol-3-yl)-ethyl]-amide;

4-(Azetidine-1-carbonyl)-2-methyl-2H-pyrazole-3-carboxylic acid [2-(2-methyl-5-pyridin-3-yl-2H-[1,2,4]triazol-3-yl)-ethyl]-amide;

4-(Azetidine-1-carbonyl)-2-methyl-2H-pyrazole-3-carboxylic acid [2-(5-chloro-1-methyl-1H-benzoimidazol-2-yl)-ethyl]-amide;

4-(Azetidine-1-carbonyl)-2-methyl-2H-pyrazole-3-carboxylic acid [2-(2-phenyl-2H-[1,2,3]triazol-4-yl)-ethyl]-amide; and 4-(Azetidine-1-carbonyl)-2-methyl-2H-pyrazole-3-carboxylic acid [2-(5-phenyl-[1,2,4]oxadiazol-3-yl)-ethyl]-amide.

24. The compound of claim 1, selected from the group consisting of 4-(Azetidine-1-carbonyl)-2-methyl-2H-pyrazole-3-carboxylic acid [1,1-dimethyl-2-(5-methyl-2-phenyl-oxazol-4-yl)-ethyl]-amide;

4-(Azetidine-1-carbonyl)-2-methyl-2H-pyrazole-3-carboxylic acid [1,1-dimethyl-2-(3-phenyl-[1,2,4]oxadiazol-5-yl)-ethyl]-amide;

4-(Azetidine-1-carbonyl)-2-methyl-2H-pyrazole-3-carboxylic acid [2-(2-cyclopropylmethyl-5-phenyl-2H-[1,2,4]triazol-3-yl)-ethyl]-amide;

4-(Azetidine-1-carbonyl)-2-methyl-2H-pyrazole-3-carboxylic acid [2-(2,5-diphenyl-2H-[1,2,4]triazol-3-yl)-ethyl]-amide;

4-(Azetidine-1-carbonyl)-2-methyl-2H-pyrazole-3-carboxylic acid [2-(2-cyclopropyl-5-phenyl-2H-[1,2,4]triazol-3-yl)-ethyl]-amide;

4-(Azetidine-1-carbonyl)-2-methyl-2H-pyrazole-3-carboxylic acid [2-(5-phenyl-2-pyridin-2-yl-2H-[1,2,4]triazol-3-yl)-ethyl]-amide;

2-Methyl-2H-pyrazole-3,4-dicarboxylic acid 4-(cyclobutyl-methyl-amide) 3-{[2-(1-methyl-4-phenyl-1H-imidazol-2-yl)-ethyl]-amide}.

25. A pharmaceutical composition comprising a therapeutically effective amount of a compound of formula (I)

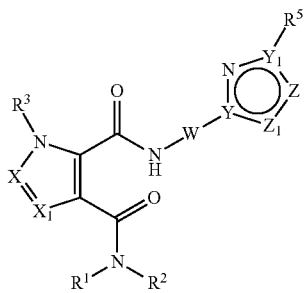

wherein:
- X and $X_1$ are each independently $CR^4$ or N;
- Y and $Y_1$ are each independently C or N;
- Z and $Z_1$ are each independently $CR^6$, $NR^7$, N, O or S;
- $R^1$ and $R^2$ are each independently selected from hydrogen, $C_1$-$C_7$-alkyl, $C_3$-$C_8$-cycloalkyl, $C_1$-$C_7$-haloalkyl, $C_1$-$C_7$-alkoxy-$C_1$-$C_7$-alkyl, heterocycloalkyl and $C_1$-$C_7$-alkyl optionally substituted by aryl or heteroaryl; or
- $R^1$ and $R^2$, together with the nitrogen atom to which they are attached, form a bicyclic ring system or a heterocycloalkyl optionally substituted by 1 to 3 substituents independently selected from the group consisting of hydroxyl, halogen, $C_1$-$C_7$-alkyl, $C_1$-$C_7$-alkoxy, $C_1$-$C_7$-haloalkyl and oxo;
- $R^3$ is hydrogen or $C_1$-$C_7$-alkyl;
- $R^4$ is hydrogen, $C_1$-$C_7$-alkyl, $C_3$-$C_8$-cycloalkyl, $C_1$-$C_7$-haloalkyl or halogen;
- $R^5$ is aryl or heteroaryl each of which is optionally substituted by $C_1$-$C_7$-alkyl, $C_3$-$C_8$-cycloalkyl, halogen, $C_1$-$C_7$-haloalkyl, $C_1$-$C_7$-alkoxy, hydroxyl, $C_1$-$C_7$-hydroxyalkyl, $C_1$-$C_7$-alkoxyalkyl, acetyl, cyano, or amino optionally substituted by one or two $C_1$-$C_7$-alkyl groups;
- $R^6$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl; or
- $R^5$ and $R^6$, together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$-haloalkyl;
- $R^7$ is hydrogen, halogen, $C_1$-$C_7$-alkyl, $C_3$-$C_8$-cycloalkyl, $C_1$-$C_7$-alkoxy, $C_1$-$C_7$-haloalkyl, $C_1$-$C_7$-alkoxyalkyl, heterocycloalkyl, aryl, heteroaryl, or $C_1$-$C_7$-alkyl optionally substituted by aryl, heteroaryl, heterocycloalkyl, or cycloalkyl; or
- $R^5$ and $R^7$, together with the $Y_1$ and Z atom to which they are attached, form aryl or heteroaryl each of which is optionally substituted by $C_1$-$C_7$ alkyl, halogen, $C_1$-$C_7$-alkoxy, or $C_1$-$C_7$-haloalkyl; and
- W is selected from ethylene which is optionally substituted by $C_1$-$C_7$ alkyl and a pharmaceutically acceptable carrier.

* * * * *